US008980843B2

(12) United States Patent
Otvos, Jr.

(10) Patent No.: US 8,980,843 B2
(45) Date of Patent: Mar. 17, 2015

(54) LEPTIN AGONIST AND METHODS OF USE

(75) Inventor: Laszlo Otvos, Jr., Audubon, PA (US)

(73) Assignee: Temple University—of the Commonwealth System of Higher Education, Philadelphia, PA (US)

( * ) Notice: Subject to any disclaimer, the term of this patent is extended or adjusted under 35 U.S.C. 154(b) by 583 days.

(21) Appl. No.: 13/381,576

(22) PCT Filed: Jun. 25, 2010

(86) PCT No.: PCT/US2010/039935
§ 371 (c)(1),
(2), (4) Date: Dec. 29, 2011

(87) PCT Pub. No.: WO2011/002673
PCT Pub. Date: Jan. 6, 2011

(65) Prior Publication Data
US 2012/0108504 A1 May 3, 2012

Related U.S. Application Data

(60) Provisional application No. 61/222,248, filed on Jul. 1, 2009.

(51) Int. Cl.
*A61K 38/10* (2006.01)
*C07K 7/02* (2006.01)
*A61K 38/16* (2006.01)
*A61K 38/00* (2006.01)
*A61K 38/22* (2006.01)
*A61K 49/00* (2006.01)
*C07K 14/575* (2006.01)

(52) U.S. Cl.
CPC ......... *A61K 49/0017* (2013.01); *C07K 14/5759* (2013.01)
USPC ........... 514/21.5; 514/21.3; 514/5.8; 514/4.8; 514/4.9; 530/327; 530/324

(58) Field of Classification Search
None
See application file for complete search history.

(56) References Cited

U.S. PATENT DOCUMENTS

| | | | |
|---|---|---|---|
| 6,777,388 B1 | 8/2004 | Grasso et al. | |
| 7,208,572 B2 | 4/2007 | Grasso et al. | |
| 8,470,772 B2 * | 6/2013 | Surmacz et al. | 514/5.8 |
| 2005/0288223 A1 | 12/2005 | Lucas et al. | |
| 2006/0003938 A1 | 1/2006 | Otvos | 514/12 |
| 2006/0040861 A1 | 2/2006 | Iwamoto | 514/12 |
| 2006/0099150 A1 | 5/2006 | Houston et al. | 424/46 |
| 2006/0276416 A1 | 12/2006 | Sinclair et al. | |
| 2011/0015124 A1 | 1/2011 | Surmacz et al. | 514/4.8 |

FOREIGN PATENT DOCUMENTS

| | | | |
|---|---|---|---|
| WO | WO 00/11173 | 3/2000 | C12N 15/16 |
| WO | WO 01/21647 | 3/2001 | C07K 14/00 |
| WO | WO 02/062833 | 8/2002 | C07K 14/00 |
| WO | WO 02/066514 | 8/2002 | C07K 16/00 |
| WO | WO 2004/039832 | 5/2004 | |

OTHER PUBLICATIONS

Knappe, 2008, Int. J. Res. Ther., 14, 247-254.*
Otvos, et al., "Leptin-Based Agonists and Antagonists Acting on the Leptin—Leptin Receptor Interface", Abstracts of 20th American Peptide Society Symposium, Jun. 26-30, Montreal, Canada, *Peptide Sciences* 88(4):556, Abstr. 172, (Jun. 4, 2007).
Banks, et al., "Leptin enters the brain by a saturable system independent of insulin", *Peptides* 17 (1996) 305-311.
Banks, et al., "The blood-brain barrier as a cause of obesity", *Curr. Pharm. Des.* 14 (2008) 1606-1614.
Banks, et al., "Characterization of lectin-mediated brain uptake of HIV-1 GP120", *J. Neurosci. Res.* 54 (1998) 522-529.
Bodor, et al., "Novel, cell-penetrating molecular transporters with flexible backbones and permanently charged side-chains", *J. Pharm. Pharmacol.* 59 (2007) 1065-1076.
Chan, J.L., et al. "Role of leptin in energy-deprivation states: normal human physiology and clinical implications for hypothalamic amenorrhea and anorexia nervosa" *The Lancet*, 366:9479, pp. 74-85 (2005).
Dhanasekaran, M., et al., "New Prospects for Glycopeptide Based Analgesia: Glycoside-Induced Penetration of the Blood-Brain Barrier", *Current Drug Delivery*, 2, pp. 59-73 (2005).
Egleton, R.D., et al., "Improved bioavailability to the brain of glycosylated Met-enkephalin analogs", *Brain Research*, 881, pp. 37-46 (2000).
Farooqi, et al., "Mutations in ligands and receptors of the leptin-melanocortin pathway that lead to obesity", *Nature Endocrin. Metabolism* 4 (2008) 569-577.
Garofalo, et al., "Leptin and cancer", *J. Cell. Physiol.* 207 (2006) 12-22.
Grasso, et al., "In vivo effects of leptin-related synthetic peptides on body weight and food intake in female ob/ob mice: Localization of leptin activity to domains between amino acid residues" (106-140), *Endocrinology* 138 (1997) 1413-1418.
Gonzalez, et al., "A Peptide Derived from the Human Leptin Molecule Is a Potent Inhibitor of the Leptin Receptor Function in Rabbit Endometrial Cells," *Endocrine*, vol. 21, No. 2, pp. 185-195, Jul. 2003.
Iserentant, et al., "Mapping of the interface between leptin and the leptin receptor CRH2 domain," *Journal of Cell Science*, 118:2519-2527 (Mar. 16, 2005).
Knappe, et al., "Drug Development-targeted Screening of Leptin Agonist Glycopeptides", *International Journal peptide Research and Therapeutics* 2008, 14: 247-254.
Kovalszky, et al., "Leptin-based glycopeptides induces weight loss and simultaneously restores fertility in animal models", *Diabetes Obes Metab.*, May 2010, 12(5): 393-402.

(Continued)

*Primary Examiner* — Satyanarayana R Gudibande
(74) *Attorney, Agent, or Firm* — Drinker Biddle & Reath LLP

(57) ABSTRACT

Peptides are provided having leptin receptor agonist activity. The peptides are useful for treating obesity, type II diabetes, appetite control after bariatric surgery, insulin resistance, lipodystrophy and hypothalamic amenorrhea, obesity-related infertility, among other diseases and conditions related to leptin deficiency and/or leptin resistance.

39 Claims, 6 Drawing Sheets

(56) References Cited

OTHER PUBLICATIONS

Lo, et al., "Engineering a pharmacologically superior form of leptin for the treatment of obesity", *Prot. Eng. Des. Sel.* 18 (2005) 1-10.

Maness, et al., "Fate of leptin after intracerebroventricular injection into the mouse brain", *Endocrinology* 139 (1998) 4556-4562.

Niv-Spector, et al., "Identification of the hydrophobic strand in the A-B loop of leptin as major binding site III: implications for large-scale preparation of potent recombinant human and ovine leptin antagonists", *Biochem. J.*, (2005) 391:221-230.

Otvos, Jr., et al., "Development of a pharmacologically improved peptide agonist of the leptin receptor," *Biochimica et Biophysica Acta*, 2008 1783:1745-1754.

Otvos, et al., "A leptin receptor agonist glycopeptides for leptin replacement therapy", *Peptides* 2008 (H. Lankinen, ed), European Peptide Socity, Helsinki, pp. 436-437.

Peelman, et al., "Mapping of the Leptin Binding Sites and Design of a Leptin Antagonist", *The Journal of Biological Chemistry*, vol. 279, No. 39, Issue of Sep. 24, pp. 41038-41046, 2004.

Polt, et al., "Glycopeptide enkephalin analogues produce analgesia in mice; evidence for penetration of the blood-barrier", *Proc. Natl. Acad. Sci. USA* 91 (1994) 7114-7118.

Shimomura, et al., "Leptin reverses insulin resistance and diabetes mellitus in mice with congenital lipodystrophy", *Nature* 401 (1999) 73-76.

Verploegen, et al., "A human leptin mutant induces weight gain in normal mice", *FEBS Lett.* 405 (1997) 237-240.

Wauters, et al., "Human leptin: from an adipocyte hormone to an endocrine mediator", *Eur. J. Endocrinol.* 143 (2000) 293-311.

Witt, K.A., et al. "Peptide drug modifications to enhance bioavailability and blood-brain barrier permeability", *Peptides*, 22, pp. 2329-2343 (2001).

Zhang, et al., "Tat-modified leptin is more accessible to hypothalamus through brain-blood barrier with a significant inhibition of body weight gain in high fat diet-fed mice", *Exp. Clin. Endocrinol. Diabetes*, in press (2009).

Zhang, et al., "Positional cloning of the mouse obese gene and its human homologue", *Nature* 372 (1994) 425-432.

\* cited by examiner (A)        (B)

LEPTIN AGONIST AND METHODS OF USE

CROSS-REFERENCE TO RELATED APPLICATIONS

This application claims the benefit of U.S. Provisional Application No. 61/222,248, filed Jul. 1, 2009, the entire disclosure of which is incorporated herein by reference.

FIELD OF INVENTION

The invention relates to leptin agonists and their use in treatment of obesity and metabolic diseases.

BACKGROUND OF THE INVENTION

Leptin is a neurohormone that acts in the hypothalamus to regulate energy balance and food intake (amino acid sequence SEQ ID NO:1; Wauters et al., 2000, Eur. J. Endocrinol. 143: 293-311). Recessive mutations in the leptin or the gene for its receptor, ObR, result in profound obesity and type II diabetes mellitus (Zhang et al., 1994, Nature 372: 425-432). In addition to its role as a neurohormone and energy regulator, leptin can modulate several physiological processes, such as fertility, lactation, immune response, bone remodeling, hematopoiesis, and cognitive functions. On a cellular level, leptin can act as a mitogen, survival factor, metabolic regulator or pro-angiogenic factor (Wauters et al., 2000, Eur. J. Endocrinol. 143: 293-311).

Mature human leptin is secreted as a 146-amino acid protein. Leptin binds to the extracellular domain of its receptor, ObR, which can be expressed as multiple isoforms. The long isoform of ObR (ObR1) can induce multiple intracellular signaling pathways, for instance, the classic cytokine JAK2/STAT3 (Janus kinase 2/signal transducer and activator of transcription 3) pathway; the Ras/ERK1/2 (Ras/extracellular signal-regulated kinases 1/2) signaling cascade; and the PI-3K/Akt/GSK3 (phosphoinositide 3 kinase/protein kinase B/glycogen synthase kinase 3) growth/antiapoptotic pathway. In addition, leptin has been found to induce PLC (phospholipase C)-γ, PKC (protein kinase C), p38 kinase, and nitric oxide (NO) production (Bjorbaek et al., 1997, J. Biol. Chem. 272: 32686-32695; Sweeney, 2002, Cell. Signal. 14: 655-663; Zabeau et al., 2003, FEBS Lett. 546: 45-50). Ultimately, induction of ObR1 can activate several genes involved in cell proliferation, including c-fos, c-jun, junB, egr-1, and socs3, and upregulate the expression of angiogenic factors, such as VEGF (Sweeney, 2002, Cell. Signal. 14: 655-663; Zabeau et al., 2003, FEBS Lett. 546: 45-50; Frankenberry et al., 2004, Am. J. Surg. 188: 560-565).

Leptin comprises a bundle of 4 helices (helices A-D), with an up-up-down-down topology (Zhang et al., 1997, Nature 387: 206-209). Superimposition of the leptin sequence with other cytokines, such as human IL-6, bovine G-CSF and human oncostatin M, revealed three potential bivalent receptor binding sites (sites mostly around the pairwise helices (Peelman et al., 2004, J. Biol. Chem. 279: 41038-41046).

The receptor binding site around residue 40 of leptin is labeled as site I. The residues at the very N-terminus and in the middle of the protein are labeled as binding site II, and the residues at the C-terminus as binding site III. Interfering with these binding surfaces may increase or decrease the efficiency of leptin/ObR binding and modulate downstream ObR signaling. As a first indication of the possibility of growth arrest upon ObR inactivation, the proliferation rate of leptin-sensitive BAF/3 cells stably transfected with the long form of human leptin receptor was measured after treatment of leptin fragments and their mutants (Niv-Spector et al., 2005, Biochem. J. 391: 221-230). Single-point mutations in leptin binding site III were shown to lower the affinity between the ligand and the receptor, attenuating the agonistic activity and converting those mutants into both partial antagonists and weak agonists.

Full-length leptin and point mutants of full-length leptin have been examined as potential therapeutic agents for obesity, lipodystrophy, diet-induced food craving, weight-loss management, and hypothalamic amenorrhea. However, these trials have been hampered by development of leptin resistance in obese people, as well as disadvantageous pharmacological parameters of recombinant leptin drug candidates (Lo et al., 2005, Prot. Eng. Des. Sel. 18: 1-10). Leptin crosses the blood-brain barrier (BBB) by a saturable system (Banks et al., 1996, Peptides 17: 305-311), presumably comprising some ObR forms residing at the brain side of the barrier and in the lumen of cerebral arteries (Maness et al., 1998, Endocrinology 139: 4556-4562). Clinical leptin resistance is thought to be related, at least in part, to inefficient BBB penetration (Banks, 2008, Curr. Pharm. Des. 14: 1606-1614; Montez et al., 2005, Proc. Natl. Acad. Sci. USA 102: 2537-2542).

The multiple roles that leptin plays in biological processes suggest that it is not straightforward to obtain true agonists or antagonists that do not change the downstream signaling effect upon varying environmental conditions. Indeed, the identification of partial antagonists and weak agonists of leptin indicates that, depending upon the cell lines used, as well as the presence or absence of native unmodified leptin, the same mutant protein or large subunit can trigger different biological responses. The use of such proteins and peptides in human or veterinary therapy may thus be problematic, as the peptides do not demonstrate pure, controllable agonist or antagonistic activity against the leptin receptor.

In the context of energy balance, leptin plays a key role in regulating energy balance and food intake. Disruption in normal leptin production or activity causes severe obesity cases in affected individuals. A leptin antagonist may be used to cause weight gain or stop weight loss in individuals with a severe case of nutrition disorder, such as cachexia or wasting. On the other hand, a synthetic or recombinant form of leptin, or a leptin agonist, may be used to reduce body weight and glucose levels in obese animals, as well as increase insulin sensitivity. A treatment using a leptin agonist would only be successful if a resistance mechanism similar to that observed for leptin were absent.

There is therefore a need for a leptin-based agonist that may be used to treat leptin-deficient diseases such as obesity, metabolic syndrome, weight-loss management, type II diabetes, appetite control after bariatric surgery, lipodystrophy, diet-induced food craving, insulin resistance, hypothalamic amenorrhea and obesity-related infertility. The present invention addresses and meets these needs.

SUMMARY OF THE INVENTION

The present invention is based on the unexpected discovery that certain leptin-based compounds act as agonists of the leptin receptor (ObR), without displaying significant antagonistic activity, and may thus be considered as "full agonists". In one aspect, the compounds of the invention stimulate the growth of ObR-positive cells (agonistic effect) at lower concentrations than the native ligand when added alone, and do not antagonize the actions of leptin (antagonistic effect) in the same cells. In another aspect, the compounds of the invention have a more extended duration of action than the native leptin. The concentrations at which antagonistic effects may be observed are at least 100 times higher than those at which agonistic effects are observed. Therefore, the agonist:antagonist selectivity ratio for the compounds of the invention is equal to or greater than about 100. The compounds of the invention may find use in treating or preventing the development of obesity, as well as metabolic diseases, such as lipodystrophy, obesity-related infertility, metabolic syndrome, hypothalamic amenorrhea, diet-induced food craving, weight-loss management, type II diabetes, appetite control after bariatric surgery, and insulin resistance.

The invention includes a compound according to Formula (I):

X1-M-SEQ ID NO:2                             (I)

or a salt thereof, wherein:
SEQ ID NO:2 represents $Xaa_1$-$Xaa_2$-$Xaa_3$-Glu-Val-Val-Ala-Leu-Ser-$Xaa_4$-$Xaa_5$, wherein:
  $Xaa_1$ is Tyr, Tyr(Me), Tyr(N-Me), Tyr(Me, N-Me), Tyr(I) or Tyr($I_2$);
  $Xaa_2$ is Ser or a saccharide-modified serine;
  $Xaa_3$ is Thr or a saccharide-modified threonine;
  $Xaa_4$ is Arg or Arg(N-Me);
  $Xaa_5$ is a non-natural amino acid; and,
  X1-M represents an optional group comprising a tagging element conjugated to the N-terminus of the amino acid sequence SEQ ID NO:2, wherein:
    X1 represents the tagging element, wherein the tagging element is selected from the group consisting of a transduction domain and a detection label; and,
    -M- represents a single bond or an optional linking group forming a covalent linkage between the tagging element and the amino acid sequence SEQ ID NO:2.

In one embodiment, -M- consists of a single bond, an amino acid or a peptide. In another embodiment, the tagging domain is directly linked at its C-terminus to -M-. In yet another embodiment, the tagging element is a transduction domain comprising an amino acid sequence selected from the group consisting of Tyr-Gly-Arg-Lys-Lys-Arg-Arg-Gln-Arg-Arg-Arg [amino acid sequence SEQ ID NO:5], Arg-Lys-Lys-Arg-Arg-Gln-Arg-Arg-Arg [amino acid sequence SEQ ID NO:6], Gly-Arg-Lys-Lys-Arg-Arg-Gln-Arg-Arg-Arg-Gly-Tyr-Lys-Cys [amino acid sequence SEQ ID NO:7], Tyr-Gly-Arg-Lys-Lys-Arg-Arg-Gln-Arg-Arg-Arg-Gly [amino acid sequence SEQ ID NO:8], Gly-Arg-Lys-Lys-Arg-Arg-Gln-Arg-Arg-Arg-Pro-Pro-Gln-Cys [amino acid sequence SEQ ID NO:9], Gly-Arg-Lys-Lys-Arg-Arg-Gln-Arg-Arg-Arg-Pro-Pro-Gln [amino acid sequence SEQ ID NO:10], Tyr-Ala-Arg-Lys-Ala-Arg-Arg-Gln-Ala-Arg-Arg [amino acid sequence SEQ ID NO:11], Tyr-Ala-Arg-Ala-Ala-Ala-Arg-Gln-Ala-Arg-Ala [amino acid sequence SEQ ID NO:12], Tyr-Ala-Arg-Ala-Ala-Arg-Arg-Ala-Ala-Arg-Arg [amino acid sequence SEQ ID NO:13], Tyr-Ala-Arg-Ala-Ala-Arg-Arg-Ala-Ala-Arg-Ala [amino acid sequence SEQ ID NO:14], Arg-Gln-Ile-Lys-Ile-Trp-Phe-Gln-Asn-Arg-Arg-Met-Lys-Trp-Lys-Lys [amino acid sequence SEQ ID NO:15], Arg-Gln-Ile-Lys-Ile-Trp-Phe-Pro-Asn-Arg-Arg-Met-Lys-Trp-Lys-Lys [amino acid sequence SEQ ID NO:16], Lys-Lys-Trp-Lys-Met-Arg-Arg-Asn-Gln-Phe-Trp-Val-Lys-Val-Gln-Arg [amino acid sequence SEQ ID NO:17], Arg-Arg-Trp-Arg-Arg-Trp-Trp-Arg-Arg-Trp-Trp-Arg-Arg-Trp-Arg-Arg [amino acid sequence SEQ ID NO:18], Arg-Arg-Met-Lys-Trp-Lys-Lys [amino acid sequence SEQ ID NO:19], Apa-Arg-Gln-Ile-Lys-Ile-Trp-Phe-Gln-Asn-Arg-Arg-Met-Lys-Trp-Lys-Lys [amino acid sequence SEQ ID NO:20], Apa-Arg-Gln-Ile-Lys-Ile-Trp-Phe-Pro-Asn-Arg-Arg-Met-Lys-Trp-Lys-Lys [amino acid sequence SEQ ID NO:21], Arg-Arg-Arg-Arg-Arg-Arg-Arg-Arg [amino acid sequence SEQ ID NO:22], Arg-Arg-Arg-Arg-Arg-Arg-Arg-Arg-Arg [amino acid sequence SEQ ID NO:23], Asp-Ala-Ala-Thr-Arg-Ser-Ala-Ala-Ser-Arg-Pro-Thr-Glu-Arg-Pro-Arg-Ala-Pro-Ala-Arg-Ser-Ala-Ser-Arg-Pro-Arg-Arg-Pro-Val-Glu [amino acid sequence SEQ ID NO:24], Gly-Ala-Leu-Phe-Leu-Gly-Trp-Leu-Gly-Ala-Ala-Gly-Ser-Thr-Met-Gly [amino acid sequence SEQ ID NO:25], Gly-Ala-Leu-Phe-Leu-Gly-Phe-Leu-Gly-Ala-Ala-Gly-Ser-Thr-Met-Gly-Ala-Trp-Ser-Gln-Pro-Lys-Ser-Lys-Arg-Lys-Val [amino acid sequence SEQ ID NO:26], Met-Gly-Leu-Gly-Leu-His-Leu-Leu-Val-Leu-Ala-Ala-Ala-Leu-Gln-Gly-Ala-Trp-Ser-Gln-Pro-Lys-Lys-Lys-Arg-Lys-Val [amino acid sequence SEQ ID NO:27], Pro-Leu-Ser-Ser-Ile-Phe-Ser-Arg-Ile-Gly-Asp-Pro [amino acid sequence SEQ ID NO:28], Phe-Trp-Arg-Gly-Asp-Leu-Val-Phe-Asp-Phe-Gln-Val [amino acid sequence SEQ ID NO:29], Lys-Phe-Thr-Ile-Val-Phe-Pro-His-Asn-Gln-Lys-Gly-Asn-Trp-Lys-Asn-Val-Pro-Ser-Asn-Tyr-His-Tyr-Cys-Pro [amino acid sequence SEQ ID NO:30], Ala-Lys-Arg-Ala-Arg-Leu-Ser-Thr-Ser-Phe-Asn-Pro-Val-Tyr-Pro-Tyr-Glu-Asp-Glu-Ser [amino acid sequence SEQ ID NO:31], Gly-Trp-Thr-Leu-Asn-Ser-Ala-Gly-Tyr-Leu-Leu-Gly-Lys-Ile-Asn-Leu-Lys-Ala-Leu-Ala-Ala-Leu-Ala-Lys-Lys-Ile-Leu [amino acid sequence SEQ ID NO:32], Arg-Gly-Gly-Arg-Leu-Ser-Tyr-Ser-Arg-Arg-Arg-Phe-Ser-Thr-Ser-Thr-Gly-Arg [amino acid sequence SEQ ID NO:33], Ala-Ala-Val-Ala-Leu-Leu-Pro-Ala-Val-Leu-Leu-Ala-Leu-Leu-Ala-Pro [amino acid sequence SEQ ID NO:34], Ala-Ala-Val-Leu-Leu-Pro-Val-Leu-Leu-Ala-Ala-Pro [amino acid sequence SEQ ID NO:35], Val-Thr-Val-Leu-Ala-Leu-Gly-Ala-Leu-Ala-Gly-Val-Gly-Val-Gly [amino acid sequence SEQ ID NO:36], Val-Ala-Tyr-Ile-Ser-Arg-Gly-Gly-Val-Ser-Thr-Tyr-Tyr-Ser-Asp-Thr-Val-Lys-Gly-Arg-Phe-Thr-Arg-Gln-Lys-Tyr-Asn-Lys-Arg-Ala [amino acid sequence SEQ ID NO:37], Lys-Leu-Ala-Leu-Lys-Leu-Ala-Leu-Lys-Ala-Leu-Lys-Ala-Ala-Leu-Lys-Leu-Ala [amino acid sequence SEQ ID NO:38], Trp-Glu-Ala-Lys-Leu-Ala-Lys-Ala-Leu-Ala-Lys-Ala-Leu-Ala-Lys-His-Leu-Ala-Lys-Ala-Leu-Ala-Lys-Ala-Leu-Lys-Ala-Cys-Glu-Ala [amino acid sequence SEQ ID NO:39], Arg-Arg-Gln-Arg-Arg-Thr-Ser-Lys-Leu-Met-Lys-Arg [amino acid sequence SEQ ID NO:40] and Val-Asp-Lys-Gly-Ser-Tyr-Leu-Pro-Arg-Pro-Thr(NAcGal)-Pro-Pro-Arg-Pro-Ile-Tyr-Asn-Arg-Asn [amino acid sequence SEQ ID NO:41]. In yet another embodiment, -M- consists of an amino acid or peptide. In yet another embodiment, -M- consists of a single bond.

In one embodiment, $Xaa_1$ is selected from the group consisting of Tyr, Tyr(Me), Tyr(N-Me), Tyr(Me, N-Me), Tyr(I) and Tyr($I_2$). In another embodiment, $Xaa_1$ is selected from the group consisting of Tyr(Me), Tyr(N-Me), Tyr(Me, N-Me), Tyr(I) and Tyr($I_2$). In another embodiment, $Xaa_1$ is Tyr($I_2$). In yet another embodiment, $Xaa_1$ is Tyr(I). In yet another embodiment, $Xaa_1$ is Tyr.

In one embodiment, $Xaa_2$ is Ser or a saccharide-modified serine. In another embodiment, $Xaa_2$ is selected from the group consisting of Ser, Ser(α-Glc), Ser(β-Glc), Ser(α-Gal), Ser(β-Gal), Ser(α-GlcNAc), Ser (β-GlcNAc), Ser(α-GalNAc), Ser(β-GalNAc), Ser(α-Man), Ser(β-Man), Ser(α-ManNAc), Ser(β-ManNAc), Ser(α-[Gal-β(1→4)-Glc)]), Ser(α-[GalNAc-β(1→4)-Glc]), Ser(β-[GalNAc-β(1→4)-Glc]), Ser(β-[GalNAc-β(1→4)-GlcNAc]), Ser(β-[Gal-β(1→4)-Glc]), Ser(β-[Gal-β(1→4)-GlcNAc]), Ser(α-[Glc-α(1→4)-Glc]), Ser(β-[Glc-α(1→4)-Glc]), Ser(β-[Glc-α(1→4)-GlcNAc]), Ser(α-[Glc-β(1→4)-Glc]), Ser(β-[Glc-β(1→4)-Glc]), Ser(β-[Glc-β(1→4)-GlcNAc]), Ser(α-[GlcNAc-β(1→4)-Glc]), Ser(β-[GlcNAc-β(1→4)-Glc]), and Ser(β-[GlcNAc-β(1→4)-Glc]). In another embodiment, $Xaa_2$ is selected from the group consisting of Ser, Ser(α-Glc), Ser(β-

Glc), Ser(α-Gal), Ser(β-Gal), Ser(α-GlcNAc), Ser(β-GlcNAc), Ser(α-GalNAc), and Ser(β-GalNAc). In yet another embodiment, $Xaa_2$ is Ser.

In one embodiment, $Xaa_3$ is Thr or a saccharide-modified threonine. In another embodiment, $Xaa_3$ is selected from the group consisting of Thr, Thr(α-Glc), Thr(β-Glc), Thr(α-Gal), Thr(β-Gal), Thr(α-GlcNAc), Thr(β-GlcNAc), Thr(α-GalNAc), Thr(β-GalNAc), Thr(α-Man), Thr(β-Man), Thr(α-ManNAc), Thr(β-ManNAc), Thr(α-[Gal-β(1→4)-Glc]), Thr(α-[GalNAc-β(1→4)-Glc]), Thr(β-[GalNAc-β(1→4)-Glc]), Thr(β-[GalNAc-β(1→4)-GlcNAc]), Thr(β-[Gal-β(1→4)-Glc]), Thr(β-[Gal-β(1→4)-GlcNAc]), Thr(α-[Glc-α(1→4)-Glc]), Thr(β-[Glc-α(1→4)-Glc]), Thr(β-[Glc-α(1→4)-GlcNAc]), Thr(α [Glc β(1→4)Glc]), Thr(β-[Glc-β(1→4)-Glc]), Thr(β-[Glc-β(1→4)-GlcNAc]), Thr(α-[GlcNAc-β(1→4)Glc]), Thr(β-[GlcNAc-β(1→4)-Glc]), and Thr(β-[GlcNAc-β(1→4)-Glc]). In yet another embodiment, $Xaa_3$ is selected from the group consisting of Thr, Thr(α-Glc), Thr(β-Glc), Thr(α-Gal), Thr(β-Gal), Thr(α-GlcNAc), Thr(β-GlcNAc), Thr(α-GalNAc), and Thr(β-GalNAc), In yet another embodiment, $Xaa_3$ is Thr(α-GalNAc).

In one embodiment, $Xaa_4$ is selected from the group consisting of Arg and Arg(N-Me). In another embodiment, $Xaa_4$ is Arg.

In one embodiment, $Xaa_5$ is a non-natural amino acid. In another embodiment, $Xaa_5$ is selected from the group consisting of the D-isomer of a natural amino acid, arginosuccinic acid, citrulline, cysteine sulfinic acid, 3,4-dihydroxyphenylalanine, homocysteine, homoserine, ornithine, 3-monoiodotyrosine, 3,5-diiodotyrosine, 3,5,5'-triiodothyronine, 3,3',5,5'-tetraiodothyronine, hydroxylysine, 4-hydroxyproline, an N-Cbz-protected amino acid, 2,4-diaminobutyric acid, homoarginine, N-methyl-arginine, norleucine, N-methylaminobutyric acid, naphthylalanine, phenylglycine, beta-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid (also known as Acp or 6-aminohexanoic acid), 6-aminocapramide (also known as $AcpNH_2$ or 6-aminohexanamide), beta-alanine (also known as bAla), $bAlaNH_2$ (also known as 3-aminopropanamide), trans-4-(aminomethyl)-cyclohexanecarboxylic acid, 2-(aminomethyl)-benzoic acid, 3-(aminomethyl)-benzoic acid, 4-(aminomethyl)-benzoic acid, 1-aminocyclopentanecarboxylic acid, 1-aminocyclopropanecarboxylic acid, and 2-benzyl-5-aminopentanoic acid. In yet another embodiment, $Xaa_5$ is selected from the group consisting of bAla (also known as beta-alanine), $bAlaNH_2$ (also known as 3-aminopropanamide), Acp (also known as 6-aminocaproic acid) and $AcpNH_2$ (also known as 6-aminocapramide). In yet another embodiment, $Xaa_5$ is selected from the group consisting of Acp and $AcpNH_2$.

In one embodiment, the compound is selected from the group consisting of Tyr($I_2$)-Ser-Thr(α-GalNAc)-Glu-Val-Val-Ala-Leu-Ser-Arg-Acp [amino acid sequence SEQ ID NO:3], and Tyr($I_2$)-Ser-Thr(α-GalNAc)-Glu-Val-Val-Ala-Leu-Ser-Arg-$AcpNH_2$ [amino acid sequence SEQ ID NO:4], and salts thereof.

The invention also includes a pharmaceutical composition comprising a compound according to Formula (I):

X1-M-SEQ ID NO:2    (I)

or a salt thereof, wherein:
SEQ ID NO:2 represents $Xaa_1$-$Xaa_2$-$Xaa_3$-Glu-Val-Val-Ala-Leu-Ser-$Xaa_4$-$Xaa_5$, wherein:
$Xaa_1$ is Tyr, Tyr(Me), Tyr(N-Me), Tyr(Me, N-Me), Tyr(I) or Tyr($I_2$);
$Xaa_2$ is Ser or a saccharide-modified serine;
$Xaa_3$ is Thr or a saccharide-modified threonine;
$Xaa_4$ is Arg or Arg(N-Me);
$Xaa_5$ is a non-natural amino acid; and,
X1-M represents an optional group comprising a tagging element conjugated to the N-terminus of the amino acid sequence SEQ ID NO:2, wherein:
X1 represents the tagging element, wherein the tagging element is selected from the group consisting of a transduction domain and a detection label; and,
-M- represents a single bond or an optional linking group forming a covalent linkage between the tagging element and the amino acid sequence SEQ ID NO:2;
and a pharmaceutically acceptable carrier.

The invention also includes a method of treating lipodystrophy in a subject in need thereof, wherein the method comprises administering to the subject a therapeutically effective amount of a pharmaceutical formulation comprising a compound of Formula (I):

SEQ ID NO:2 represents $Xaa_1$-$Xaa_2$-$Xaa_3$-Glu-Val-Val-Ala-Leu-Ser-$Xaa_4$-$Xaa_5$, wherein:
$Xaa_1$ is Tyr, Tyr(Me), Tyr(N-Me), Tyr(Me, N-Me), Tyr(I) or Tyr($I_2$);
$Xaa_2$ is Ser or a saccharide-modified serine;
$Xaa_3$ is Thr or a saccharide-modified threonine;
$Xaa_4$ is Arg or Arg(N-Me);
$Xaa_5$ is a non-natural amino acid; and,
X1-M represents an optional group comprising a tagging element conjugated to the N-terminus of the amino acid sequence SEQ ID NO:2, wherein:
X1 represents the tagging element, wherein the tagging element is selected from the group consisting of a transduction domain and a detection label; and,
-M- represents a single bond or an optional linking group forming a covalent linkage between the tagging element and the amino acid sequence SEQ ID NO:2.

The invention also includes a method of treating infertility in a subject in need thereof, wherein the method comprises administering to the subject a therapeutically effective amount of a pharmaceutical formulation comprising a compound of Formula (I):

SEQ ID NO:2 represents $Xaa_1$-$Xaa_2$-$Xaa_3$-Glu-Val-Val-Ala-Leu-Ser-$Xaa_4$-$Xaa_5$, wherein:
$Xaa_1$ is Tyr, Tyr(Me), Tyr(N-Me), Tyr(Me, N-Me), Tyr(I) or Tyr($I_2$);
$Xaa_2$ is Ser or a saccharide-modified serine;
$Xaa_3$ is Thr or a saccharide-modified threonine;
$Xaa_4$ is Arg or Arg(N-Me);
$Xaa_5$ is a non-natural amino acid; and,
X1-M represents an optional group comprising a tagging element conjugated to the N-terminus of the amino acid sequence SEQ ID NO:2, wherein:
X1 represents the tagging element, wherein the tagging element is selected from the group consisting of a transduction domain and a detection label; and,
-M- represents a single bond or an optional linking group forming a covalent linkage between the tagging element and the amino acid sequence SEQ ID NO:2;
wherein the infertility is selected from the group consisting of obesity-related infertility, lipodystrophy-related infertility, and infertility associated with polycystic ovarian syndrome.

The invention also includes a method of treating obesity in a subject in need thereof, wherein the method comprises administering to the subject a therapeutically effective amount of a pharmaceutical formulation comprising a compound of Formula (I):

X1-M-SEQ ID NO:2    (I)

or a salt thereof, wherein:

SEQ ID NO:2 represents $Xaa_1$-$Xaa_2$-$Xaa_3$-Glu-Val-Val-Ala-Leu-Ser-$Xaa_4$-$Xaa_5$, wherein:

$Xaa_1$ is Tyr, Tyr(Me), Tyr(N-Me), Tyr(Me, N-Me), Tyr(I) or Tyr($I_2$);

$Xaa_2$ is Ser or a saccharide-modified serine;

$Xaa_3$ is Thr or a saccharide-modified threonine;

$Xaa_4$ is Arg or Arg(N-Me);

$Xaa_5$ is a non-natural amino acid; and,

X1-M represents an optional group comprising a tagging element conjugated to the N-terminus of the amino acid sequence SEQ ID NO:2, wherein:

X1 represents the tagging element, wherein the tagging element is selected from the group consisting of a transduction domain and a detection label; and, -M- represents a single bond or an optional linking group forming a covalent linkage between the tagging element and the amino acid sequence SEQ ID NO:2.

The invention also comprises a method of treating metabolic syndrome in a subject in need thereof, wherein the method comprises administering to the subject a therapeutically effective amount of a pharmaceutical formulation comprising a compound of Formula (I):

SEQ ID NO:2 represents $Xaa_1$-$Xaa_2$-$Xaa_3$-Glu-Val-Val-Ala-Leu-Ser-$Xaa_4$-$Xaa_5$, wherein:

$Xaa_1$ is Tyr, Tyr(Me), Tyr(N-Me), Tyr(Me, N-Me), Tyr(I) or Tyr($I_2$);

$Xaa_2$ is Ser or a saccharide-modified serine;

$Xaa_3$ is Thr or a saccharide-modified threonine;

$Xaa_4$ is Arg or Arg(N-Me);

$Xaa_5$ is a non-natural amino acid; and,

X1-M represents an optional group comprising a tagging element conjugated to the N-terminus of the amino acid sequence SEQ ID NO:2, wherein:

X1 represents the tagging element, wherein the tagging element is selected from the group consisting of a transduction domain and a detection label; and, -M- represents a single bond or an optional linking group forming a covalent linkage between the tagging element and the amino acid sequence SEQ ID NO:2.

The invention also comprises a method of treating hypothalamic amenorrhea in a subject in need thereof, wherein the method comprises administering to the subject a therapeutically effective amount of a pharmaceutical formulation comprising a compound of Formula (I):

SEQ ID NO:2 represents $Xaa_1$-$Xaa_2$-$Xaa_3$-Glu-Val-Val-Ala-Leu-Ser-$Xaa_4$-$Xaa_5$, wherein:

$Xaa_1$ is Tyr, Tyr(Me), Tyr(N-Me), Tyr(Me, N-Me), Tyr(I) or Tyr($I_2$);

$Xaa_2$ is Ser or a saccharide-modified serine;

$Xaa_3$ is Thr or a saccharide-modified threonine;

$Xaa_4$ is Arg or Arg(N-Me);

$Xaa_5$ is a non-natural amino acid; and,

X1-M represents an optional group comprising a tagging element conjugated to the N-terminus of the amino acid sequence SEQ ID NO:2, wherein:

X1 represents the tagging element, wherein the tagging element is selected from the group consisting of a transduction domain and a detection label; and, -M- represents a single bond or an optional linking group forming a covalent linkage between the tagging element and the amino acid sequence SEQ ID NO:2.

The invention also includes a method of treating diet-induced food craving in a subject in need of such treatment, wherein the method comprises administering to the subject a therapeutically effective amount of a pharmaceutical formulation comprising a compound of Formula (I):

SEQ ID NO:2 represents $Xaa_1$-$Xaa_2$-$Xaa_3$-Glu-Val-Val-Ala-Leu-Ser-$Xaa_4$-$Xaa_5$, wherein:

$Xaa_1$ is Tyr, Tyr(Me), Tyr(N-Me), Tyr(Me, N-Me), Tyr(I) or Tyr($I_2$);

$Xaa_2$ is Ser or a saccharide-modified serine;

$Xaa_3$ is Thr or a saccharide-modified threonine;

$Xaa_4$ is Arg or Arg(N-Me);

$Xaa_5$ is a non-natural amino acid; and,

X1-M represents an optional group comprising a tagging element conjugated to the N-terminus of the amino acid sequence SEQ ID NO:2, wherein:

X1 represents the tagging element, wherein the tagging element is selected from the group consisting of a transduction domain and a detection label; and, -M- represents a single bond or an optional linking group forming a covalent linkage between the tagging element and the amino acid sequence SEQ ID NO:2.

The invention also includes a method of achieving appetite control after bariatric surgery a subject in need thereof, wherein the method comprises administering to the subject a therapeutically effective amount of a pharmaceutical formulation comprising a compound of Formula (I):

SEQ ID NO:2 represents $Xaa_1$-$Xaa_2$-$Xaa_3$-Glu-Val-Val-Ala-Leu-Ser-$Xaa_4$-$Xaa_5$, wherein:

$Xaa_1$ is Tyr, Tyr(Me), Tyr(N-Me), Tyr(Me, N-Me), Tyr(I) or Tyr($I_2$);

$Xaa_2$ is Ser or a saccharide-modified serine;

$Xaa_3$ is Thr or a saccharide-modified threonine;

$Xaa_4$ is Arg or Arg(N-Me);

$Xaa_5$ is a non-natural amino acid; and,

X1-M represents an optional group comprising a tagging element conjugated to the N-terminus of the amino acid sequence SEQ ID NO:2, wherein:

X1 represents the tagging element, wherein the tagging element is selected from the group consisting of a transduction domain and a detection label; and, -M- represents a single bond or an optional linking group forming a covalent linkage between the tagging element and the amino acid sequence SEQ ID NO:2.

The invention also includes a method of maintaining weight during dieting in a subject in need thereof, wherein the method comprises administering to the subject a therapeutically effective amount of a pharmaceutical formulation comprising a compound of Formula (I):

SEQ ID NO:2 represents $Xaa_1$-$Xaa_2$-$Xaa_3$-Glu-Val-Val-Ala-Leu-Ser-$Xaa_4$-$Xaa_5$, wherein:

$Xaa_1$ is Tyr, Tyr(Me), Tyr(N-Me), Tyr(Me, N-Me), Tyr(I) or Tyr($I_2$);

$Xaa_2$ is Ser or a saccharide-modified serine;

$Xaa_3$ is Thr or a saccharide-modified threonine;

$Xaa_4$ is Arg or Arg(N-Me);

$Xaa_5$ is a non-natural amino acid; and,

X1-M represents an optional group comprising a tagging element conjugated to the N-terminus of the amino acid sequence SEQ ID NO:2, wherein:

X1 represents the tagging element, wherein the tagging element is selected from the group consisting of a transduction domain and a detection label; and, -M- represents a single bond or an optional linking group forming a covalent linkage between the tagging element and the amino acid sequence SEQ ID NO:2.

The invention also includes a method of treating insulin resistance in a subject in need thereof, wherein the method comprises administering to the subject a therapeutically effective amount of a pharmaceutical formulation comprising a compound of Formula (I):

SEQ ID NO:2 represents $Xaa_1$-$Xaa_2$-$Xaa_3$-Glu-Val-Val-Ala-Leu-Ser-$Xaa_4$-$Xaa_5$, wherein:
- $Xaa_1$ is Tyr, Tyr(Me), Tyr(N-Me), Tyr(Me, N-Me), Tyr(I) or Tyr($I_2$);
- $Xaa_2$ is Ser or a saccharide-modified serine;
- $Xaa_3$ is Thr or a saccharide-modified threonine;
- $Xaa_4$ is Arg or Arg(N-Me);
- $Xaa_5$ is a non-natural amino acid; and,
- X1-M represents an optional group comprising a tagging element conjugated to the N-terminus of the amino acid sequence SEQ ID NO:2, wherein:
  - X1 represents the tagging element, wherein the tagging element is selected from the group consisting of a transduction domain and a detection label; and,
  - -M- represents a single bond or an optional linking group forming a covalent linkage between the tagging element and the amino acid sequence SEQ ID NO:2.

The invention also includes a method of treating type II diabetes in a subject in need thereof, wherein the method comprises administering to the subject a therapeutically effective amount of a pharmaceutical formulation comprising a compound of Formula (I):

SEQ ID NO:2 represents $Xaa_1$-$Xaa_2$-$Xaa_3$-Glu-Val-Val-Ala-Leu-Ser-$Xaa_4$-$Xaa_5$, wherein:
- $Xaa_1$ is Tyr, Tyr(Me), Tyr(N-Me), Tyr(Me, N-Me), Tyr(I) or Tyr($I_2$);
- $Xaa_2$ is Ser or a saccharide-modified serine;
- $Xaa_3$ is Thr or a saccharide-modified threonine;
- $Xaa_4$ is Arg or Arg(N-Me);
- $Xaa_5$ is a non-natural amino acid; and,
- X1-M represents an optional group comprising a tagging element conjugated to the N-terminus of the amino acid sequence SEQ ID NO:2, wherein:
  - X1 represents the tagging element, wherein the tagging element is selected from the group consisting of a transduction domain and a detection label; and,
  - -M- represents a single bond or an optional linking group forming a covalent linkage between the tagging element and the amino acid sequence SEQ ID NO:2.

The invention also includes a method of improving cognitive functions in a subject in need thereof, wherein the method comprises administering to the subject a therapeutically effective amount of a pharmaceutical formulation comprising a compound of Formula (I):

SEQ ID NO:2 represents $Xaa_1$-$Xaa_2$-$Xaa_3$-Glu-Val-Val-Ala-Leu-Ser-$Xaa_4$-$Xaa_5$, wherein:
- $Xaa_1$ is Tyr, Tyr(Me), Tyr(N-Me), Tyr(Me, N-Me), Tyr(I) or Tyr($I_2$);
- $Xaa_2$ is Ser or a saccharide-modified serine;
- $Xaa_3$ is Thr or a saccharide-modified threonine;
- $Xaa_4$ is Arg or Arg(N-Me);
- $Xaa_5$ is a non-natural amino acid; and,
- X1-M represents an optional group comprising a tagging element conjugated to the N-terminus of the amino acid sequence SEQ ID NO:2, wherein:
  - X1 represents the tagging element, wherein the tagging element is selected from the group consisting of a transduction domain and a detection label; and,
  - -M- represents a single bond or an optional linking group forming a covalent linkage between the tagging element and the amino acid sequence SEQ ID NO:2.

In one embodiment of the invention, the invention includes a compound of Formula (I), or salt thereof; for use in treating lipodystrophy in a patient in need thereof.

In another embodiment of the invention, the invention includes a compound of Formula (I), or salt thereof; for use in treating infertility in a patient in need thereof.

In yet another embodiment of the invention, the invention includes a compound of Formula (I), or salt thereof; for use in treating obesity in a patient in need thereof.

In yet another embodiment of the invention, the invention includes a compound of Formula (I), or salt thereof; for use in treating metabolic syndrome in a patient in need thereof.

In yet another embodiment of the invention, the invention includes a compound of Formula (I), or salt thereof; for use in treating hypothalamic amenorrhea in a patient in need thereof.

In yet another embodiment of the invention, the invention includes a compound of Formula (I), or salt thereof, for use in treating diet-induced food craving in a patient in need thereof.

In yet another embodiment of the invention, the invention includes a compound of Formula (I), or salt thereof; for use in maintaining weight during dieting in a patient in need thereof.

In yet another embodiment of the invention, the invention includes a compound of Formula (I), or salt thereof; for use in treating insulin resistance in a patient in need thereof.

In yet another embodiment of the invention, the invention includes a compound of Formula (I), or salt thereof, for use in improving cognitive functions in a patient in need thereof.

In yet another embodiment of the invention, the invention includes a compound of Formula (I), or salt thereof, for use in achieving appetite control after bariatric surgery in a patient in need thereof.

In yet another embodiment of the invention, the invention includes a compound of Formula (I), or salt thereof, for use in treating type II diabetes in a patient in need thereof.

As envisioned in the present invention with respect to the disclosed compositions of matter and methods, in one aspect the embodiments of the invention comprise the components and/or steps disclosed therein. In another aspect, the embodiments of the invention consist essentially of the components and/or steps disclosed therein. In yet another aspect, the embodiments of the invention consist of the components and/or steps disclosed therein.

DESCRIPTION OF FIGURES

Embodiments of the present invention will now be described, by way of example only, with reference to the attached Figures.

FIG. 4 illustrates weight loss in mice treated with Compound (1).

DEFINITIONS

Figure 1:
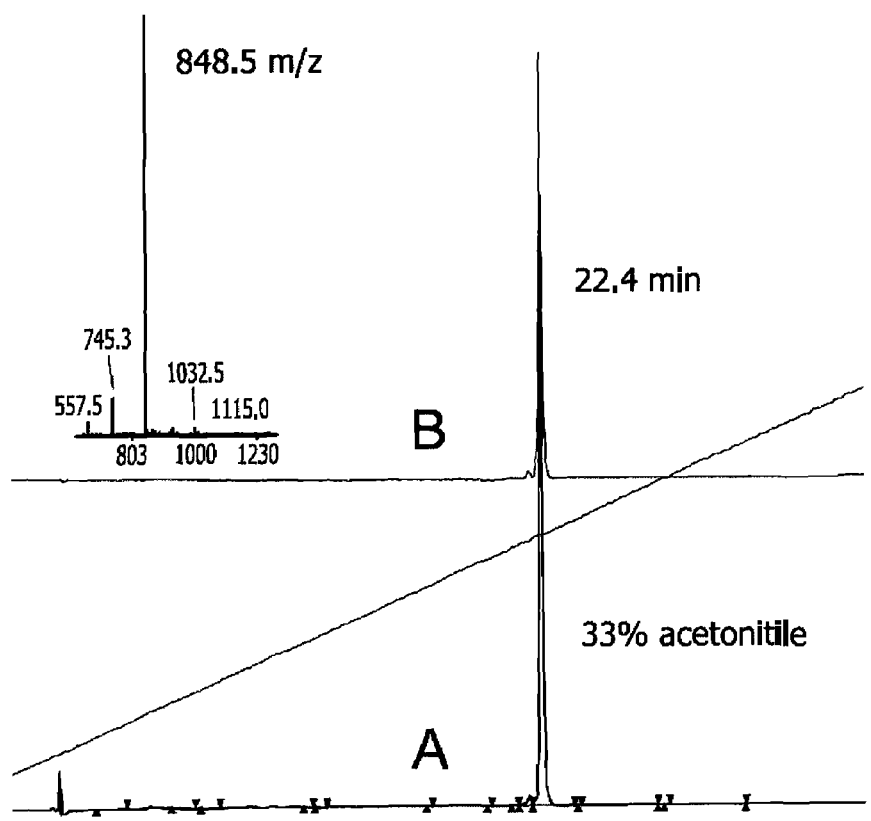
FIG. 1 illustrates the analytical HPLC trace for compound (1) [Tyr($I_2$)-Ser-Thr(α-GalNAc)-Glu-Val-Val-Ala-Leu-Ser-Arg-AcpNH$_2$]. Absorption was monitored at 220 nm and 280 nm. The ES-MS mass spectrum of the single HPLC peak is shown in the inset.

The definitions used in this application are for illustrative purposes and do not limit the scope used in the practice of the invention.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, protein chemistry and nucleic acid chemistry and hybridization are those well known and commonly employed in the art.

As used in the specification and the appended claims, the singular forms "a," "an" and "the" include plural referents unless the context clearly dictates otherwise.

The term "about" will be understood by persons of ordinary skill in the art and will vary to some extent on the context in which it is used.

As used herein, the terms "peptide," "polypeptide," or "protein" are used interchangeably, and refer to a compound comprised of amino acid residues covalently linked by peptide bonds. A protein or peptide must contain at least two amino acids, and no limitation is placed on the maximum number of amino acids that may comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs and fusion proteins, among others. The polypeptides include natural peptides, recombinant peptides, synthetic peptides or a combination thereof. A peptide that is not cyclic will have an N-terminus and a C-terminus. The N-terminus will have an amino group, which may be free (i.e., as a $NH_2$ group) or appropriately protected (for example, with a BOC or a Fmoc group). The C-terminus will have a carboxylic group, which may be free (i.e., as a COOH group) or appropriately protected (for example, as a benzyl or a methyl ester). A cyclic peptide does not necessarily have free N- or C-termini, since they are covalently bonded through an amide bond to form the cyclic structure. The term "peptide bond" means a covalent amide linkage formed by loss of a molecule of water between the carboxyl group of one amino acid and the amino group of a second amino acid.

As used herein, the term "fragment," as applied to a protein or peptide, refers to a subsequence of a larger protein or peptide. A "fragment" of a protein or peptide can be at least about 10 amino acids in length; for example, at least about 50 amino acids in length; more preferably, at least about 100 amino acids in length; even more preferably, at least about 200 amino acids in length; particularly preferably, at least about 300 amino acids in length; and most preferably, at least about 400 amino acids in length.

As used herein, the term "resists exopeptidase activity" refers to the property of a peptide-based compound to resist proteolytic degradation by an exopeptidase. Exopeptidases are proteolytic enzymes that typically remove an N-terminal or a C-terminal amino acid residue from a peptide or protein through hydrolysis. A peptide or protein may be designed, modified, recombinantly prepared, or synthetically prepared to resist degradation by exopeptidases. A peptide is said to "resist exopeptidase activity" according to the invention when a C-terminal or N-terminal amino acid residue is cleaved from such a peptide more slowly than from an otherwise identical peptide that was not modified or designed to resist such exopeptidase activity. A peptide is also said to "resist exopeptidase activity" according to the invention when a C-terminal or N-terminal amino acid residue is not at all cleaved from such a peptide than from an otherwise identical peptide that was not modified or designed to resist such exopeptidase activity.

As used herein, amino acids are represented by the full name thereof, by the three-letter code, as well as the one-letter code corresponding thereto. The structure of amino acids and their abbreviations can be found in the chemical literature, such as in Stryer, 1988, "Biochemistry", 3rd Ed., W. H. Freeman & Co., NY, N.Y. Table 1 summarizes the natural alpha-amino acids and their corresponding representations.

TABLE 1

Natural alpha-amino acids and abbreviations.

| Full Name | Three-Letter Code | One-Letter Code | Full Name | Three-Letter Code | One-Letter Code |
|---|---|---|---|---|---|
| Alanine | Ala | A | Leucine | Leu | L |
| Arginine | Arg | R | Lysine | Lys | K |
| Asparagine | Asn | N | Methionine | Met | M |
| Aspartic Acid | Asp | D | Phenylalanine | Phe | F |
| Cysteine | Cys | C | Proline | Pro | P |
| Cystine | Cys-Cys | C-C | Serine | Ser | S |
| Glutamic Acid | Glu | E | Threonine | Thr | T |
| Glutamine | Gln | Q | Tryptophan | Trp | W |
| Glycine | Gly | G | Tyrosine | Tyr | Y |
| Histidine | His | H | Valine | Val | V |
| Isoleucine | Ile | I | | | |

An "acetylated amino acid" as used herein refers to an amino acid or saccharide-modified amino acid having an acetyl moiety in its side chain. Arg(N-Me) is 5-guanidino-2-(methylamino)pentanoic acid (wherein the backbone amino group of arginine is monomethylated). Tyr(Me) is 2-amino-3-(4-methoxyphenyl)propanoic acid (wherein the phenol hydroxyl group in tyrosine is methylated). Tyr(N-Me) is 3-(4-hydroxyphenyl)-2-(methylamino)propanoic acid (wherein the backbone amino group of tyrosine is monomethylated). Tyr(Me, N-Me) is 3-(4-methoxyphenyl)-2-(methylamino) propanoic acid (wherein both the phenol hydroxyl and the backbone amino groups in tyrosine are methylated).

As used herein, the term "non-natural amino acid" corresponds to an amino acid that is not the L-isomer of one of the natural alpha-amino acids listed in Table 1. Non-natural amino acids include, but are not limited to, the D-isomer of a natural amino acid, arginosuccinic acid, citrulline, cysteine sulfinic acid, 3,4-dihydroxyphenylalanine, homocysteine, homoserine, ornithine, 3-monoiodotyrosine (also known as Tyr(I)), 3,5-diiodotyrosine (also known as Tyr($I_2$)), 3,5,5'-triiodothyronine, 3,3',5,5'-tetraiodothyronine, hydroxylysine, 4-hydroxyproline, an N-Cbz-protected amino acid, 2,4-diaminobutyric acid, homoarginine, N-methyl-arginine, norleucine, N-methylaminobutyric acid, naphthylalanine, phenylglycine, beta-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid (also known as Acp or 6-aminohexanoic acid), 6-aminocapramide (also known as $AcpNH_2$ or 6-aminohexanamide), beta-alanine (also known as bAla), $bAlaNH_2$ (also known as 3-aminopropanamide), trans-4-(aminomethyl)-cyclohexanecarboxylic acid, 2-(aminomethyl)-benzoic acid, 3-(aminomethyl)-benzoic acid, 4-(aminomethyl)-benzoic acid, 1-aminocyclopentanecarboxylic acid, 1-aminocyclopropanecarboxylic acid, and 2-benzyl-5-aminopentanoic acid. Preferentially, the non-natural amino acid is selected from the group consisting of Acp, $AcpNH_2$, bAla and $bAlaNH_2$.

As used herein, the term "saccharide" refers to sugars of any identity and any length. The term "saccharide" therefore encompasses a monosaccharide, a disaccharide, and a trisaccharide, as well as oligosaccharides and polysaccharides in general. Preferentially, the saccharide is a monosaccharide or a disaccharide. The term saccharide also refers to glucose, fructose, galactose, mannose, N-acetylgalactosamine, and N-acetylglucosamine, among other sugars.

As used herein, Gal corresponds to galactose, Glc corresponds to glucose, and Man corresponds to mannose. α-Gal corresponds to alpha-galactose, β-Gal corresponds to beta-galactose, α-Glc corresponds to alpha-glucose, β-Glc corresponds to beta-glucose, α-Man corresponds to alpha-mannose, β-Man corresponds to beta-mannose, GalNAc corresponds to N-acetyl galactosamine, GlcNAc corresponds to N-acetyl glucosamine, and ManNAc corresponds to N-acetyl mannosamine.

As used herein, Thr(α-GalNAc) corresponds to threonine glycosylated on the alcohol hydroxyl group with an N-acetyl galactosyl residue via an alpha linkage. Thr(α-$GalNAc_4$) corresponds to threonine glycosylated on the alcohol hydroxyl group with an N-acetyl galactosyl residue via an alpha linkage, wherein the hydroxyl groups at the 2-, 4- and 6-positions of the sugar ring are acetylated as well. Thr(β-GalNAc) corresponds to threonine glycosylated on the alcohol hydroxyl group with an N-acetyl galactosyl residue via a beta linkage. Thr(α-[GlcNAc-β(1→4)-Glc]) corresponds to threonine glycosylated on the alcohol hydroxyl group with a disaccharide, wherein a β-N-acetyl glucosyl residue is attached by a β linkage to the 4-position of a glucosyl residue, and the glucosyl residue is attached by an α linkage to the threonine alcohol group. This nomenclature may be easily extended to other glycosylated amino acids of the invention.

As used herein, the term "saccharide-modified amino acid" refers to an amino acid that has a saccharide moiety covalently linked thereto. For an amino acid within a peptide, the saccharide is linked to the side chain of the amino acid. As used herein, the term "saccharide-modified hydroxyamino acid" as used herein refers to a hydroxyamino acid that has a saccharide moiety covalently linked thereto. Preferentially, the hydroxyamino acid in a saccharide-modified hydroxyamino acid is serine or threonine. The term "saccharide-modified serine" as used herein refers to a serine that has a saccharide moiety covalently linked to the side chain primary alcohol group. Non-limiting examples of saccharide-modified serines are Ser(α-Glc), Ser(β-Glc), Ser(α-Gal), Ser (β-Gal), Ser(α-GlcNAc), Ser (β-GlcNAc), Ser(α-GalNAc), Ser(β-GalNAc), Ser(α-Man), Ser(β-Man), Ser(α-ManNAc), and Ser(β-ManNAc). The term "saccharide-modified threonine" as used herein refers to a threonine that has a saccharide moiety covalently linked to the side chain secondary alcohol group. Non-limiting examples of saccharide-modified threonines are Thr(α-Glc), Thr(β-Glc), Thr(α-Gal), Thr(β-Gal), Thr(α-GlcNAc), Thr(β-GlcNAc), Thr(α-GalNAc), Thr(β-GalNAc), Thr(α-Man), Thr(b-Man), Thr(α-ManNAc), and Thr(b-ManNAc).

As used herein, the term "ObR" refers to a leptin receptor, also known as LEPR and CD295 (amino acid sequence SEQ ID NO:42; cluster of differentiation 295). The human transmembrane receptor has at least four different isoforms with different C-terminus cytoplasmatic domains (Barr et al., 1999, J. Biol. Chem. 274 (30): 21416-21424). The full form of ObR (ObR1) is 1,165 amino acids long and contains extracellular, transmembrane and intracellular domains. The extracellular domain binds ligand, whereas the intracellular tail recruits and activates signaling substrates. ObR1 has full signaling potential, as opposed to the shorter ObR isoforms.

As used herein, the term "leptin receptor-positive cell" refers to a cell that expresses on its surface an isoform of the leptin receptor, which is able to bind leptin or any leptin receptor binder.

As used herein, the term "translocation domain" refers to a peptide, or derivative thereof, that is capable of crossing cell membranes and of directing the transport of a peptide, protein, or molecule associated with the protein transduction domain, from the outside of a cell into the cytoplasm of the cell through the cytoplasmic membrane of the cell.

As used herein, the term "detection label" refers to a chemical moiety that, once attached to a peptide of the invention, allows for the detection and/or quantitation of the peptide based on an intrinsic and detectable property of the moiety. Non-limiting examples of intrinsic and detectable property within the invention are fluorescence, radioactivity, emission of radiowaves, and magnetism. The preferred example of intrinsic and detectable property within the invention is fluorescence.

As used herein, the term "conjugated" referring to the linking of two molecules means that the two molecules are covalently linked to one another through the formation of an amide bond between the carboxyl group of one of the molecules and an amino group of the other molecule, or by means of a linking group wherein the linking group has covalent bonds to each of the molecules. For example, the linking group may be a peptide chain, an amino acid, or any group having at least two functional groups and capable of forming covalent bond to each of the two molecules.

As used herein, the term "obesity" is defined as excess body mass. The World Health Organization (WHO) classifies body mass (Kopelman, 2000, Nature 404: 635-643) according body mass index (BMI, weight kg/height $m^2$) as follows:

BMI less than 18.5, underweight; BMI of 18.5-24.9, normal; BMI of 25.0-29.9, overweight (grade 1); BMI of 30-39.9, obese (grade 2); and BMI equal to or greater than 40, morbidly obese (grade 3). As used herein, "obesity" refers to both obesity and morbid obesity as defined by the WHO.

Waist circumference may also be used to indicate a risk of metabolic complications: in men a circumference of greater than or equal to 94 cm indicates an increased risk, and greater than or equal to 102 cm indicates a substantially increased risk. Similarly, in women a circumference greater than or equal to 88 cm indicates an increased risk, and greater than or equal to 90 cm indicates a substantially increased risk. The waist circumference is measured in cm at midpoint between lower border of ribs and upper border of the pelvis. Other measures of obesity include, but are not limited to, "skinfold thickness," which is a measurement in centimeters of skinfold thickness using calipers, and "bioimpedance", which is based on the principle that lean mass, which is primarily an electrolyte solution, conducts current better than fat mass. Measurement of resistance to a weak current (impedance) applied across extremities provides an estimate of body fat using an empirically derived equation.

As used herein, the term "lipodystrophy" refers to a disorder in the way in which a body uses, produces and stores fat.

As used herein, the terms "weight maintenance during dieting" and "diet-induced food craving" refer to a condition when patients on low calorie diet suffer from low leptin levels leading to impulse bingeing.

As used herein, the term "obesity-related infertility" refers to infertility associated with obesity in a female or a male.

As used herein, "isolated" means altered or removed from the natural state through the actions of a human being. For example, a nucleic acid or a peptide naturally present in a living animal is not "isolated," but the same nucleic acid or peptide partially or completely separated from the coexisting materials of its natural state is "isolated." An isolated nucleic acid or protein may exist in substantially purified form, or may exist in a non-native environment, such as a host cell for example.

"Biologically active," as used herein with respect to a peptide of the invention, means that the peptide of the invention have the ability to bind and act as an agonist to a leptin receptor.

The term "inhibit," as used herein, means to suppress or block an activity or function by at least about ten percent relative to a control value. Preferably, the activity is suppressed or blocked by 50% compared to a control value, more preferably by 75%, and even more preferably by 95%.

"Treating", as used herein, means ameliorating the effects of, or delaying, halting or reversing the progress of a disease or disorder. The word encompasses reducing the severity of a symptom of a disease or disorder and/or the frequency of a symptom of a disease or disorder.

"Medical intervention", as used herein, means a set of one or more medical procedures or treatments that are required for ameliorating the effects of, delaying, halting or reversing a disease or disorder of a subject. A medical intervention may involve surgical procedures or not, depending on the disease or disorder in question. A medical intervention may be wholly or partially performed by a medical specialist, or may be wholly or partially performed by the subject himself or herself, if capable, under the supervision of a medical specialist or according to literature or protocols provided by the medical specialist.

A "subject", as used therein, may be a human or non-human animal. Non-human animals include, for example, livestock and pets, such as ovine, bovine, porcine, canine, feline and murine mammals, as well as reptiles, birds and fish. Preferably, the subject is human.

The language "effective amount" or "therapeutically effective amount" refers to a nontoxic but sufficient amount of the composition used in the practice of the invention that is effective to treat obesity in a subject, or is effective to treat a nutrition-related metabolic disorder in a subject, or is effective to treat a metabolic disorder in a subject. The desired treatment may be prophylactic and/or therapeutic. That result can be reduction and/or alleviation of the signs, symptoms, or causes of a disease or disorder, or any other desired alteration of a biological system. An appropriate therapeutic amount in any individual case may be determined by one of ordinary skill in the art using routine experimentation.

As used herein, a "prophylactic" or "preventive" treatment is a treatment administered to a subject who does not exhibit signs of a disease or disorder, or exhibits only early signs of the disease or disorder, for the purpose of decreasing the risk of developing pathology associated with the disease or disorder.

As used herein, a "therapeutic" treatment is a treatment administered to a subject who exhibits signs of pathology of a disease or disorder for the purpose of diminishing or eliminating those signs.

A "pharmaceutically acceptable carrier" refers herein to a composition suitable for delivering an active pharmaceutical ingredient, such as a compound of the present invention, to a subject without excessive toxicity or other complications while maintaining the biological activity of the active pharmaceutical ingredient. Protein-stabilizing excipients, such as mannitol, sucrose, polysorbate-80 and phosphate buffers, are typically found in such carriers, although the carriers should not be construed as being limited only to these compounds.

As used herein with respect to formulations, the term "additional ingredients" includes, but is not limited to, one or more of the following: excipients, surface active agents, dispersing agents, inert diluents, granulating and disintegrating agents, binding agents, lubricating agents, sweetening agents, flavoring agents, coloring agents, preservatives, physiologically degradable compositions such as gelatin, aqueous vehicles and solvents, oily vehicles and solvents, suspending agents, dispersing or wetting agents, emulsifying agents, demulcents, buffers, salts, thickening agents, fillers, emulsifying agents, antioxidants, antibiotics, antifungal agents, stabilizing agents and pharmaceutically acceptable polymeric or hydrophobic materials. Other "additional ingredients" that may be included in the pharmaceutical compositions used in the practice of the invention are known in the art and described, for example in Remington's Pharmaceutical Sciences (Genaro, ed. Mack Publishing Co., 1985, Easton, Pa.), the disclosure of which is incorporated herein by reference.

As used herein, the term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions can contain information pertaining to the compound's ability to perform its intended function, e.g., treating obesity in a subject.

As used herein, the term "applicator" is used to identify any device including, but not limited to, a hypodermic syringe, a pipette, and the like, for administering the compounds and compositions used in the practice of the invention.

DETAILED DESCRIPTION OF THE INVENTION

The present invention is based on the unexpected discovery that certain leptin-based peptides act as agonists of the leptin receptor (ObR) with minimal antagonist activity, and thus may be considered "full agonists" of the leptin receptor. In one aspect, they stimulate the growth of ObR-positive cells (agonistic effect) at lower concentrations than the native ligand when added alone, and do not antagonize the actions of leptin (antagonistic effect) in the same cells. In another aspect, they have a more extended duration of action than the native leptin. The concentrations at which antagonistic effects may be observed are at least 100 times higher than those at which agonistic effects are observed. Therefore, the compounds of the invention have an agonist:antagonist selectivity ratio equal to or greater than about 100. The peptides of the invention may find use in treating or preventing the development of obesity, as well as metabolic diseases, such as lipodystrophy, obesity-related infertility, metabolic syndrome, hypothalamic amenorrhea, diet-induced food craving, type II diabetes, appetite control after bariatric surgery, and insulin resistance.

Compounds of the Invention

As one aspect of the invention, there is provided a compound according to Formula (I):

$$X^1\text{-M-SEQ ID NO:2} \quad (I)$$

or a salt thereof, wherein:
SEQ ID NO:2 represents $Xaa_1$-$Xaa_2$-$Xaa_3$-Glu-Val-Val-Ala-Leu-Ser-$Xaa_4$-$Xaa_5$, wherein:
   $Xaa_1$ is Tyr, Tyr(Me), Tyr(N-Me), Tyr(Me, N-Me), Tyr(I) or Tyr($I_2$);
   $Xaa_2$ is Ser or a saccharide-modified serine;
   $Xaa_3$ is Thr or a saccharide-modified threonine;
   $Xaa_4$ is Arg or Arg(N-Me);
   $Xaa_5$ is a non-natural amino acid; and,
   X1-M represents an optional group comprising a tagging element conjugated to the N-terminus of the amino acid sequence SEQ ID NO:2, wherein:
      X1 represents the tagging element, wherein the tagging element is selected from the group consisting of a transduction domain and a detection label; and,
      -M- represents a single bond or an optional linking group forming a covalent linkage between the tagging element and the amino acid sequence SEQ ID NO:2.

In a preferred embodiment, the compound of the invention is the peptide of amino acid sequence Tyr($I_2$)-Ser-Thr(α-GalNAc)-Glu-Val-Val-Ala-Leu-Ser-Arg-Acp [amino acid sequence SEQ ID NO:3], or a salt thereof. In another preferred embodiment, the compound of the invention is the peptide of amino acid sequence Tyr($I_2$)-Ser-Thr(α-GalNAc)-Glu-Val-Val-Ala-Leu-Ser-Arg-AcpNH$_2$ [amino acid sequence SEQ ID NO:4], or a salt thereof.

When it is stated that "$X^1$-M- represents an optional group", it is meant that Formula (I) is intended to encompass both a compound of the formula $X^1$-M-SEQ ID NO:2 or a salt thereof, where the amino acid sequence SEQ ID NO:2 is conjugated to a tagging element, as well as the peptide consisting of the amino acid sequence SEQ ID NO:2 or a salt thereof, which is not conjugated to a tagging element.

Synthesis of the Compounds of the Invention

The compounds of the invention may be prepared by methods known to the person skilled in the art of peptide and organic synthesis. Peptides of the present invention may be natural peptides, recombinant peptides or synthetic peptides. They may also be chemically synthesized, using, for example, solid phase synthesis methods. Transduction domains or detection labels appended to peptides of the invention may be natural or synthetic peptides, may be non-peptidic moieties, and may be either prepared by isolation from natural sources or may be synthesized.

The peptides of the present invention may be synthesized de novo using peptide synthesis methods. In such methods, the peptide chain is prepared by a series of coupling reactions in which the constituent amino acids are added to the growing peptide chain in the desired sequence. The use of various N-protecting groups, e.g., the carbobenzoxy (CBZ) group or the t-butoxycarbonyl (tBoc) group; various coupling reagents e.g., dicyclohexylcarbodiimide (DCC) or carbonyldiimidazole (CDI); various active esters, e.g., esters of N-hydroxyphthalimide or N-hydroxy-succinimide; and the various cleavage reagents, e.g., trifluoroacetic acid (TFA), HCl in dioxane, boron tris(trifluoroacetate) and cyanogen bromide; and reaction in solution with isolation and purification of intermediates are methods well-known to those of ordinary skill in the art. The reaction may be carried out with the peptide either in solution or attached to a solid-phase support. In the solid phase method, the peptide is released from the solid-phase support following completion of the synthesis.

In an embodiment, peptide synthesis method may follow Merrifield solid-phase procedures. See Merrifield, 1963, J. Am. Chem. Soc. 85: 2149-54 and Merrifield, 1965, Science 50: 178-85. Additional information about the solid-phase synthetic procedure can be obtained from the treatises: Atherton & Sheppard, 1989, "Solid Phase Peptide Synthesis: A Practical Approach", Oxford University Press, NY, N.Y.; Stewart & Young, 1984, "Solid phase peptide synthesis", 2nd edition, Pierce Chemical Company, Rockford, Ill.; and the review chapters by R. Merrifield, 1969, Adv. Enzymol. 32: 221-296, and by B. W. Erickson and R. Merrifield, 1976, in "The Proteins", Vol. 2, pp. 255 et seq., edited by Neurath and Hill, Academic Press, NYC, N.Y. Peptide synthesis may follow synthetic techniques such as those set forth in Fields et al., 2008, "Introduction to Peptide Synthesis", in "Current Protocols in Molecular Biology", Chapter 11, Unit 11.15, John Wiley and Sons, Hoboken, N.J., and Amblard et al., 2006, Molecular Biotechnology 33: 239-254.

The synthesis of peptides by solution methods is described in "The Proteins", 3rd Edition, Vol. 11, Neurath et al., Eds., Academic Press, St. Louis, Mo., 1976. Other general references to the synthesis of peptides include: "Peptide Synthesis Protocols", 1994, edited by M. W. Pennington and Ben M. Dunn, Humana Press, Totowa, N.J.; Bodanszky, 1993, "Principles of Peptide Synthesis", 2nd edition, Springer-Verlag, NYC, N.Y.; Lloyd-Williams et al., 1997, "Chemical Approaches to the Synthesis of Peptides and Proteins", CRC Press, Boca Raton, Fla.; and "Synthetic Peptides: A User's Guide", G. Grant, Ed., Oxford University Press, NY, N.Y., 2002.

Peptides of the invention may be modified by addition of O-linked saccharides. O-linked saccharides are linked primarily to hydroxyamino acid side chains, such as those found in serine and threonine. For a review of O-linked saccharides, see Schachter and Brockhausen, 1989, "The Biosynthesis of Branched O-Linked Glycans", Society for Experimental Biology, pp. 1-26 (Great Britain); Takeda et al., 1995, Trends Biochem. Sci. 20: 367-371; and Udenfriend et al., 1995, Ann. Rev. Biochem. 64: 593-591.

In one aspect, peptides having O-linked saccharides may be prepared using in vitro or in vivo enzymatic techniques. For example, peptides having O-linked saccharides may be formed by the stepwise addition of sugars from nucleotide sugars (Tanner et al., 1987, Biochim. Biophys. Acta. 906: 81-91; and Hounsell et al., 1996, Glycoconj. J. 13: 19-26). In another aspect, peptides having O-linked saccharides may be prepared using chemical synthetic methods, such as solid-phase synthesis or liquid-phase synthesis A variety of methods are known in the art to customize the glycosylation pattern of a peptide, including those described in Urge et al., 1991, Tetrahedron Lett. 32: 3445-3448, Cudic et al., 2002, Bioorg. Med. Chem. 10: 3859-3870, PCT Applications Nos. WO 99/22764, WO 98/58964, and WO 99/54342; and U.S. Pat. Nos. 5,047,335 and 7,276,475, among others. For enzymatic techniques, many of the enzymes required for the in vitro addition of saccharide moieties to peptides have been cloned and sequenced. In some instances, these enzymes have been used in vitro to add specific saccharides to the side chain of an amino acid within a peptide. In other instances, cells have been genetically engineered to express a combination of enzymes and desired peptides, such that addition of a desired saccharide moiety to an expressed peptide occurs within the cell.

Compounds of Formula (I) wherein the linker -M- is other than a peptide chain may be prepared, for example, by coupling the tagging element and the suitable linking molecule using methods that will vary according to the exact nature of the compound but will be apparent to the person skilled in the art. Suitable protecting group strategies may be employed in order to achieve the desired selectivity of the site of coupling, as described, for example, in "Protective Groups in Organic Synthesis", by Greene & Wuts (3rd Edition, Wiley, 1999).

Linking Groups and Tagging Elements

The compounds of the invention may have the ability to cross the blood brain barrier, depending on their intrinsic properties. Determination of ability of the compounds of the invention to penetrate the blood brain barrier may be easily performed using standard techniques such as those cited in Bernacki et al., 2008, Pharmacol. Rep. 60 (5): 600-22.

The ability of the compound of the invention to cross the blood brain barrier may be enhanced when it comprises a transduction domain as the tagging element (X1). The transduction domain improves the ability of the construct to cross the cell membrane (see PCT Application No. WO 2008/070049, the entire disclosure of which is incorporated by reference herein). Such transduction domain may be a peptide selected for its known membrane-crossing properties.

The compounds of the invention may also benefit from the property of being easily monitored or detected in vitro or in vivo. In vitro, the monitoring or detection of the compounds of the invention would allow one skilled in the art to identify whether and/or which cells under observation contain leptin receptors, and to follow the binding of the compounds of the invention to such leptin receptor-positive cells. In vivo, the monitoring or detection of the compounds of the invention would allow one skilled in the art to determine whether/or which the tissues under observation contain leptin-receptor positive cells and to evaluate the biodistribution of the peptides dose in an individual. The ability of detecting a compound of the invention, in either an unbound or a bound form, may be enhanced when the compound of the invention comprises a detection label as the tagging element (X1). In this case, cells that present leptin receptors on their surfaces may bind the peptide of the invention and the detection label may be used to monitor the binding or identify the position of the leptin receptor-containing cells. The method used to monitor such phenomena is dependent on the specific nature of the detection label. In the case that the detection label is a fluorescent label, fluorescent detection would be favored.

In the case where the peptide of amino acid sequence SEQ ID NO:2 is conjugated to a tagging element, the link between the peptide of amino acid sequence SEQ ID NO:2 and the tagging element is formed via a single bond or an optional linking group (the link is represented by -M-). Since the purpose of the linking group is merely to covalently join the tagging element and the peptide of amino acid sequence SEQ ID NO:2, the person skilled in the art will be able to use a large number of ways in which to achieve such linkage. In essence, the linking group may be any moiety that is at least bifunctional, provided that the resulting link between the tagging element and the peptide of amino acid sequence SEQ ID NO:2 is stable. Suitable linking moieties include bi- and multi-functional alkyl, aryl, aralkyl or peptidic moieties, alkyl, aryl or aralkyl aldehydes acids esters and anhydrides, sulfhydryl or carboxyl groups, such as maleimido benzoic acid derivatives, maleimido propionic acid derivatives and succinimido derivatives, or may be derived from cyanuric bromide or chloride, carbonyldiimidazole, succinimidyl esters or sulphonic halides and the like (U.S. Pat. No. 6,472,507, the entire disclosure of which is incorporated herein by reference). The functional groups on the linker moiety may include amino, hydrazino, hydroxyl, thiol, maleimido, carbonyl, and carboxyl groups. Optionally the linker group is selected so as to be sufficiently labile (e.g., to undergo enzymatic cleavage by an enzyme present in the targeted tissue) so that it is cleaved following achievement of the intended function of the working element (such as, in the case where the tagging element is a transduction domain, transport of the peptide of the amino acid sequence SEQ ID NO:2) thereby releasing the peptide. Exemplary labile linkages are described in U.S. Pat. No. 5,108,921, the entire disclosure of which is incorporated herein by reference. The peptide-active agent delivery system may also dissociate by way of chemical cleavage between the active agent and peptide of the invention. Within the embodiments wherein the linker moiety includes amino acid residues, such cleavage may occur within the linker moiety itself.

The examples provided below are intended to be illustrative and not comprehensive. Thus, the examples below illustrate the case where the bonds between the -M- group and the peptides are amide bonds, but the person skilled in the art would appreciate that the link may be formed by means of any functional groups capable of forming bonds between the terminal —NH— group of the peptide of amino acid sequence SEQ ID NO:2 and a —C(=O)— group of the terminal (or other) carboxyl group (or the terminal, or other NH— group, or any other functional group of the transduction domain).

If the link formed by the linking group is between the N-terminus of the peptide of amino acid sequence SEQ ID NO:2 and a carboxyl group of the tagging element (for example, the terminal carboxyl group of a peptidic tagging element of the terminal carboxyl group of a molecule), any amino acid (including, but not restricted to, α-amino acids including, but not restricted to, the proteinogenic amino acids) or peptide chain may form the link between the peptide of amino acid sequence SEQ ID NO:2 and the working element.

Examples of suitable linking groups -M- for linking the N-terminus of the amino acid sequence SEQ ID NO:2 and a carboxyl group of the working element include:

—NH—CH(R)—C(=O)—, wherein R is a side chain of a proteinogenic amino acid;
a peptide chain; and
—NH—X$_m$—C(=O)—, wherein:
  m is one or greater, preferably one to three,
  each —X— is selected from the group consisting of:
    a linear, branched, or cyclic aliphatic hydrocarbon, wherein one or more methylene groups are optionally replaced by O— or —S— and one or more methine groups are optionally replaced by N;
    —CH$_2$CH$_2$(OCH$_2$CH$_2$)$_n$—; wherein "n" is one or greater; and,
    an aromatic or heteroaromatic ring.

If the link formed by the linking group is between the amino acid terminus of the peptide of amino acid sequence SEQ ID NO:2 and an amino group of the working element (for example, the terminal amino group of a peptidic working element or the terminal amino group of a molecule), the link between the two peptide groups could be for example be a urea (where -M- is —C(=O)—) or any dicarboxylic acid residue (e.g. -M- is —C(=O)—(C$_1$-C$_6$)alkylene-C(=O)—).

Examples of suitable linking group -M- for linking the N-terminus of the amino acid sequence SEQ ID NO:2 and an amino group of the working element include:

—C(=O)— (i.e. a urea);
—C(=O)-Pep$^1$-NH—C(=O)—NH-Pep$^2$-C(=O)—,
  wherein —NH-Pep$^1$-C(=O)— and —NH-Pep$^2$-C(=O)— each represent either an amino acid or a peptide chain, linked via their amino termini (or the α-amino group in the case of an amino acid) by the urea linkage —NH—C(=O)—NH—; and —C(=O)—X$_m$—C(=O)—, wherein:
  m is one or greater, preferably one to three;
  each —X— is selected from the group consisting of:
    a linear, branched, or cyclic aliphatic hydrocarbon, wherein one or more methylene groups are optionally replaced by O— or —S— and one or more methine groups are optionally replaced by N;
    —CH$_2$CH$_2$(OCH$_2$CH$_2$)$_n$—; wherein "n" is one or greater; and,
    an aromatic or heteroaromatic ring.

Although the -M- group is referred to as "linking" the working element and the peptide of amino acid sequence SEQ ID NO:2, the use of this term is not intended to imply any limitation as to the process by which the compound of Formula (I) is synthesized. Thus it is not necessary that the working element and a peptide of amino acid sequence SEQ ID NO:2 be separately synthesized and then linked together. Rather, the term merely describes the structural connection between the working element, the peptide of amino acid sequence SEQ ID NO:2, and the linking group -M- in the compound of Formula (I).

The tagging element is selected from the group consisting of a transduction domain and a detection label.

Non-limiting examples of transduction domains are peptides derived from the HIV Tat-derived peptide. The HIV Tat-derived peptide is a small basic peptide that has been successfully shown to deliver a large variety of cargoes, from small particles to proteins, peptides and nucleic acids, to the interior of a cell. The transduction domain appears to be confined to a small (9 amino acids) stretch of basic amino acids, with the sequence Arg-Lys-Lys-Arg-Arg-Gln-Arg-Arg-Arg [amino acid sequence SEQ ID NO:6] (Ruben et al., 1989, J. Virol. 63: 1-8; Fawell et al., 1994, Proc. Natl. Acad. Sci. U.S.A. 91: 664-668; Vives et al., 1997, J. Biol. Chem. 272: 16010-16017; Futaki et al., 2001, J. Biol. Chem. 276: 5836-5840). The preferred Tat-derived peptides to be used within the present invention are: Tyr-Gly-Arg-Lys-Lys-Arg-Arg-Gln-Arg-Arg-Arg [amino acid sequence SEQ ID NO:5], Arg-Lys-Lys-Arg-Arg-Gln-Arg-Arg-Arg [amino acid sequence SEQ ID NO:6], Gly-Arg-Lys-Lys-Arg-Arg-Gln-Arg-Arg-Arg-Gly-Tyr-Lys-Cys [amino acid sequence SEQ ID NO:7], Tyr-Gly-Arg-Lys-Lys-Arg-Arg-Gln-Arg-Arg-Arg-Gly [amino acid sequence SEQ ID NO:8], Gly-Arg-Lys-Lys-Arg-Arg-Gln-Arg-Arg-Arg-Pro-Pro-Gln-Cys [amino acid sequence SEQ ID NO:9], Gly-Arg-Lys-Lys-Arg-Arg-Gln-Arg-Arg-Arg-Pro-Pro-Gln [amino acid sequence SEQ ID NO:10], Tyr-Ala-Arg-Lys-Ala-Arg-Arg-Gln-Ala-Arg-Arg [amino acid sequence SEQ ID NO:11], Tyr-Ala-Arg-Ala-Ala-Ala-Arg-Gln-Ala-Arg-Ala [amino acid sequence SEQ ID NO:12], Tyr-Ala-Arg-Ala-Ala-Arg-Arg-Ala-Ala-Arg-Arg [amino acid sequence SEQ ID NO:13] and Tyr-Ala-Arg-Ala-Ala-Arg-Arg-Ala-Ala-Arg-Ala [amino acid sequence SEQ ID NO:14].

Other non-limiting examples of transduction domains are peptides derived from *Drosophila Antennapedia* transcription factor (ANTP), as described in Mann and Frankel, 1991, EMBO J. 10: 1733-1739; and Vives et al., 1997, J. Biol. Chem. 272: 16010-16017. The preferred ANTP derived peptides to be used within this invention are Arg-Gln-Ile-Lys-Ile-Trp-Phe-Gln-Asn-Arg-Arg-Met-Lys-Trp-Lys-Lys [amino acid sequence SEQ ID NO:15], Arg-Gln-Ile-Lys-Ile-Trp-Phe-Pro-Asn-Arg-Arg-Met-Lys-Trp-Lys-Lys [amino acid sequence SEQ ID NO:16], Lys-Lys-Trp-Lys-Met-Arg-Arg-Asn-Gln-Phe-Trp-Val-Lys-Val-Gln-Arg [amino acid sequence SEQ ID NO:17], Arg-Arg-Trp-Arg-Arg-Trp-Trp-Arg-Arg-Trp-Trp-Arg-Arg-Trp-Arg-Arg [amino acid sequence SEQ ID NO:18], Arg-Arg-Met-Lys-Trp-Lys-Lys [amino acid sequence SEQ ID NO:19], Apa-Arg-Gln-Ile-Lys-Ile-Trp-Phe-Gln-Asn-Arg-Arg-Met-Lys-Trp-Lys-Lys [amino acid sequence SEQ ID NO:20], and Apa-Arg-Gln-Ile-Lys-Ile-Trp-Phe-Pro-Asn-Arg-Arg-Met-Lys-Trp-Lys-Lys [amino acid sequence SEQ ID NO:21], wherein Apa is aminopentanoic acid.

Other non-limiting examples of transduction domains are the following peptides: Arg-Arg-Arg-Arg-Arg-Arg-Arg [amino acid sequence SEQ ID NO:22, arginine 7-mer], Arg-Arg-Arg-Arg-Arg-Arg-Arg-Arg-Arg [amino acid sequence SEQ ID NO:23, arginine 9-mer], Asp-Ala-Ala-Thr-Arg-Ser-Ala-Ala-Ser-Arg-Pro-Thr-Glu-Arg-Pro-Arg-Ala-Pro-Ala-Arg-Ser-Ala-Ser-Arg-Pro-Arg-Arg-Pro-Val-Glu [amino acid sequence SEQ ID NO:24, VP22 transduction domain (Herpes Simplex Virus 1)], Gly-Ala-Leu-Phe-Leu-Gly-Trp-Leu-Gly-Ala-Ala-Gly-Ser-Thr-Met-Gly [amino acid sequence SEQ ID NO:25, GP41 fusion sequence], Gly-Ala-Leu-Phe-Leu-Gly-Phe-Leu-Gly-Ala-Ala-Gly-Ser-Thr-Met-Gly-Ala-Trp-Ser-Gln-Pro-Lys-Ser-Lys-Arg-Lys-Val [amino acid sequence SEQ ID NO:26, GP41 fusion sequence], Met-Gly-Leu-Gly-Leu-His-Leu-Leu-Val-Leu-Ala-Ala-Ala-Leu-Gln-Gly-Ala-Trp-Ser-Gln-Pro-Lys-Lys-Lys-Arg-Lys-Val [amino acid sequence SEQ ID NO:27, *Caiman crocodylus* Ig(v) light chain—SN40NLS], Pro-Leu-Ser-Ser-Ile-Phe-Ser-Arg-Ile-Gly-Asp-Pro [amino acid sequence SEQ ID NO:28, hepatitis B virus PreS2 antigen consisting of the translocation motif from residues 41-52], Phe-Trp-Arg-Gly-Asp-Leu-Val-Phe-Asp-Phe-Gln-Val [amino acid sequence SEQ ID NO:29, hepatitis A virus VP3 core protein], Lys-Phe-Thr-Ile-Val-Phe-Pro-His-Asn-Gln-Lys-Gly-Asn-Trp-Lys-Asn-Val-Pro-Ser-Asn-Tyr-His-Tyr-Cys-Pro [amino acid sequence SEQ ID NO:30, vesicular stomatitis virus VSV-G peptide], Ala-Lys-Arg-Ala-Arg-Leu-Ser-Thr-Ser-Phe-Asn-Pro-Val-Tyr-Pro- Tyr-Glu-Asp-Glu-Ser [amino acid sequence SEQ ID NO:31, adenovirus fiber], Gly-Trp-Thr-Leu-Asn-Ser-Ala-Gly-Tyr-Leu-Leu-Gly-Lys-Ile-Asn-Leu-Lys-Ala-Leu-Ala-Ala-Leu-Ala-Lys-Lys-Ile-Leu [amino acid sequence SEQ ID NO:32, transportan], Arg-Gly-Gly-Arg-Leu-Ser-Tyr-Ser-Arg-Arg-Arg-Phe-Ser-Thr-Ser-Thr-Gly-Arg [amino acid sequence SEQ ID NO:33, SynB1], Ala-Ala-Val-Ala-Leu-Leu-Pro-Ala-Val-Leu-Leu-Ala-Leu-Leu-Ala-Pro [amino acid sequence SEQ ID NO:34, Kaposi's sarcoma-associated herpesvirus, Kaposi FGF signal sequence], Ala-Ala-Val-Leu-Leu-Pro-Val-Leu-Leu-Ala-Ala-Pro [amino acid sequence SEQ ID NO:35, Kaposi's sarcoma-associated herpesvirus, Kaposi FGF signal sequence], Val-Thr-Val-Leu-Ala-Leu-Gly-Ala-Leu-Ala-Gly-Val-Gly-Val-Gly [amino acid sequence SEQ ID NO:36, human integrin beta3 signal sequence], Val-Ala-Tyr-Ile-Ser-Arg-Gly-Gly-Val-Ser-Thr-Tyr-Tyr-Ser-Asp-Thr-Val-Lys-Gly-Arg-Phe-Thr-Arg-Gln-Lys-Tyr-Asn-Lys-Arg-Ala [amino acid sequence SEQ ID NO:37, P3 membrane fusion sequence], Lys-Leu-Ala-Leu-Lys-Leu-Ala-Leu-Lys-Ala-Leu-Lys-Ala-Ala-Leu-Lys-Leu-Ala [amino acid sequence SEQ ID NO:38, model ambiphilic peptide], Trp-Glu-Ala-Lys-Leu-Ala-Lys-Ala-Leu-Ala-Lys-Ala-Leu-Ala-Lys-His-Leu-Ala-Lys-Ala-Leu-Ala-Lys-Ala-Leu-Lys-Ala-Cys-Glu-Ala [amino acid sequence SEQ ID NO:39, KALA], Arg-Arg-Gln-Arg-Arg-Thr-Ser-Lys-Leu-Met-Lys-Arg [amino acid sequence SEQ ID NO:40, disclosed in U.S. Pat. No. 6,881,825, the disclosure of which is incorporated by reference herein in its entirety] and Val-Asp-Lys-Gly-Ser-Tyr-Leu-Pro-Arg-Pro-Thr(NAcGal)-Pro-Pro-Arg-Pro-Ile-Tyr-Asn-Arg-Asn [amino acid sequence SEQ ID NO. 41, disclosed in U.S. Pat. No. 7,015,309, the disclosure of which is incorporated by reference herein in its entirety].

Non-limiting examples of detection labels are fluorescent labels, such as cyanin derivatives (Bioconj. Chem. 1993, 4: 105-111), coumarin derivatives such as aminomethylcoumarin (Histochem. J. 1986, 8(9): 497-9), Lucifer Yellow (Invitrogen, Carlsbad, Calif.), dansyl chloride and derivatives (Methods Mol. Biol. 1994, 32: 329-34), phycobiliproteins (such as B-phycoerythrin, R-phycoerythrin and allophycocyanin; Biochem, J. 1980, 187 (2): 303-9), Oregon Green 488 (J. Lipid Res. 2003, 44 (5): 1033-1041), rhodamine derivatives (such as Rhodamine B, Rhodamine 6G, Rhodamine 123, tetramethylrhodamine, Sulforhodamine 101, and Rhodamine Red; Invitrogen, Carlsbad, Calif.), Texas Red (sulfonyl chloride version of sulforhodamine 101; Immunol. Methods 1982, 50 (2): 193-204), fluorescein (Pract. Synth. Proced. 2004, 31 (15): 2591-2593), BODIPY derivatives (FL, TR, and TMR; Chem. Rev. 2007, 107 (11): 4891-4932), carboxy SNARF-1 (Invitrogen, Carlsbad, Calif.), Cascade Blue (Invitrogen, Carlsbad, Calif.), and the family of Alexa Fluor dyes (such as Alexa Fluor 350, Alexa Fluor 488, Alexa Fluor 647, Alexa Fluor 546, Alexa Fluor 594, Alexa Fluor 660, and Alexa Fluor 680; Molecular Probes, Invitrogen, Carlsbad, Calif.).

Salts of the Compounds of the Invention

The compounds of the invention may form salts with acids or bases, and such salts are included in the present invention. The preferred salts are pharmaceutically-acceptable salts. The term "salts" embraces addition salts of free acids or free bases that are compounds of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4 hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β hydroxybutyric, salicylic, galactaric and galacturonic acid.

Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. All of these salts may be prepared from the corresponding compound by reacting, for example, the appropriate acid or base with the compound.

Pharmaceutical Compositions

The compounds of the invention may be administered in the form of a pharmaceutical composition, in combination with a pharmaceutically acceptable carrier. The active ingredient in such formulations may comprise from 0.1 to 99.99 weight percent. "Pharmaceutically acceptable carrier" means any carrier, diluent or excipient which is compatible with the other ingredients of the formulation and not deleterious to the recipient.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., Remington's Pharmaceutical Sciences, 18th Edition (1990), Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of the active agent. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propyl-paraben, and chlorobutanol. The composition for parenteral administration may take the form of an aqueous or non aqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The compositions are preferably formulated in a unit dosage form, each dosage containing from about 1 to about 500 mg. The term "unit dosage form" refers to physically discrete units suitable as a unitary dosage for human subjects and other mammals, each unit containing a predetermined quantity of active material calculated to produce the desired therapeutic effect, in association with a suitable pharmaceutical excipient.

The pharmaceutical compositions of the present invention may also be formulated so as to provide slow or controlled release of the active ingredient therein, using, for example, hydropropylmethyl cellulose in varying proportions to provide the desired release profile, other polymer matrices, gels, permeable membranes, osmotic systems, multilayer coatings, microparticles, liposomes and/or microspheres.

In general, a controlled-release preparation is a pharmaceutical composition capable of releasing the active ingredient at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations. In an embodiment of the invention, a controlled release composition of the invention provides continuous release of an active agent over a fourteen day period of time.

U.S. Pat. No. 5,674,533 discloses controlled-release pharmaceutical compositions in liquid dosage forms for the administration of moguisteine, a potent peripheral antitussive. U.S. Pat. No. 5,059,595 describes the controlled-release of active agents by the use of a gastro-resistant tablet for the therapy of organic mental disturbances. U.S. Pat. No. 5,591,767 describes a liquid reservoir transdermal patch for the controlled administration of ketorolac, a non-steroidal anti-inflammatory agent with potent analgesic properties. U.S. Pat. No. 5,120,548 discloses a controlled-release drug delivery device comprised of swellable polymers. U.S. Pat. No. 5,073,543 describes controlled-release formulations containing a trophic factor entrapped by a ganglioside-liposome vehicle. U.S. Pat. No. 5,639,476 discloses a stable solid controlled-release formulation having a coating derived from an aqueous dispersion of a hydrophobic acrylic polymer. Biodegradable microparticles are known for use in controlled-release formulations. U.S. Pat. No. 5,354,566 discloses a controlled-release powder that contains the active ingredient. U.S. Pat. No. 5,733,566, describes the use of polymeric microparticles that release antiparasitic compositions.

The controlled-release of the active ingredient may be stimulated by various inducers, for example pH, temperature, enzymes, water, or other physiological conditions or compounds. Various mechanisms of drug release exist. For example, in one embodiment, the controlled-release component may swell and form porous openings large enough to release the active ingredient after administration to a patient. The term "controlled-release component" in the context of the present invention is defined herein as a compound or compounds, such as polymers, polymer matrices, gels, permeable membranes, liposomes and/or microspheres, that facilitate the controlled-release of the active ingredient in the pharmaceutical composition. In another embodiment, the controlled-release component is biodegradable, induced by exposure to the aqueous environment, pH, temperature, or enzymes in the body. In another embodiment, sol-gels may be used, wherein the active ingredient is incorporated into a sol-gel matrix that is a solid at room temperature. This matrix is implanted into a patient, preferably a mammal, having a body temperature high enough to induce gel formation of the sol-gel matrix, thereby releasing the active ingredient into the patient.

Compositions of the compounds of the invention that are suitable for administration intranasally or by inhalation are of particular interest.

The compounds of the invention can be administered intranasally or by inhalation, typically in the form of a dry powder (either alone, as a mixture, for example, in a dry blend with lactose in anhydrous or monohydrate form, preferably monohydrate, mannitol, dextran, glucose, maltose, sorbitol, xylitol, fructose, sucrose or trehalose, or as a mixed component particle, for example, mixed with phospholipids) from a dry powder inhaler or as an aerosol spray from a pressurized container, pump, spray, atomizer (preferably an atomizer using electrohydrodynamics to produce a fine mist), or nebulae, with or without the use of a suitable propellant, such as dichlorofluoromethane.

The pressurized container, pump, spray, atomizer, or nebulae contains a solution or suspension of the active compound comprising, for example, ethanol (optionally, aqueous ethanol) or a suitable alternative agent for dispersing, solubilizing, or extending release of the active, the propellant(s) as solvent and an optional surfactant, such as sorbitan trioleate or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

A suitable solution formulation for use in an atomizer using electrohydrodynamics to produce a fine mist may contain from 1 µg to 20 mg of the compound of the invention per actuation and the actuation volume may vary from 1 µL to 100 µL. A typical formulation may comprise the compound of the invention, propylene glycol, sterile water, ethanol and sodium chloride. Alternative solvents that may be used instead of propylene glycol include glycerol and polyethylene glycol.

Capsules, blisters and cartridges (made, for example, from gelatin or HPMC) for use in an inhaler or insufflator may be formulated to contain a powder mix of the compound of Formula (I), a suitable powder base such as lactose or starch and a performance modifier such as L-leucine, mannitol, or magnesium stearate.

Formulations for inhaled/intranasal administration may be formulated to be immediate and/or modified release. Modified release formulations include delayed-, sustained-, pulsed-, controlled dual-, targeted and programmed release. Sustained or controlled release may be obtained by using for example poly(D,L-lactic-co-glycolic acid).

Activity of the Compounds of the Invention

In an aspect, a compound of the invention has "full agonist activity" of the leptin receptor ("ObR"). As used herein, "full agonist activity" means that a compound of invention demonstrates agonistic activity, but does not demonstrate antagonistic activity with respect to ObR both in the presence and absence of exogenous native leptin or other ObR-stimulating agents at a concentration that is at least 100 times higher than the concentration at which the agonistic activity is observed.

Compounds of the invention that bind to ObR or that bind to and stimulate some or all of the function of ObR (ObR agonistic activity) may be assayed using a cellular assay as set forth in detail in Example 1 herein. In an embodiment of the invention, an ObR binding and/or agonist assay is conducted using a cell line expressing ObR, wherein such cells are stimulated to grow as a result of treatment with leptin or leptin analogs. The skilled artisan will be aware of methods of detecting peptide-receptor binding. Western blotting and dot-blotting techniques, among others, are useful for determining the binding of a compound of the invention to ObR. The skilled artisan will also be aware of methods of detecting and measuring cell growth. Cell counting, among other techniques, may be used to determine cell growth as a result of agonist activity of a compound of the present invention.

Other methods of measuring efficacy of compounds of the invention include, but are not limited to, receptor-binding assays, monitoring changes in downstream signaling of intracellular signaling pathways, induction of DNA and/or protein synthesis, or monitoring metabolic status of cells. Additionally, the efficacy of compounds of the invention may be assayed in animal models, i.e., by monitoring the ability of the compounds to substitute for leptin in leptin-deficient animals, or by monitoring appetite, metabolic rates, glucose/lipid levels, increased level of thermogenesis and/or decreased food intake, in animals with obesity and insulin resistance.

Methods of Treatment Using Compounds of the Invention

The compounds of the invention are useful as ObR agonists. They bind to ObR and agonize ObR-mediated activity, and thus may be used for the treatment of diseases and conditions that can benefit from an ObR-mediated upregulation in cell signaling and growth, including conditions that are related to leptin deficiency or leptin resistance. Accordingly, compounds of the invention may be used to treat conditions including, but not limited to, obesity, including appetite control in obesity; type II diabetes; appetite control after bariatric surgery; lipodystrophy; metabolic syndrome; hypothalamic amenorrhea; lipodystrophy; infertility; infertility associated with polycystic ovarian syndrome; weight control during dieting, including diet-induced food craving; osteoporosis as a complication of hypothalamic amenorrhea; and impaired cognitive functions. The aforementioned conditions are related to, at least in part, to leptin deficiency and/or leptin resistance.

Therefore, an individual who is in need of treatment with a compound according to the invention may be an individual who is suffering from one or more symptoms of obesity, lipodystrophy, metabolic syndrome, diet-induced food craving, type II diabetes, lack of or deficiency in appetite control after bariatric surgery, infertility, including obesity-related infertility and lipodystrophy-related infertility, or osteoporosis as a complication of hypothalamic amenorrhea, impaired cognitive functions, among other disorders.

For example, lipoatrophic diabetes is a syndrome characterized by insulin resistance in association with a paucity of adipose tissue. Patients with severe lipoatrophy die prematurely, typically from the complications of diabetes or liver disease. Experimental evidence suggests that the insulin resistance in these patients is caused by the lack of adipose tissue. Because adipose tissue normally produces leptin, the leptin deficiency in this syndrome may cause high blood lipid levels and insulin resistance that may lead to diabetes. Administration of ObR agonists according to the present invention can treat this diabetic condition, as well as other conditions which are related to a deficit of leptin or leptin activity.

Similarly, in individuals having metabolic changes that decrease the level of leptin in the body, i.e., individuals who are dieting, women with hypothalamic ammenorhea, and individuals having osteopenia or osteoporosis, administration of ObR agonists according to the present invention can treat the adverse conditions by stimulating (i.e., "agonizing") ObR.

In obese individuals, leptin is produced by fat tissue, but fails to activate ObR in the hypothalamus, resulting in increased appetite and weight gain. This leptin resistance may be overcome by the administration of ObR-specific agonists, such as the compounds of the present invention. Weight-reduced individuals are in a state of relative leptin deficiency due to loss of body fat. Energy and neuroendocrine homeostatic systems are altered during the maintenance of a reduced body weight in a manner that favors weight regain. These metabolic changes accompanying maintenance of reduced body weight may be reversed by administration of an ObR agonist to the individual.

Leptin regulates fertility through the hypothalamic-pituitary-gonadal axis, acting indirectly to stimulate gonadotropin-releasing hormone and gonadotropin levels (Israel & Chua, 2010, Trends Endocrinol. Metab. 21:10-16). These fertility functions of leptin are disturbed in the state of obesity and leptin resistance, and can be corrected by administration of a leptin agonist.

In an embodiment, the invention includes a method of treating obesity in a patient in need thereof. The method comprises administering a therapeutically effective amount of a compound of the invention, or a therapeutically effective amount of a pharmaceutical composition comprising a compound of the invention, or a salt thereof, as described herein, to an individual in need to such treatment or prophylaxis. An obese individual can benefit from treatment with a compound, as described herein, because the compound can agonize the activity of ObR. As set forth in detail elsewhere herein, an effective amount of a compound of the invention can be administered to an individual for the purpose of reducing voluntary food intake by the individual, which can aid weight and/or fat loss in the individual.

In an embodiment, the invention includes a method of treating an overweight condition in an individual in need thereof. The method comprises administering a therapeutically effective amount of a compound of the invention, or a therapeutically effective amount of a pharmaceutical composition comprising a compound of the invention, or a salt thereof, as described herein, to an individual in need to such treatment or prophylaxis. An overweight patient can benefit from this treatment much the same as an obese individual, as described above.

In an embodiment, the invention includes a method of treating lipodystrophy in a patient in need thereof. The method comprises administering a therapeutically effective amount of a compound of the invention, or a therapeutically effective amount of a pharmaceutical composition comprising a compound of the invention, or a salt thereof, as described herein, to an individual in need of such treatment or prophylaxis.

Lipodystrophy is a condition in which an individual experiences a loss in subcutaneous fat tissue. Lipodystrophy may be congenital or acquired (e.g., fat loss at a site of repeated insulin injections in diabetics), and presents as changes in the appearance of the skin at a site of the condition. Depressions in the skin, sagging of the skin, and pronounced appearance of the underlying structures are all physical manifestations of lipodystrophy. Metabolic disorders and resistance to insulin are also possible outcomes of lipodystrophy in a patient. Treatment of a lipodystrophy patient according to the invention may reverse or otherwise treat one or more of the lipodystrophy-associated conditions described herein by agonizing the activity of ObR, and by overcoming leptin resistance in resistant individuals.

In another embodiment, the invention includes a method of treating obesity-mediated infertility in a patient in need thereof. The method comprises administering a therapeutically effective amount of a compound of the invention, or a therapeutically effective amount of a pharmaceutical composition comprising a compound of the invention, or a salt thereof, as described herein, to an individual in need of such treatment or prophylaxis. Administration of the compound to a patient can agonize ObR activity to treat infertility by establishing a regular and/or increased program of voluntary food intake by the individual, thereby establishing a healthy physiological state in the individual.

Hypothalamic amenorrhea is a common cause of amenorrhea in women. Causes of hypothalamic amenorrhea include stress, weight loss (e.g., anorexia or bulimia), excessive exercise, certain medications, such as supplemental hormones, and hypothyroidism, among others. Accordingly, administration of an ObR agonist to such individuals, according to the present invention, can reinstate normal menstrual patterns by regulating leptin-mediated metabolism in these individuals.

The term "metabolic syndrome" is often used to refer to a cluster of adverse medical conditions including, but not limited to, insulin resistance without marked hyperglycemia, associated with atherosclerosis, obesity, hyperlipidemia, and essential hypertension. Treatments for metabolic syndrome include a reduction in voluntary food intake on the part of the affected individual. Therefore, the present invention includes a method of treating a patient having metabolic syndrome by administering a therapeutically effective amount of a compound of the invention, or a therapeutically effective amount of a pharmaceutical composition comprising a compound of the invention, or a salt thereof, as described herein, to the patient. Administration of a compound of the invention will induce satiety in the affected individual, and may enhance or recover attenuated sensitivity to leptin.

The presence of a leptin deficit in an individual may be readily detected in a patient by any means standard in the art, such as by measurement of systemic leptin levels by standard ELISA methods. The skilled artisan may be motivated to undertake such testing, for example, based on the nature of the disorder afflicting the patient (e.g., observation of obesity in obese patients and irregular menstruation in women with hypothalamic amenorrhea).

The amount of the therapeutic compound of the invention that will be effective in the treatment of a particular disorder or condition will depend on the nature of the disorder or condition, and is determined by standard clinical techniques. In addition, in vitro assays may optionally be employed to help identify optimal dosage ranges. The precise dose to be employed in the formulation also will depend on the route of administration and the seriousness of the disease, disorder, or condition and is decided according to the judgment of the practitioner and each patient's circumstances.

Administration of Compounds of the Invention

In an embodiment of the invention, the compounds are administered by way of an intranasal administration. However, the compounds may be administered by any route, including transdermal skin patch, oral, rectal, pulmonary, sublingual, and parenteral administration. Parenteral administration includes, for example, intraperitoneal, intravenous, intramuscular, intraarterial, intravesical (e.g., to the bladder), intradermal, transdermal, topical or subcutaneous administration.

Typically it is contemplated that treatment would be given at least once per day, typically once, twice, three times or four times per day with the doses given at equal intervals throughout the day and night in order to maintain a constant presence of the drug in order to induce sufficient agonistic activity in ObR. However, the skilled artisan will be aware that a treatment schedule may be optimized for any given patient, and that administration of compound may occur less frequently than once per day.

One or more compounds of the invention may be administered simultaneously, by the same or different routes, or at different times during treatment. The compounds of the invention may also be prescribed to be taken in combination with other drugs used to treat obesity, lipodystrophy, obesity-mediated infertility, type II diabetes, appetite control after bariatric surgery, appetite control in obesity, metabolic syndrome, lipodystrophy-related infertility, diet-induced food craving, impaired cognitive functions and osteoporosis as a complication of hypothalamic amenorrhea. When used in such combinations compounds of the invention and conventional drugs may be administered simultaneously, by the same or different routes, or at different times during treatment. The dose of the conventional drug selected will depend on the particular compound being used and the route and frequency of administration.

The treatment may be carried out for as long a period as necessary. Typically it is contemplated that treatment would be continued indefinitely while the disease state persists, although discontinuation might be indicated if the compounds no longer produce a beneficial effect. The treating physician will know how to increase, decrease, or interrupt treatment based on patient response.

The specific dose of a compound according to the invention to obtain therapeutic benefit for treatment of obesity will, of course, be determined by the particular circumstances of the individual patient including the size, weight, age and sex of the patient, the nature and stage of the disease, the aggressiveness of the disease, and the route of administration of the compound.

For example, a daily dosage from about 0.02 to about 50 mg/kg/day may be utilized, more preferably from about 0.1 to about 10 mg/kg/day. Higher or lower doses are also contemplated as it may be necessary to use dosages outside these ranges in some cases. The daily dosage may be divided, such as being divided equally into two to four times per day daily dosing. Suitable dosage ranges for intravenous administration are generally about 20-500 micrograms of active compound per kilogram body weight.

The invention also provides a pharmaceutical pack or kit comprising one or more containers filled with one or more of the ingredients of the pharmaceutical compositions of the invention. Optionally associated with such container(s) is a notice in the form prescribed by a governmental agency regulating the manufacture, use or sale of pharmaceuticals or biological products, which notice reflects approval by the agency of manufacture, use or sale for human administration.

In accordance with the present invention, as described above or as discussed in the Examples below, there may be employed conventional clinical, chemical, cellular, histochemical, biochemical, molecular biology, microbiology and recombinant DNA techniques that are known to those of skill in the art. Such techniques are explained fully in the literature.

The invention should not be construed to be limited solely to the assays and methods described herein, but should be construed to include other methods and assays as well. One of skill in the art will know that other assays and methods are available to perform the procedures described herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

EXAMPLES

The invention is described hereafter with reference to the following examples. The examples are provided for the purpose of illustration only and the invention should in no way be construed as being limited to these examples, but rather should be construed to encompass any and all variations that become evident as a result of the teaching provided herein.

Materials

Human leptin was purchased from R&D Systems (Minneapolis, Minn.).

LN18 and LN229 cells naturally expressing ObR were purchased from ATCC and were cultured in DMEM low glucose plus 5% fetal bovine serum.

Methods

Peptide Synthesis

Peptides were synthesized on a CEM Liberty microwave peptide synthesizer (CEM, Matthews, N.C., USA) at a 0.025-1 mmol scale using Rink Amide AM Resin. Couplings were performed at 75° C. for 10 minutes with 25 W radiation energy, using HATU (2-[1H-7-azabenzotriazol-1-yl]-1,1,3,3-tetramethyl uronium hexafluorophosphate) as the activation agent. Repetitive removal of the N-terminal Fmoc-groups was done with 20% (v/v) piperidine and 0.1 M HOBt in dimethyl-formamide (DMF) at 75° C. for 3 minutes with 35 W radiation energy. The glycoamino acid, Fmoc-Thr ($\alpha$GalNAc$_4$)—OH, where the three sugar hydroxyl groups and the sugar amino group are acetylated, was coupled in 1.5 molar excess with double coupling time followed by Fmoc-Ser(Trt)-OH in 5 molar excess and Fmoc-Tyr(I$_2$)—OH in 1 molar excess with double coupling time. No major side products were identified by HPLC or mass spectrometry, indicating that couplings were complete.

The peptides were cleaved from the resin by stirring them in a mixture of trifluoroacetic acid-water-triisopropylsilane (95:2.5:2.5 per volume) at 0° C. for 10 minutes and then at room temperature for 110 minutes. The peptides were precipitated with ice-cold diethyl ether, collected by filtration and washed with ice-cold ether three-times. The residue was dissolved in trifluoroacetic acid (TFA), and precipitated with ice-cold diethyl ether. The resulting precipitate was collected by filtration and dissolved in 5% acetic acid. The solvents were removed by lyophilization.

If present, O-acetyl groups were removed by dissolving the acylated material in 0.01 M NaOH and stirring it until removal of O-acetyl groups was complete, as determined by HPLC. The solution was neutralized with an equal volume of 0.01 M HCl.

In the event that the peptide was to be labeled with the fluorescent dye Alexa Fluor® 680, the deacetylated peptide was stirred with the succinimidyl ester of the dye (Catalog No. A-20108, Invitrogen, Carlsbad, Calif.) in a 1:2 molar ratio of peptide and dye in ammonium bicarbonate, pH, 8. The system was stirred at room temperature overnight.

Compound Purification

Compounds were purified by RP-HPLC (Gilson, Middleton, Wis., USA) using a Luna C18 column (5 µm, 250 mm×10 mm) (Phenomenex, Torrance, Calif., USA) at 4 mL/min with an aqueous phase of 0.1% TFA in water and an organic solvent of 0.09% TFA in acetonitrile. The peptide sequences were confirmed by ES-MS with a SCIEX API150EX mass spectrometer (PerkinElmer Life Sciences, Boston, Mass., USA). The compounds were lyophilized twice using 5% acetic acid to remove TFA salts. The purity of the final compounds or was checked by analytical HPLC.

Cell Proliferation Assay

Seventy percent confluent cultures of LN18 and LN229 cells were synchronized in serum-free medium (DMEM plus 10 µM FeSO$_4$ and 0.5% bovine serum albumin—BSA) for 48 hours and then treated with leptin and/or compounds (different doses) for 3 days. Cell numbers before and after treatment were determined by direct counting the cells with trypan blue exclusion. All assays were done in triplicate and repeated 3-6 times. The cell numbers were expressed as means±standard error. The results were statistically evaluated by Student's t-test and analysis of variance (ANOVA). Values of $p<0.05$ were considered statistically significant.

In Vivo Biodistribution

Compound (2), labeled with fluorescent dye Alexa Fluor® 680, was prepared and purified by reverse phase HPLC. 5 µg of the compound were injected intraperitoneally into anesthetized female Balb/c mice. While sleeping, the animals were placed into the fluorescence microscope chamber. Fluorescence exposure pictures were taken with a Kodak 4000MM camera set to 695 nm emission wavelength at five minute intervals afterwards for 80 min.

Histology

Animals were sacrificed by CO$_2$ inhalation. Livers were removed and fixed in 10% buffered formaldehyde, pH, 7.4. After 24 hour fixation, liver specimens were dehydrated in graded ethanol and placed into methyl benzoate for an hour. The specimens were then transferred to xylene and embedded into paraffin. 6-µm thick paraffin sections were deparaffinized and stained with H&E. Photomicrographs were taken by using a Zeiss light microscope equipped with a CCD camera. The final magnification of the pictures was 200-fold.

Preparation of DIO Mice

An animal model for leptin resistance was used to evaluate compounds of the invention. In this model, based on high-fat induced obesity (DIO) of normal mice, the animals are fed with a diet containing 40-60% fat and become resistant to leptin treatment (Steinberg et al., 2006, Endocrinology 147: 3906-3914; Nakagawa et al., 2003, J. Obesity 27: 557-565). Normal C57BL/6 mice were fed with regular 6% lab chow until 3 weeks of age when their diet was switched to peanuts only. Peanuts have 47-50% dry fat content, and are considered a typical high-fat food (Isleib et al., 2004, J. Agric. Food Chem. 52: 3165-3168). DIO mice develop peripheral leptin resistance after 16 days of high-fat diet (van Heek et al., 1997, J. Clin. Invest. 99:3 85-390). In this study, the mice were fed peanuts for 5 weeks. The animals had access to water and peanuts ad libitum. After 3 weeks (total age 6 weeks) a group of 6 mice remained untreated, and 4 groups received leptin or a compound of the invention.

Mice were weighed daily and received a daily single dose (around noon time) intraperitoneally with the following scheme: Group 1 (6 mice: 3 males, 3 females) —physiological solution (control); Group 2 (6 mice: 3 males, 3 females) —0.1 mg/kg/day leptin; Group 3 (4 mice: 2 males, 2 females) —0.02 mg/kg/day compound of the invention; Group 4 (6 mice: 3 males, 3 females) —0.1 mg/kg/day compound of the invention; and Group 5 (4 mice: 2 males, 2 females) —0.5 mg/kg/day compound of the invention. After 10 days of treatment, one male and one female mouse from each group were sacrificed and bled, and their livers, spleens, kidneys and brains were removed for histology and toxicity analysis.

Toxicity

Eight C57BL/6 mice, 6 weeks of age (8 mice: 4 males, 4 females), were fed with peanut diet for 6 days. They were split in three different groups. The first group was left untreated (4 mice: 2 males, 2 females). The second group received a compound of the invention once daily intraperitoneally at 1.5 mg/kg for 4 days (2 mice: 1 male, 1 female). The third group received a compound of the invention once daily intraperitoneally at 4.0 mg/kg (2 mice: 1 male, 1 female) for 4 days. The animals were inspected daily for signs of disease or discomfort. After 5 days of treatment, the mice were weighed, sacrificed with $CO_2$ inhalation, and bled for laboratory blood analysis. Their brains, livers, kidneys and spleens were inspected, removed and weighed.

Pregnancy Test

The remaining mice after the treatment with leptin or a compound of the invention were returned to 6% fat lab chow diet, and locked into cages in couples. They were observed for pregnancy for 5 weeks. The two successful litters were examined for growth and behavioral patterns.

Rat Appetite Control

Eight 6-weeks-old male F334 rats were kept on regular laboratory diet. At noon time for 10 days, the animals were weighed, turned upside down, and received 0.1 mg/kg/day of a compound of the invention (4 mice) or physiological solution (4 mice) dripped in 10 μL volume into their nose. On day 15, the rats were weighed and sacrificed (cervical dislocation), and bled for laboratory blood analysis. Their brains, livers, kidneys and spleens were removed and weighed.

Example 1

Identification of a Leptin-Based Agonist

In Vitro Activity of Compound (1)

Compound (1) [amino acid sequence SEQ ID NO:4] was identified as an agonist against the leptin receptor. Due to the presence of non-natural amino acids in both termini of the peptide chain, compound (1) should be more resistant to exopeptidase activity than an equivalent peptide containing only naturally occurring α-amino acids.

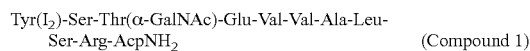
 (Compound 1)

Compound (1) was characterized by analytical HPLC (FIG. 1). The compound showing a single peak at the two monitoring wavelengths (220 and 280 nm), with a retention time of $t_r$=22.4 min (33% acetonitrile) and a molecular weight of 848.5 m/z by ES-MS. The overall purity of this compound was found to be >95%.

Stimulation of ObR-positive cells by compound (1) was evaluated. A true agonist of an ObR-positive receptor should stimulate the growth of ObR-positive cells when added alone and should not antagonize the actions of leptin in the same cells. In order to determine whether compound (1) is a true agonist, the ObR-positive, CNS-resident glioblastoma cell lines LN229 and LN18 were used. EC values for this peptide were measured without exogenous leptin present, and IC values with 12 nM leptin added.

Compound (1) stimulated the growth of these cells in subnanomolar concentrations (ECs), as shown in Table 2. Antagonistic properties (ICs) to leptin-induced LN229 stimulation could not be observed below 100 nM, and thus the selectivity index for this peptide is greater than 100. Based on this result, compound (1) may be considered a full ObR agonist. Compound (1) showed picomolar agonistic activities to other ObR-positive cells, such as the CNS-resident glioblastoma cell lines LN18 (data not shown).

TABLE 2

Effects of compound (1) on the proliferation of ObR-positive LN229 glioblastoma cells.

| | $EC_{50}$ (nM) | $EC_{100}$ (nM) | $IC_{50}$ (nM) | $IC_{100}$ (nM) | Selectivity (EC/IC) |
|---|---|---|---|---|---|
| compound (1) | <1 | <1 | 100 | >100 | >100 |

Example 2

In Vivo Distribution of Compound (2)

In order to assess the in vivo distribution of compound (1) in vivo, a labeled version of the compound—compound (2)—was prepared:

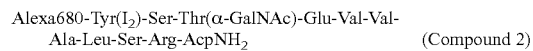
 (Compound 2)

Compound (2) was prepared by coupling compound (1) to the succinimidyl ester of Alexa Fluor® 680 fluorescent dye and purifying the product by reverse phase HPLC.

Figure 2:
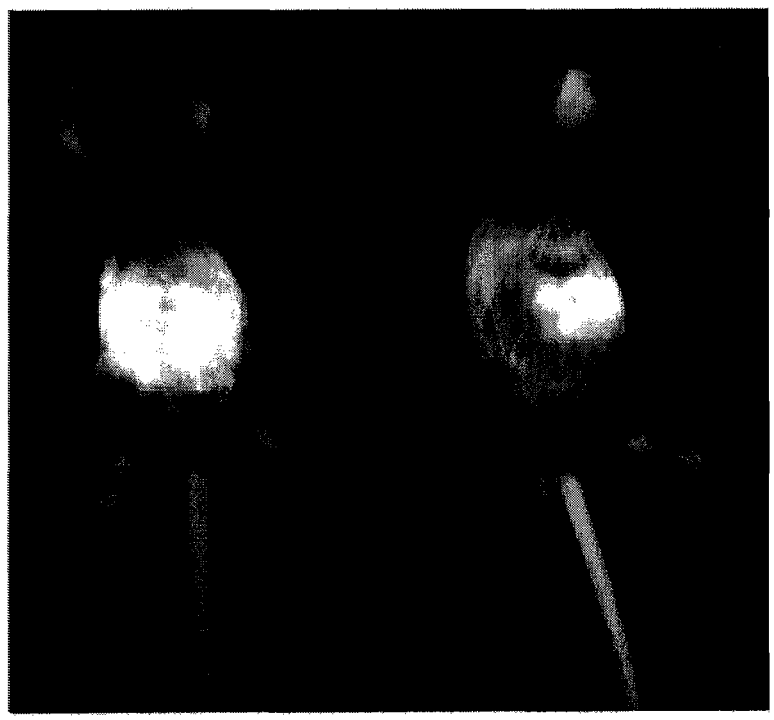
FIG. 2 illustrates fluorescence exposure pictures of anesthetized female Balb/C mice injected intraperitonically with compound (2) [Alexa680-Tyr($I_2$)-Ser-Thr(α-GalNAc)-Glu-Val-Val-Ala-Leu-Ser-Arg-AcpNH$_2$]. The pictures were taken with a Kodak 4000MM camera set to 695 nm emission wavelength, and fluorescence is shown as a light color against the dark background. Panel (A) shows the abdominal side of a mouse 45 minutes after injection. Panel (B) on the right shows the back side of the same animal 70 minutes after injection: fluorescence was observed on the back side of the head.

When injected intraperitoneally into Balb/c mice, compound (2) was distributed into the usual peptide elimination organs within one hour from administration: the kidneys, the liver and the spleen (FIG. 2) (Klootwijk et al., 1997, J. Clin. Endocrinol. Metab. 82: 3068-3073). In addition, the peptide was also found in the tail, the limbs and the brain (Otvos et al., 2008, Biochim. Biophys. Acta 1783: 1745-1754; Knappe et al., 2008, Int. J. Pept. Res. Ther. 14: 247-254). The presence of the peptide in the brain was more apparent when the mice were photographed from their back, consistent with the model where compound (2) indeed concentrates in the hypothalamic regions (FIG. 2, panel B). In summary, compound (2), and by inference compound (1), showed good BBB-penetrating ability and pharmacological properties in vitro.

Example 3

Mouse Model of Obesity and Leptin Resistance

Figure 3:
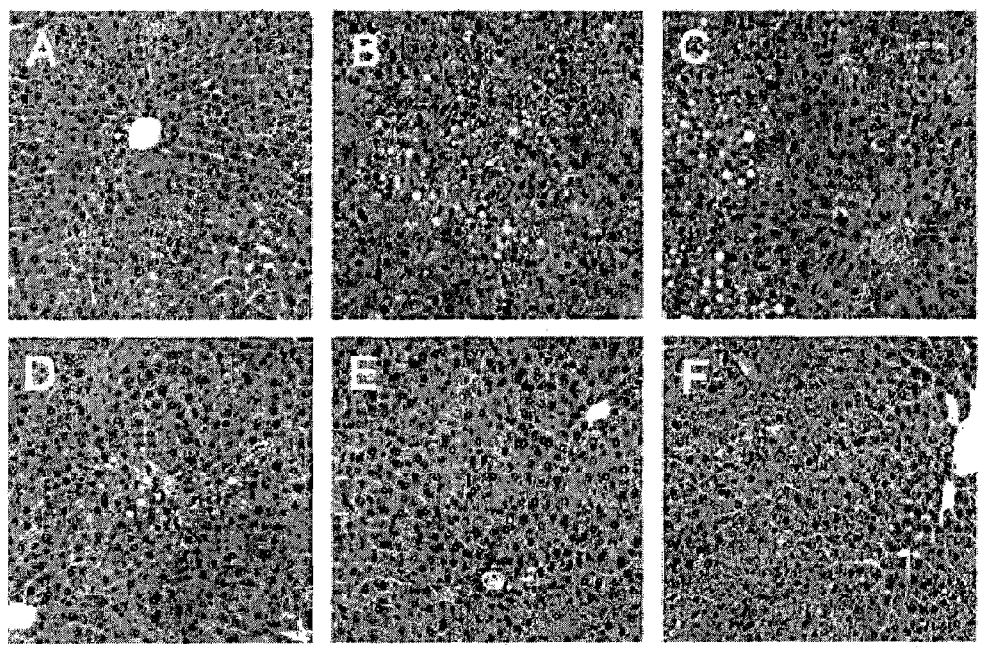
FIG. 3 illustrates liver sections of C57BL/6 mice submitted to different treatments: (A) normal mice fed with 6% fat lab chow; (B) mice on peanut (47% fat) diet for 5 weeks; (C) peanut-fed mice (5 weeks) including 11-days of treatment with compound (1) at 0.02 mg/kg/day intraperitoneally; (D) peanut-fed mice (5 weeks) including 11-days of treatment with compound (1) at 0.1 mg/kg/day intraperitoneally; (E) peanut-fed mice (5 weeks) including 11-days of treatment with compound (1) at 0.5 mg/kg/day intraperitoneally; and, (F) peanut-fed mice (5 weeks) including 11-days of leptin treatment at 0.1 mg/kg/day intraperitoneally. The liver sections are magnified by 200-fold, and foamy, fatty round cells in the liver are seen as white areas.

The mouse model for leptin resistance was used to evaluate compound (1). At the age of 8 weeks when the assay was terminated, the untreated DIO mice showed typical clinical signs of obesity, such as elevated total serum cholesterol level (Table 3). Furthermore, the high fat diet induced the appearance of foamy, fatty round cells in the acinoperipheral region of the liver (FIG. 3, panels A and B). The liver of female mice became less fatty than that of male subjects, which reflects the lowered predisposition of increased weight female C57BL/6 mice to exhibit obesity-related disorders than their male counterparts (Tortotriello et al., 2007, Internat. J. Obesity 31:

395-402). DIO mice become diabetic only after 16 weeks on high fat diet (Gout et al., 2008, Obesity 16: 1763-1769), and indeed, the serum glucose level of our peanut-fed mice remained below that of normal C57BL/6 mice (Table 3).

TABLE 3

Peripheral effects of treatment with leptin and the leptin agonist, compound (1).

| Treatment groups | Blood glucose level (mM/L) | Blood total cholesterol level (mM/L) | Number of couples examined | Number of pregnancy incidents |
|---|---|---|---|---|
| Mice on normal diet | 10.56 | 1.62 | N/A | N/A |
| Control untreated obese group | 8.49 | 2.27 | 2 | 0 |
| leptin 0.1 mg/kg/day | 5.22 | 2.47 | 2 | 1 |
| compound (1) 0.02 mg/kg/day | 8.45 | 2.51 | 1 | 0 |
| compound (1) 0.1 mg/kg/day | 8.55 | 2.77 | 1 | 0 |
| compound (1) 0.5 mg/kg/day | 7.06 | 2.08 | 1 | 1 |

Example 4

Efficacy and Toxicity of Compound (1) in Obese Mice

The DIO mice were allowed to eat peanut ad libitum. They were weighed daily and received the following intraperitoneal treatment at noontime: Group 1 (6 mice: 3 males, 3 females)—physiological solution (control); Group 2 (6 mice: 3 males, 3 females) —0.1 mg/kg/day of leptin; Group 3 (4 mice: 2 males, 2 females) —0.02 mg/kg/day of compound (1); Group 4 (6 mice: 3 males, 3 females) —0.1 mg/kg/day of compound (1); and Group 5 (4 mice: 2 males, 2 females) —0.5 mg/kg/day of compound (1).

Figure 4A:
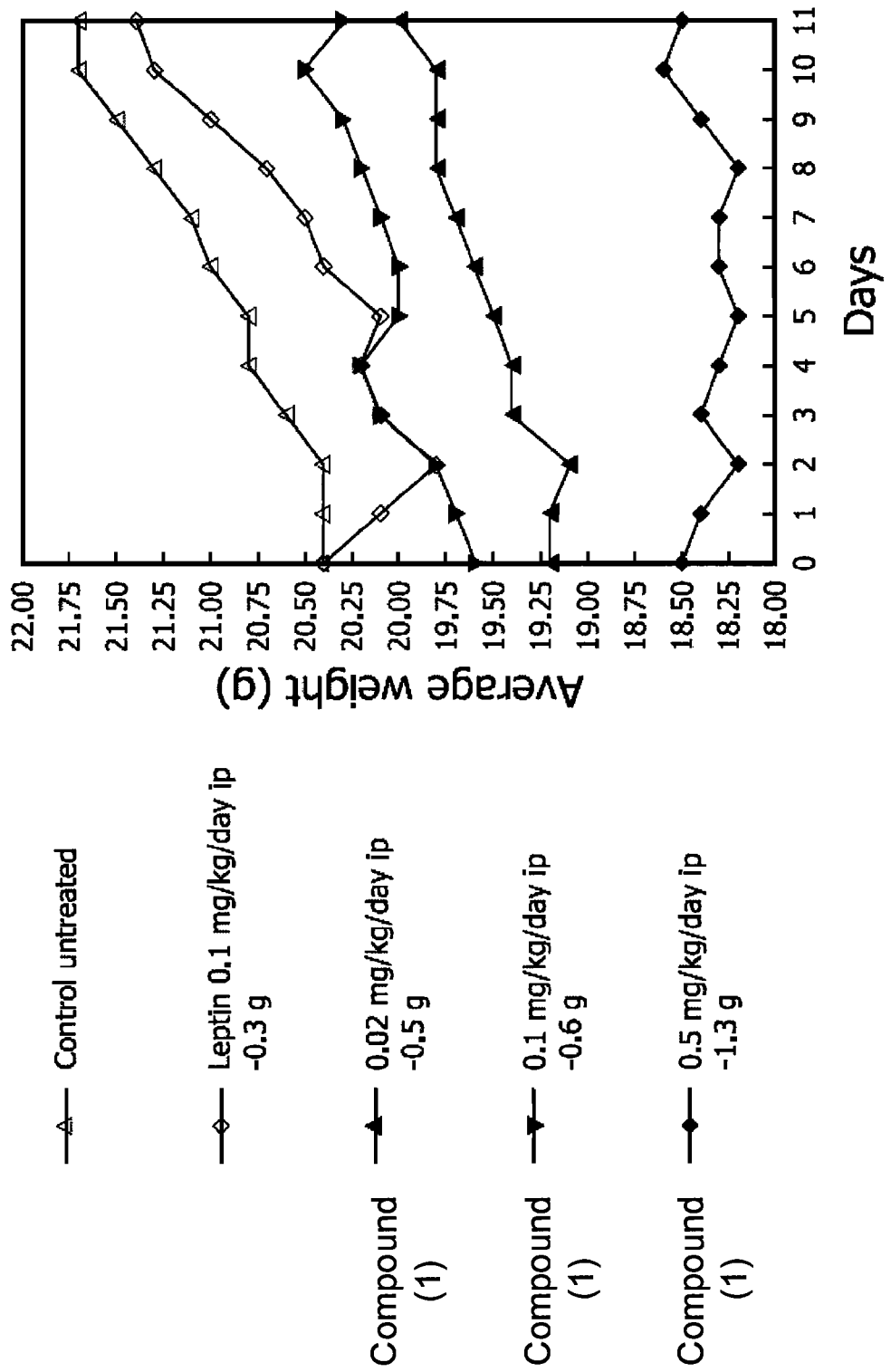
FIG. 4A illustrates the average weight for an equal number of males and females (2-3 animals per group) per group of obese C57BL/6 mice submitted to different treatments: untreated animals (A), leptin administered at a dose of 0.1 mg/kg/day ip (◇), compound (1) administered at a dose of 0.02 mg/kg/day ip (▲), compound (1) administered at a dose of 0.1 mg/kg/day ip (▼), and compound (1) administered at a dose of 0.5 mg/kg/day ip (◆).
Figure 4B:
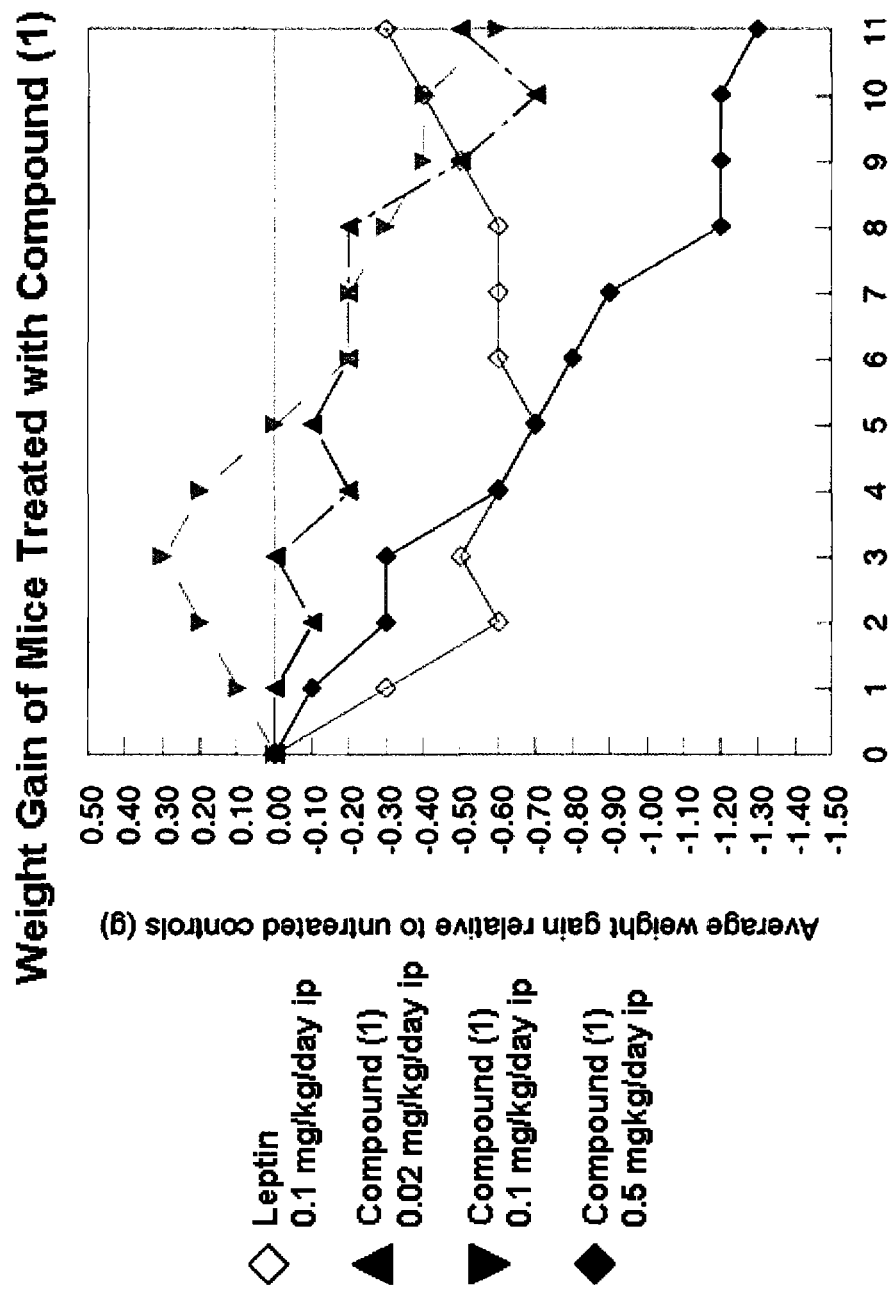
FIG. 4B illustrates equivalent data to FIG. 4A, replotted as average weight gain relative to untreated controls: leptin administered at a dose of 0.1 mg/kg/day ip (◇), compound (1) administered at a dose of 0.02 mg/kg/day ip (▲), compound (1) administered at a dose of 0.1 mg/kg/day ip (▼), and compound (1) administered at a dose of 0.5 mg/kg/day ip (◆).

During the 10-day treatment period, the control, untreated mice on average grew 1.3 g (FIG. 4). Mice treated with leptin initially lost weight, but from day 7 on they rapidly gained weight, indicating that treatment was successful at early periods but there was fast acquisition of resistance. By the end of the treatment period, the leptin-treated animals were 0.3 g lighter than the controls. Treatment with 0.02 mg/kg/day and 0.1 mg/kg/day of compound (1) was mildly successful. The weight gain level of the animals was reduced by 0.5 g and 0.6 g respectively, with more or less linear growth curves indicating the lack of resistance to peptide treatment. In contrast, mice receiving a daily dose of 0.5 mg/kg of compound (1) effectively lost weight throughout the examination period. The relative weight loss compared to untreated mice was 1.3 g, corresponding to 6.5% net total body weight loss in 10 days.

After 10 days of treatment, one male and one female mouse from each group were sacrificed, bled, and their livers, spleens, kidneys and brains were removed for histology and toxicity analysis. The organ sizes of representatives of all five groups were practically identical, and no toxicity was observed in any animal. Laboratory analysis of the blood indicated that the only treatment option that successfully reduced the total cholesterol level was the highest dose of compound (1), 0.5 mg/kg/day (Table 3), which also reduced blood glucose (Table 3). Remarkably, leptin treatment did not reduce the total cholesterol level, but significantly reduces the blood glucose level.

Similarly to the weight loss measurements, compound treatment lowered the fatty cell content of the liver in a dose-dependent manner. In the mice treated with 0.5 mg/kg/day of compound (1), mice fatty cytoplasm could no longer be observed (FIG. 3). In fact, this treatment regiment was more successful than that with 0.1 mg/kg/day of leptin, since in the latter the acinoperipheral regions of the liver still contained fat cells (FIG. 3).

In summary, these studies showed that compound (1) reduced weight gain linearly throughout the 11-day examination period and improved the liver fat content in a dose-dependent manner. The best effect was seen at 0.5 mg/kg/day when the mice effectively lost weight (6.5% relative weight loss), the blood cholesterol level was reduced by 9%, the glucose level was reduced by 17% and the fat cells were completely eliminated from the liver.

Example 5

Effect of Compound (1) on Fertility

Obese C57BL/6 mice, female and male uniformly, show signs of infertility that may be corrected, at least partially, with leptin treatment (Ewart-Toland et al., 1999, Endocrinology 140: 732-738; Mounzih et al., 1997, Endocrinology 138: 1190-1193).

Upon cessation of the weight gain assay and laboratory work, the remaining mice were returned to 6% fat lab chow diet, and locked into cages in couples to investigate whether treatment with leptin or compound (1) improved their fertility rates. They were observed for pregnancy for 5 weeks. Neither of two couples of control, untreated mice produced litters, as expected (Table 3). Similarly, the 2 couples of mice treated with the low-dose regiment of compound (1) remained infertile. Leptin treatment somewhat improved the situation because one of the two couples produced a litter. As for the couple of mice treated with the 0.5 mg/kg/day dose of compound (1), the female became pregnant immediately and delivered 6 healthy pups in less than a month (Table 3).

Example 6

Chronic Toxicity Study of Compound (1)

In order to shed light on the pharmacological profile of compound (1), a short chronic toxicity study was done with this compound.

Eight mice (4 males, 4 females) were fed with peanut diet for 6 days. After that, they were left untreated (2 males, 2 females), or received compound (1) once daily at 1.5 mg/kg (1 male, 1 female) or 4.0 mg/kg (1 male, 1 female) for 4 days. Three of the 4 treated mice lost weight during the compound addition period, with exception of the male that was dosed with 4.0 mg/kg/day. Gross necropsy showed no signs of toxicity. The average organ weights were: liver, 1.06 g; spleen, 0.09 g; kidney, 0.20 g (females) and 0.25 g (males); and brain, 0.3 g. This study shows compound (1) may be administered safely at higher doses, and such higher doses still exhibit leptin receptor agonistic properties in vivo.

Example 7

Intranasal Administration of Compound (1) to Normal Rats

The effects of compound (1) on weight gain were studied using intranasal administration in normal F344 male rats.

These animals are usually sensitive to leptin treatment (Scarpace, 1997, Am. J. Physiol. 273: E226-E230) and are amenable to intranasal administration.

Figure 5:
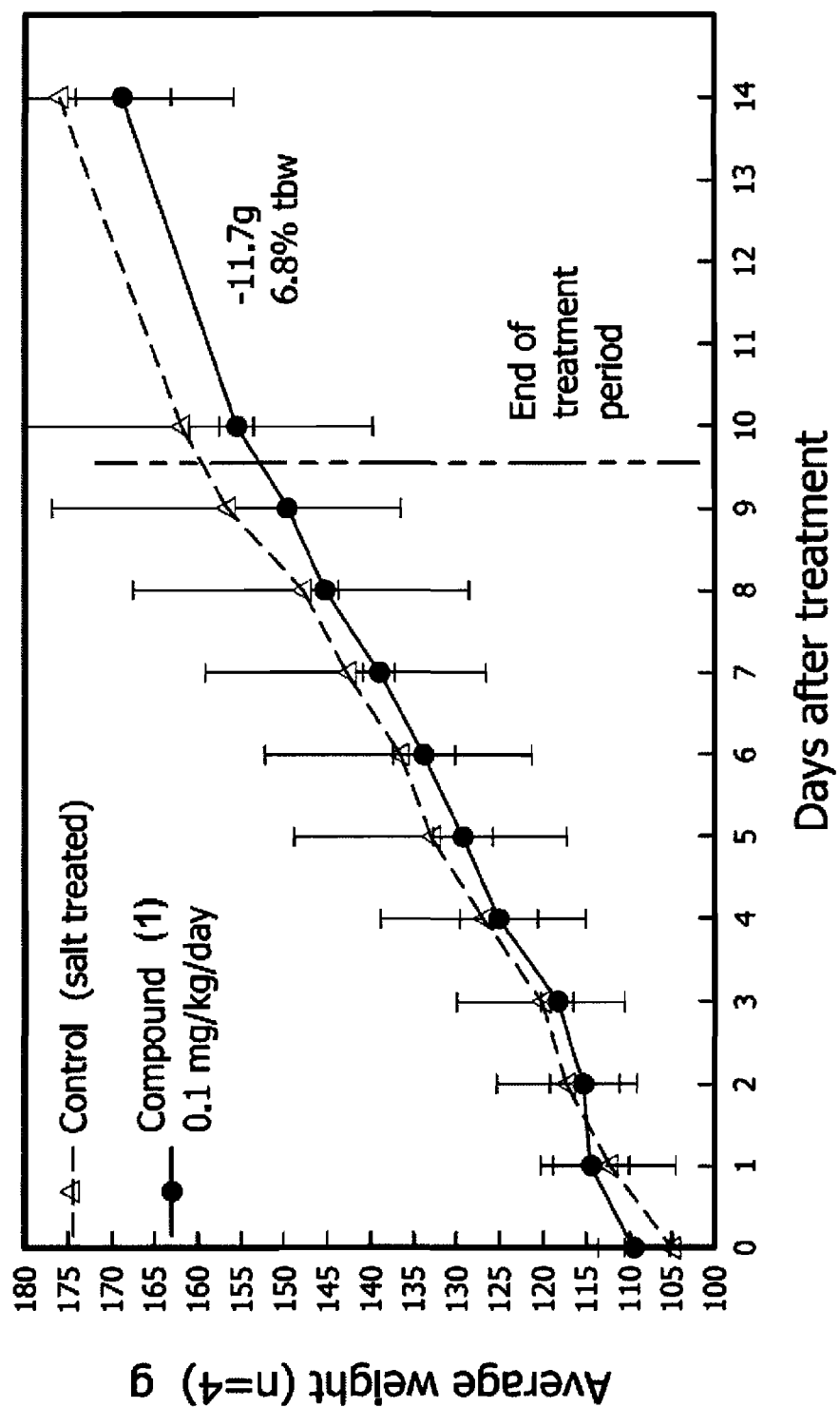
FIG. 5 illustrates the average weight for normal F344 male rats treated with intranasal administration of compound (1) (●) and with physiological solution (Δ).

Rats were allowed to lab chow ad libitum, and treatment lasted for 10 days with 0.1 mg/kg/day single dose of compound (1) dropped into the nose in 10 μL salt solution. Untreated control animals were administered 10 μL physiological salt solution. Results are represented in FIG. 5.

By day 11, the treated animals grew on average 10.8 g less than the untreated controls, and retained the relative weight loss until the end of the examination period. By day 14, the animals treated with compound (1) grew 11.7 g less than the controls, representing a 6.8% net total body weight (tbw) loss.

When the assay was completed, the rats were sacrificed. The control and compound treated mice had identical average total blood cholesterol levels (1.28 mmol/L) and organ weights (liver, 6.9 g for both; spleen, 0.45 g vs 0.42 g; kidney, 1.5 g for both; brain: 1.3 vs 1.2 g). Intranasal drug administration bypasses BBB limits (Charlton et al., 2008, Pharm. Res. 25:1531-1543), and direct comparison of the efficacy of the peptide in this model with the efficacy of leptin in other models described above is not possible. Nevertheless, this assay suggests treatment with compound (1) has an extended duration of action in the CNS.

The disclosures of each and every patent, patent application, and publication cited herein are hereby incorporated herein by reference in their entirety. One skilled in the art will readily appreciate that the present invention is well adapted to carry out the objects and obtain the ends and advantages mentioned, as well as those inherent therein. While the invention has been disclosed with reference to specific embodiments, it is apparent that other embodiments and variations of this invention may be devised by others skilled in the art without departing from the true spirit and scope used in the practice of the invention. The appended claims are intended to be construed to include all such embodiments and equivalent variations.

What is claimed:

1. A compound according to Formula (I):

X¹-M-SEQ ID NO:2   (I)

or a salt thereof, wherein:
   SEQ ID NO:2 represents Xaa₁-Xaa₂-Xaa₃-Glu-Val-Val-Ala-Leu-Ser-Xaa₄-Xaa₅,
   wherein:
   Xaa₁ is Tyr, Tyr(Me), Tyr(N-Me), Tyr(Me, N-Me), Tyr (I) or Tyr(I₂);
   Xaa₂ is Ser or a saccharide-modified serine;
   Xaa₃ is Thr or a saccharide-modified threonine;
   Xaa₄ is Arg or Arg(N-Me);
   Xaa₅ is a non-natural amino acid selected from the group consisting of a D-isomer of a natural amino acid, arginosuccinic acid, citrulline, cysteine sulfinic acid, 3,4-dihydroxyphenylalanine, homocysteine, homoserine, ornithine, 3-monoiodotyrosine, 3,5-diiodotyrosine, 3,5,5'-triiodothyronine, 3,3',5,5'-tetraiodothyronine, hydroxylysine, 4-hydroxyproline, an N-Cbz-protected amino acid, 2,4-diaminobutyric acid, homoarginine, N-methyl-arginine, norleucine, N-methylaminobutyric acid, naphthylalanine, phenylglycine, beta-phenylproline, tert-leucine, 4-aminocyclohexalalanine, N-methyl-norleucine, 3,4-dehydroproline, N,N-dimethylaminoglycine, N-methylaminoglycine, 4-aminopiperidine-4-carboxylic acid, Acp, AcpNH₂, bAla, bAlaNH₂, trans-4-(aminomethyl)-cyclohexanecarboxylic acid, 2-(aminomethyl)-benzoic acid, 3-(aminomethyl)-benzoic acid, 4-(aminomethyl)-benzoic acid, 1-aminocyclopentanecarboxylic acid, 1-aminocyclopropanecarboxylic acid, and 2-benzyl-5-aminopentanoic acid; and,
   X1-M is an optional group comprising a tagging element conjugated to the N-terminus of the amino acid sequence SEQ ID NO:2, wherein:
   X1 is the tagging element, wherein the tagging element is selected from the group consisting of a transduction domain and a detection label; and,
   -M- is a single bond or an optional linking group forming a covalent linkage between the tagging element and the amino acid sequence SEQ ID NO:2.

2. The compound of claim 1, wherein Xaa₁ is Tyr(Me), Tyr(N-Me), Tyr(Me, N-Me), Tyr(I) or Tyr(I₂).

3. The compound of claim 1, or a salt thereof, wherein Xaa₁ is Tyr(I₂).

4. The compound of claim 1, or a salt thereof, wherein -M- consists of a single bond, an amino acid or a peptide.

5. The compound of claim 1, or a salt thereof, wherein said tagging domain is directly linked at its C-terminus to -M-.

6. The compound of claim 1, or a salt thereof, wherein said tagging element is a transduction domain comprising an amino acid sequence selected from the group consisting of Tyr-Gly-Arg-Lys-Lys-Arg-Arg-Gln-Arg-Arg-Arg [SEQ ID NO:5], Arg-Lys-Lys-Arg-Arg-Gln-Arg-Arg-Arg [SEQ ID NO:6], Gly-Arg-Lys-Lys-Arg-Arg-Gln-Arg-Arg-Arg-Gly-Tyr-Lys-Cys [SEQ ID NO:7], Tyr-Gly-Arg-Lys-Lys-Arg- Arg-Gln-Arg-Arg-Arg-Gly [SEQ ID NO:8], Gly-Arg-Lys-Lys-Arg-Arg-Gln-Arg-Arg-Arg-Pro-Pro-Gln-Cys [SEQ ID NO:9], Gly-Arg-Lys-Lys-Arg-Arg-Gln-Arg-Arg-Arg-Pro-Pro-Gln [SEQ ID NO:10], Tyr-Ala-Arg-Lys-Ala-Arg-Arg-Gln-Ala-Arg-Arg [SEQ ID NO:11], Tyr-Ala-Arg-Ala-Ala-Ala-Arg-Gln-Ala-Arg-Ala [SEQ ID NO:12], Tyr-Ala-Arg-Ala-Ala-Arg-Arg-Ala-Ala-Arg-Arg [SEQ ID NO:13], Tyr-Ala-Arg-Ala-Ala-Arg-Arg-Ala-Ala-Arg-Ala [SEQ ID NO:14], Arg-Gln-Ile-Lys-Ile-Trp-Phe-Gln-Asn-Arg-Arg-Met-Lys-Trp-Lys-Lys [SEQ ID NO:15], Arg-Gln-Ile-Lys-Ile-Trp-Phe-Pro-Asn-Arg-Arg-Met-Lys-Trp-Lys-Lys [SEQ ID NO:16], Lys-Lys-Trp-Lys-Met-Arg-Arg-Asn-Gln-Phe-Trp-Val-Lys-Val-Gln-Arg [SEQ ID NO:17], Arg-Arg-Trp-Arg-Arg-Trp-Trp-Arg-Arg-Trp-Trp-Arg-Arg-Trp-Arg-Arg [SEQ ID NO:18], Arg-Arg-Met-Lys-Trp-Lys-Lys [SEQ ID NO:19], Apa-Arg-Gln-Ile-Lys-Ile-Trp-Phe-Gln-Asn-Arg-Arg-Met-Lys-Trp-Lys-Lys [SEQ ID NO:20], Apa-Arg-Gln-Ile-Lys-Ile-Trp-Phe-Pro-Asn-Arg-Arg-Met-Lys-Trp-Lys-Lys [SEQ ID NO:21], Arg-Arg-Arg-Arg-Arg-Arg-Arg [SEQ ID NO:22], Arg-Arg-Arg-Arg-Arg-Arg-Arg-Arg [SEQ ID NO:23], Asp-Ala-Ala-Thr-Arg-Ser-Ala-Ala-Ser-Arg-Pro-Thr-Glu-Arg-Pro-Arg-Ala-Pro-Ala-Arg-Ser-Ala-Ser-Arg-Pro-Arg-Arg-Pro-Val-Glu [SEQ ID NO:24], Gly-Ala-Leu-Phe-Leu-Gly-Trp-Leu-Gly-Ala-Ala-Gly-Ser-Thr-Met-Gly [SEQ ID NO:25], Gly-Ala-Leu-Phe-Leu-Gly-Phe-Leu-Gly-Ala-Ala-Gly-Ser-Thr-Met-Gly-Ala-Trp-Ser-Gln-Pro-Lys-Ser-Lys-Arg-Lys-Val [SEQ ID NO:26], Met-Gly-Leu-Gly-Leu-His-Leu-Leu-Val-Leu-Ala-Ala-Ala-Leu-Gln-Gly-Ala-Trp-Ser-Gln-Pro-Lys-Lys-Lys-Arg-Lys-Val [SEQ ID NO:27], Pro-Leu-Ser-Ser-Ile-Phe-Ser-Arg-Ile-Gly-Asp-Pro [SEQ ID NO:28], Phe-Trp-Arg-Gly-Asp-Leu-Val-Phe-Asp-Phe-Gln-Val [SEQ ID NO:29], Lys-Phe-Thr-Ile-Val-Phe-Pro-His-Asn-Gln-Lys-Gly-Asn-Trp-Lys-Asn-Val-Pro-Ser-Asn-Tyr-His-Tyr-Cys-Pro [SEQ ID NO:30], Ala-Lys-Arg-Ala-Arg-Leu-Ser-Thr-Ser-Phe-Asn-Pro-Val-Tyr-Pro-Tyr-Glu-Asp-Glu-Ser [SEQ ID NO:31], Gly-Trp-Thr-Leu-Asn-Ser-Ala-Gly-Tyr-Leu-Leu-Gly-Lys-Ile-Asn-Leu-Lys-Ala-Leu-Ala-Ala-Leu-Ala-Lys-Lys-Ile-Leu [SEQ ID NO:32], Arg-Gly-Gly-Arg-Leu-Ser-Tyr-Ser-Arg-Arg-Arg-Phe-Ser-Thr-Ser-Thr-Gly-Arg [SEQ ID NO:33], Ala-Ala-Val-Ala-Leu-Leu-Pro-Ala-Val-Leu-Leu-Ala-Leu-Leu-Ala-Pro [SEQ ID NO:34], Ala-Ala-Val-Leu-Leu-Pro-Val-Leu-Leu-Ala-Ala-Pro [SEQ ID NO:35], Val-Thr-Val-Leu-Ala-Leu-Gly-Ala-Leu-Ala-Gly-Val-Gly-Val-Gly [SEQ ID NO:36], Val-Ala-Tyr-Ile-Ser-Arg-Gly-Gly-Val-Ser-Thr-Tyr-Tyr-Ser-Asp-Thr-Val-Lys-Gly-Arg-Phe-Thr-Arg-Gln-Lys-Tyr-Asn-Lys-Arg-Ala [SEQ ID NO:37], Lys-Leu-Ala-Leu-Lys-Leu-Ala-Leu-Lys-Ala-Leu-Lys-Ala-Ala-Leu-Lys-Leu-Ala [SEQ ID NO:38], Trp-Glu-Ala-Lys-Leu-Ala-Lys-Ala-Leu-Ala-Lys-Ala-Leu-Ala-Lys-His-Leu-Ala-Lys-Ala-Leu-Ala-Lys-Ala-Leu-Lys-Ala-Cys-Glu-Ala [SEQ ID NO:39], Arg-Arg-Gln-Arg-Arg-Thr-Ser-Lys-Leu-Met-Lys-Arg [SEQ ID NO:40] and Val-Asp-Lys-Gly-Ser-Tyr-Leu-Pro-Arg-Pro-Thr (NAcGal)-Pro-Pro-Arg-Pro-Ile-Tyr-Asn-Arg-Asn [SEQ ID NO:41].

7. The compound of claim 5, or a salt thereof, wherein -M- consists of an amino acid or peptide.

8. The compound of claim 5, or a salt thereof, wherein -M- consists of a single bond.

9. The compound of claim 1, or a salt thereof, wherein Xaa$_2$ is selected from the group consisting Ser, Ser(α-Glc), Ser(β-Glc), Ser(α-Gal), Ser(β-Gal), Ser(α-GlcNAc), Ser (β-GlcNAc), Ser(α-GalNAc), Ser(β-GalNAc), Ser(α-Man), Ser(β-Man), Ser(α-ManNAc), Ser(β-ManNAc), Ser(α-[Gal-β(1→4)-Glc)]), Ser(α-[GalNAc-β(1→4)-Glc]), Ser(β-[Gal-NAc-β(1→4)-Glc]), Ser(β-[GalNAc-β(1→4)-GlcNAc]), Ser (β-[Gal-β(1→4)-Glc]), Ser(β-[Gal-β(1→4)-GlcNAc]), Ser (α-[Glc-α(1→4)-Glc]), Ser(β-[Glc-α(1→4)-Glc]), Ser(β-[Glc-α(1→4)-GlcNAc]), Ser(α-[Glc-β(1→4)-Glc]), Ser(β-[Glc-β(1→4)-Glc]), Ser(β-[Glc-β(1→4)-GlcNAc]), Ser(α-[GlcNAc-β(1→4)-Glc]), Ser(β-[GlcNAc-β(1→4)-Glc]), and Ser(β-[GlcNAc-β(1→4)-Glc]).

10. The compound of claim 9, or a salt thereof, wherein Xaa$_2$ is selected from the group consisting Ser, Ser(α-Glc), Ser(β-Glc), Ser(α-Gal), Ser(β-Gal), Ser(α-GlcNAc), Ser(β-GlcNAc), Ser(α-GalNAc), and Ser(β-GalNAc).

11. The compound of claim 10, or a salt thereof, wherein Xaa$_2$ is Ser.

12. The compound of claim 1, or a salt thereof, wherein Xaa$_3$ is selected from the group consisting of Thr, Thr(α-Glc), Thr(β-Glc), Thr(α-Gal), Thr(β-Gal), Thr(α-GlcNAc), Thr(β-GlcNAc), Thr(α-GalNAc), Thr(β-GalNAc), Thr(α-Man), Thr(β-Man), Thr(α-ManNAc), Thr(β-ManNAc), Thr(α-[Gal-β(1→4)-Glc]), Thr(α-[GalNAc-β(1→4)-Glc]), Thr(β-[GalNAc-β(1→4)-Glc]), Thr(β-[GalNAc-β(1→4)-GlcNAc]), Thr(β-[Gal-β(1→4)-Glc]), Thr(β-[Gal-β(1→4)-GlcNAc]), Thr(α-[Glc-α(1→4)-Glc]), Thr(β-[Glc-α(1→4)-Glc]), Thr(β-[Glc-α(1→4)-GlcNAc]), Thr(α-[Glc β(1→4)-Glc]), Thr(β-[Glc-β(1→4)-Glc]), Thr(β-[Glc-β(1→4)-GlcNAc]), Thr(α-[GlcNAc-β(1→4)-Glc]), Thr(β-[GlcNAc-β(1→4)-Glc]), and Thr(β-[GlcNAc-β(1→4)-Glc]).

13. The compound of claim 12, or a salt thereof, wherein Xaa$_3$ is selected from the group consisting of Thr, Thr(α-Glc), Thr(β-Glc), Thr(α-Gal), Thr(β-Gal), Thr(α-GlcNAc), Thr(β-GlcNAc), Thr(α-GalNAc), and Thr(β-GalNAc).

14. The compound of claim 13, wherein Xaa$_3$ is Thr(α-GalNAc).

15. The compound of claim 1, or a salt thereof, wherein Xaa$_4$ is Arg.

16. The compound of claim 1, or a salt thereof, wherein Xaa$_5$ is selected from the group consisting of Acp, AcpNH$_2$, bAla and bAlaNH$_2$.

17. The compound of claim 16, or a salt thereof, wherein Xaa$_5$ is selected from the group consisting of Acp and AcpNH$_2$.

18. The compound of claim 1, or a salt thereof, wherein said compound is selected from the group consisting of Tyr(I$_2$)-Ser-Thr(α-GalNAc)-Glu-Val-Val-Ala-Leu-Ser-Arg-Acp [SEQ ID NO:3], and Tyr(I$_2$)-Ser-Thr(α-GalNAc)-Glu-Val-Val-Ala-Leu-Ser-Arg-AcpNH$_2$ [SEQ ID NO:4].

19. A pharmaceutical composition comprising a compound according to Formula (I):

$$X^1\text{-M-SEQ ID NO:2} \qquad (I)$$

or a salt thereof, wherein:

SEQ ID NO:2 represents Xaa$_1$-Xaa$_2$-Xaa$_3$-Glu-Val-Val-Ala-Leu-Ser-Xaa$_4$-Xaa$_5$, wherein:

Xaa$_1$ is Tyr, Tyr(Me), Tyr(N-Me), Tyr(Me, N-Me), Tyr (I) or Tyr(I$_2$);

Xaa$_2$ is Ser or a saccharide-modified serine;

Xaa$_3$ is Thr or a saccharide-modified threonine;

Xaa$_4$ is Arg or Arg(N-Me);

Xaa$_5$ is a non-natural amino acid selected from the group consisting of a D-isomer of a natural amino acid, arginosuccinic acid, citrulline, cysteine sulfinic acid, 3,4-dihydroxyphenylalanine, homocysteine, homoserine, ornithine, 3-monoiodotyrosine, 3,5-diiodotyrosine, 3,5,5'-triiodothyronine, 3,3',5,5'-tetraiodothyronine, hydroxylysine, 4-hydroxyproline, an N-Cbz-protected amino acid, 2,4-diaminobutyric acid, homoarginine, N-methyl-arginine, norleucine, N-methylaminobutyric acid, naphthylalanine, phenylglycine, beta-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, Acp, AcpNH$_2$, bAla, bAlaNH$_2$, trans-4-(aminomethyl)-cyclohexanecarboxylic acid, 2-(aminomethyl)-benzoic acid, 3-(aminomethyl)-benzoic acid, 4-(aminomethyl)-benzoic acid, 1-aminocyclopentanecarboxylic acid, 1-aminocyclopropanecarboxylic acid, and 2-benzyl-5-aminopentanoic acid; and, X1-M is an optional group comprising a tagging element conjugated to the N-terminus of the amino acid sequence SEQ ID NO:2, wherein:
  X1 is the tagging element, wherein the tagging element is selected from the group consisting of a transduction domain and a detection label; and,
  -M- is a single bond or an optional linking group forming a covalent linkage between the tagging element and the amino acid sequence SEQ ID NO:2;
and a pharmaceutically acceptable carrier.

20. The pharmaceutical composition of claim 19, wherein Xaa$_1$ is Tyr(Me), Tyr(N-Me), Tyr(Me, N-Me), Tyr(I) or Tyr(I$_2$).

21. The pharmaceutical composition of claim 19, wherein said compound is selected from the group consisting of consisting of Tyr(I$_2$)-Ser-Thr(α-GalNAc)-Glu-Val-Val-Ala-Leu-Ser-Arg-Acp [SEQ ID NO:3], and Tyr(I$_2$)-Ser-Thr(α-GalNAc)-Glu-Val-Val-Ala-Leu-Ser-Arg-AcpNH$_2$ [SEQ ID NO:4], and salts thereof.

22. A method of treating lipodystrophy in a subject in need thereof, said method comprising administering to said subject a therapeutically effective amount of a pharmaceutical formulation comprising a compound of Formula (I):

$$X^1\text{-M-SEQ ID NO:2} \tag{I}$$

or a salt thereof, wherein:
  SEQ ID NO:2 represents Xaa$_1$-Xaa$_2$-Xaa$_3$-Glu-Val-Val-Ala-Leu-Ser-Xaa$_4$-Xaa$_5$,
  wherein:
    Xaa$_1$ is Tyr, Tyr(Me), Tyr(N-Me), Tyr(Me, N-Me), Tyr(I) or Tyr(I$_2$);
    Xaa$_2$ is Ser or a saccharide-modified serine;
    Xaa$_3$ is Thr or a saccharide-modified threonine;
    Xaa$_4$ is Arg or Arg(N-Me);
    Xaa$_5$ is a non-natural amino acid selected from the group consisting of a D-isomer of a natural amino acid, arginosuccinic acid, citrulline, cysteine sulfinic acid, 3,4-dihydroxyphenylalanine, homocysteine, homoserine, ornithine, 3-monoiodotyrosine, 3,5-diiodotyrosine, 3,5,5'-triiodothyronine, 3,3',5,5'-tetraiodothyronine, hydroxylysine, 4-hydroxyproline, an N-Cbz-protected amino acid, 2,4-diaminobutyric acid, homoarginine, N-methyl-arginine, norleucine, N-methylaminobutyric acid, naphthylalanine, phenylglycine, beta-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, Acp, AcpNH$_2$, bAla, bAlaNH$_2$, trans-4-(aminomethyl)-cyclohexanecarboxylic acid, 2-(aminomethyl)-benzoic acid, 3-(aminomethyl)-benzoic acid, 4-(aminomethyl)-benzoic acid, 1-aminocyclopentanecarboxylic acid, 1-aminocyclopropanecarboxylic acid, and 2-benzyl-5-aminopentanoic acid; and, X1-M is an optional group comprising a tagging element conjugated to the N-terminus of the amino acid sequence SEQ ID NO:2, wherein:
  X1 is the tagging element, wherein the tagging element is selected from the group consisting of a transduction domain and a detection label; and,
  -M- is a single bond or an optional linking group forming a covalent linkage between the tagging element and the amino acid sequence SEQ ID NO:2.

23. The method of claim 22, wherein Xaa$_1$ is Tyr(Me), Tyr(N-Me), Tyr(Me, N-Me), Tyr(I) or Tyr(I$_2$).

24. The method of claim 22, wherein said compound is selected from the group consisting of consisting of Tyr(I$_2$)-Ser-Thr(α-GalNAc)-Glu-Val-Val-Ala-Leu-Ser-Arg-Acp [SEQ ID NO:3], and Tyr(I$_2$)-Ser-Thr(α-GalNAc)-Glu-Val-Val-Ala-Leu-Ser-Arg-AcpNH$_2$ [SEQ ID NO:4], and salts thereof.

25. A method of treating infertility in a subject in need thereof, said method comprising administering to said subject a therapeutically effective amount of a pharmaceutical formulation comprising a compound of Formula (I):

$$X^1\text{-M-SEQ ID NO:2} \tag{I}$$

or a salt thereof, wherein:
  SEQ ID NO:2 represents Xaa$_1$-Xaa$_2$-Xaa$_3$-Glu-Val-Val-Ala-Leu-Ser-Xaa$_4$-Xaa$_5$,
  wherein:
    Xaa$_1$ is Tyr, Tyr(Me), Tyr(N-Me), Tyr(Me, N-Me), Tyr(I) or Tyr(I$_2$);
    Xaa$_2$ is Ser or a saccharide-modified serine;
    Xaa$_3$ is Thr or a saccharide-modified threonine;
    Xaa$_4$ is Arg or Arg(N-Me);
    Xaa$_5$ is a non-natural amino acid selected from the group consisting of a D-isomer of a natural amino acid, arginosuccinic acid, citrulline, cysteine sulfinic acid, 3,4-dihydroxyphenylalanine, homocysteine, homoserine, ornithine, 3-monoiodotyrosine, 3,5-diiodotyrosine, 3,5,5'-triiodothyronine, 3,3',5,5'-tetraiodothyronine, hydroxylysine, 4-hydroxyproline, an N-Cbz-protected amino acid, 2,4-diaminobutyric acid, homoarginine, N-methyl-arginine, norleucine, N-methylaminobutyric acid, naphthylalanine, phenylglycine, beta-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, Acp, AcpNH$_2$, bAla, bAlaNH$_2$, trans-4-(aminomethyl)-cyclohexanecarboxylic acid, 2-(aminomethyl)-benzoic acid, 3-(aminomethyl)-benzoic acid, 4-(aminomethyl)-benzoic acid, 1-aminocyclopentanecarboxylic acid, 1-aminocyclopropanecarboxylic acid, and 2-benzyl-5-aminopentanoic acid; and, X1-M is an optional group comprising a tagging element conjugated to the N-terminus of the amino acid sequence SEQ ID NO:2, wherein:
  X1 is the tagging element, wherein the tagging element is selected from the group consisting of a transduction domain and a detection label; and,
  -M- is a single bond or an optional linking group forming a covalent linkage between the tagging element and the amino acid sequence SEQ ID NO:2;
wherein said infertility is selected from the group consisting of obesity-related infertility, lipodystrophy-related infertility, and infertility associated with polycystic ovarian syndrome.

26. The method of claim 25, wherein Xaa$_1$ is Tyr(Me), Tyr(N-Me), Tyr(Me, N-Me), Tyr(I) or Tyr(I$_2$).

27. The method of claim 25, wherein said compound is selected from the group consisting of consisting of Tyr(I$_2$)-Ser-Thr(α-GalNAc)-Glu-Val-Val-Ala-Leu-Ser-Arg-Acp [SEQ ID NO:31, and Tyr(I$_2$)-Ser-Thr(α-GalNAc)-Glu-Val-Val-Ala-Leu-Ser-Arg-AcpNH$_2$ [SEQ ID NO:4], and salts thereof.

28. A method of treating obesity in a subject in need thereof, said method comprising administering to said subject a therapeutically effective amount of a pharmaceutical formulation comprising a compound of Formula (I):

$$X^1\text{-M-SEQ ID NO:2} \quad (I)$$

or a salt thereof, wherein:
SEQ ID NO:2 represents Xaa$_1$-Xaa$_2$-Xaa$_3$-Glu-Val-Val-Ala-Leu-Ser-Xaa$_4$-Xaa$_5$,
wherein:
Xaa$_1$ is Tyr, Tyr(Me), Tyr(N-Me), Tyr(Me, N-Me), Tyr (I) or Tyr(I$_2$);
Xaa$_2$ is Ser or a saccharide-modified serine;
Xaa$_3$ is Thr or a saccharide-modified threonine;
Xaa$_4$ is Arg or Arg(N-Me);
Xaa$_5$ is a non-natural amino acid selected from the group consisting of a D-isomer of a natural amino acid, arginosuccinic acid, citrulline, cysteine sulfinic acid, 3,4-dihydroxyphenylalanine, homocysteine, homoserine, ornithine, 3-monoiodotyrosine, 3,5-diiodotyrosine, 3,5,5'-triiodothyronine, 3,3',5,5'-tetraiodothyronine, hydroxylysine, 4-hydroxyproline, an N-Cbz-protected amino acid, 2,4-diaminobutyric acid, homoarginine, N-methyl-arginine, norleucine, N-methylaminobutyric acid, naphthylalanine, phenylglycine, beta-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, Acp, AcpNH$_2$, bAla, bAlaNH$_2$, trans-4-(aminomethyl)-cyclohexanecarboxylic acid, 2-(aminomethyl)-benzoic acid, 3-(aminomethyl)-benzoic acid, 4-(aminomethyl)-benzoic acid, 1-aminocyclopentanecarboxylic acid, 1-aminocyclopropanecarboxylic acid, and 2-benzyl-5-aminopentanoic acid; and,
X1-M is an optional group comprising a tagging element conjugated to the N-terminus of the amino acid sequence SEQ ID NO:2, wherein:
X1 is the tagging element, wherein the tagging element is selected from the group consisting of a transduction domain and a detection label; and,
-M- represents is a single bond or an optional linking group forming a covalent linkage between the tagging element and the amino acid sequence SEQ ID NO:2.

29. The method of claim 28, wherein Xaa$_1$ is Tyr(Me), Tyr(N-Me), Tyr(Me, N-Me), Tyr(I) or Tyr(I$_2$).

30. The method of claim 28, wherein said compound is selected from the group consisting of consisting of Tyr(I$_2$)-Ser-Thr(α-GalNAc)-Glu-Val-Val-Ala-Leu-Ser-Arg-Acp [SEQ ID NO:3], and Tyr(I$_2$)-Ser-Thr(α-GalNAc)-Glu-Val-Val-Ala-Leu-Ser-Arg-AcpNH$_2$ [SEQ ID NO:4], and salts thereof.

31. A method of treating metabolic syndrome in a subject in need thereof, said method comprising administering to said subject a therapeutically effective amount of a pharmaceutical formulation comprising a compound of Formula (I):

$$X^1\text{-M-SEQ ID NO:2} \quad (I)$$

or a salt thereof, wherein:
SEQ ID NO:2 represents Xaa$_1$-Xaa$_2$-Xaa$_3$-Glu-Val-Val-Ala-Leu-Ser-Xaa$_4$-Xaa$_5$,
wherein:
Xaa$_1$ is Tyr, Tyr(Me), Tyr(N-Me), Tyr(Me, N-Me), Tyr (I) or Tyr(I$_2$);
Xaa$_2$ is Ser or a saccharide-modified serine;
Xaa$_3$ is Thr or a saccharide-modified threonine;
Xaa$_4$ is Arg or Arg(N-Me);
Xaa$_5$ is a non-natural amino acid selected from the group consisting of a D-isomer of a natural amino acid, arginosuccinic acid, citrulline, cysteine sulfinic acid, 3,4-dihydroxyphenylalanine, homocysteine, homoserine, ornithine, 3-monoiodotyrosine, 3,5-diiodotyrosine, 3,5,5'-triiodothyronine, 3,3',5,5'-tetraiodothyronine, hydroxylysine, 4-hydroxyproline, an N-Cbz-protected amino acid, 2,4-diaminobutyric acid, homoarginine, N-methyl-arginine, norleucine, N-methylaminobutyric acid, naphthylalanine, phenylglycine, beta-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, Acp, AcpNH$_2$, bAla, bAlaNH$_2$, trans-4-(aminomethyl)-cyclohexanecarboxylic acid, 2-(aminomethyl)-benzoic acid, 3-(aminomethyl)-benzoic acid, 4-(aminomethyl)-benzoic acid, 1-aminocyclopentanecarboxylic acid, 1-aminocyclopropanecarboxylic acid, and 2-benzyl-5-aminopentanoic acid; and,
X1-M is an optional group comprising a tagging element conjugated to the N-terminus of the amino acid sequence SEQ ID NO:2, wherein:
X1 is the tagging element, wherein the tagging element is selected from the group consisting of a transduction domain and a detection label; and,
-M- is a single bond or an optional linking group forming a covalent linkage between the tagging element and the amino acid sequence SEQ ID NO:2.

32. The method of claim 31, wherein Xaa$_1$ is Tyr(Me), Tyr(N-Me), Tyr(Me, N-Me), Tyr(I) or Tyr(I$_2$).

33. The method of claim 31, wherein said compound is selected from the group consisting of consisting of Tyr(I$_2$)-Ser-Thr(α-GalNAc)-Glu-Val-Val-Ala-Leu-Ser-Arg-Acp [SEQ ID NO:3], and Tyr(I$_2$)-Ser-Thr(α-GalNAc)-Glu-Val-Val-Ala-Leu-Ser-Arg-AcpNH$_2$ [SEQ ID NO:4], and salts thereof.

34. A method of treating hypothalamic amenorrhea in a subject in need thereof, said method comprising administering to said subject a therapeutically effective amount of a pharmaceutical formulation comprising a compound of Formula (I):

$$X^1\text{-M-SEQ ID NO:2} \quad (I)$$

or a salt thereof, wherein:
SEQ ID NO:2 represents Xaa$_1$-Xaa$_2$-Xaa$_3$-Glu-Val-Val-Ala-Leu-Ser-Xaa$_4$-Xaa$_5$,
wherein:
Xaa$_1$ is Tyr, Tyr(Me), Tyr(N-Me), Tyr(Me, N-Me), Tyr (I) or Tyr(I$_2$);
Xaa$_2$ is Ser or a saccharide-modified serine;
Xaa$_3$ is Thr or a saccharide-modified threonine;
Xaa$_4$ is Arg or Arg(N-Me);
Xaa$_5$ is a non-natural amino acid selected from the group consisting of a D-isomer of a natural amino acid, arginosuccinic acid, citrulline, cysteine sulfinic acid, 3,4-dihydroxyphenylalanine, homocysteine, homoserine, ornithine, 3-monoiodotyrosine, 3,5-diiodotyrosine, 3,5,5'-triiodothyronine, 3,3',5,5'-tetraiodothyronine, hydroxylysine, 4-hydroxyproline, an N-Cbz-protected amino acid, 2,4-diaminobutyric acid, homoarginine, N-methyl-arginine, norleucine, N-methylaminobutyric acid, naphthylalanine, phenylglycine, beta-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, Acp, AcpNH$_2$, bAla, bAlaNH$_2$, trans-4-(aminomethyl)-cyclohexanecarboxylic acid, 2-(aminomethyl)-benzoic acid, 3-(aminomethyl)-benzoic acid, 4-(aminomethyl)-benzoic acid, 1-aminocyclopentanecarboxylic acid, 1-aminocyclopropanecarboxylic acid, and 2-benzyl-5-aminopentanoic acid; and, X1-M is an optional group comprising a tagging element conjugated to the N-terminus of the amino acid sequence SEQ ID NO:2, wherein:

X1 is the tagging element, wherein the tagging element is selected from the group consisting of a transduction domain and a detection label; and, -M- is a single bond or an optional linking group forming a covalent linkage between the tagging element and the amino acid sequence SEQ ID NO:2.

35. The method of claim 34, wherein Xaa$_1$ is Tyr(Me), Tyr(N-Me), Tyr(Me, N-Me), Tyr(I) or Tyr(I$_2$).

36. The method of claim 34, wherein said compound is selected from the group consisting of consisting of Tyr(I$_2$)-Ser-Thr(α-GalNAc)-Glu-Val-Val-Ala-Leu-Ser-Arg-Acp [SEQ ID NO:3], and Tyr(I$_2$)-Ser-Thr(α-GalNAc)-Glu-Val-Val-Ala-Leu-Ser-Arg-AcpNH$_2$ [SEQ ID NO:4], and salts thereof.

37. A method of treating insulin resistance in a subject in need thereof, said method comprising administering to said subject a therapeutically effective amount of a pharmaceutical formulation comprising a compound of Formula (I):

$$X^1\text{-M-SEQ ID NO:2} \quad (I)$$

or a salt thereof, wherein:

SEQ ID NO:2 represents Xaa$_1$-Xaa$_2$-Xaa$_3$-Glu-Val-Val-Ala-Leu-Ser-Xaa$_4$-Xaa$_5$, wherein:

Xaa$_1$ is Tyr, Tyr(Me), Tyr(N-Me), Tyr(Me, N-Me), Tyr(I) or Tyr(I$_2$);

Xaa$_2$ is Ser or a saccharide-modified serine;

Xaa$_3$ is Thr or a saccharide-modified threonine;

Xaa$_4$ is Arg or Arg(N-Me);

Xaa$_5$ is a non-natural amino acid selected from the group consisting of a D-isomer of a natural amino acid, arginosuccinic acid, citrulline, cysteine sulfinic acid, 3,4-dihydroxyphenylalanine, homocysteine, homoserine, ornithine, 3-monoiodotyrosine, 3,5-diiodotyrosine, 3,5,5'-triiodothyronine, 3,3',5,5'-tetraiodothyronine, hydroxylysine, 4-hydroxyproline, an N-Cbz-protected amino acid, 2,4-diaminobutyric acid, homoarginine, N-methyl-arginine, norleucine, N-methylaminobutyric acid, naphthylalanine, phenylglycine, beta-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, Acp, AcpNH$_2$, bAla, bAlaNH$_2$, trans-4-(aminomethyl)-cyclohexanecarboxylic acid, 2-(aminomethyl)-benzoic acid, 3-(aminomethyl)-benzoic acid, 4-(aminomethyl)-benzoic acid, 1-aminocyclopentanecarboxylic acid, 1-aminocyclopropanecarboxylic acid, and 2-benzyl-5-aminopentanoic acid; and, X1-M is an optional group comprising a tagging element conjugated to the N-terminus of the amino acid sequence SEQ ID NO:2, wherein:

X1 is the tagging element, wherein the tagging element is selected from the group consisting of a transduction domain and a detection label; and, -M- is a single bond or an optional linking group forming a covalent linkage between the tagging element and the amino acid sequence SEQ ID NO:2.

38. The method of claim 37, wherein Xaa$_1$ is Tyr(Me), Tyr(N-Me), Tyr(Me, N-Me), Tyr(I) or Tyr(I$_2$).

39. The method of claim 37, wherein said compound is selected from the group consisting of consisting of Tyr(I$_2$)-Ser-Thr(α-GalNAc)-Glu-Val-Val-Ala-Leu-Ser-Arg-Acp [SEQ ID NO:3], and Tyr(I$_2$)-Ser-Thr(α-GalNAc)-Glu-Val-Val-Ala-Leu-Ser-Arg-AcpNH$_2$ [SEQ ID NO:4], and salts thereof.

* * * * *

SEQUENCE LISTING

```
<160> NUMBER OF SEQ ID NOS: 42

<210> SEQ ID NO 1
<211> LENGTH: 167
<212> TYPE: PRT
<213> ORGANISM: Homo sapiens

<400> SEQUENCE: 1

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
            20                  25                  30

Thr Leu Ile Lys Thr Ile Val Thr Arg Ile Asn Asp Ile Ser His Thr
        35                  40                  45

Gln Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
                85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
    130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 2
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (1)..(1)
<223> OTHER INFORMATION: tyrosine;  2-amino-3-(4-methoxyphenyl)propanoic
      acid;  3-(4-hydroxyphenyl)-2-(methylamino)propanoic acid;
```

3-(4-methoxyphenyl)-2-(methylamino)propanoic acid;
3-monoiodotyrosine; or 3,5-diiodotyrosine
<220> FEATURE:
<221> NAME/KEY: MOD_RES
<222> LOCATION: (2)..(2)
<223> OTHER INFORMATION: Ser or a saccharide-modified serine
<220> FEATURE:
<221> NAME/KEY: MOD_RES
<222> LOCATION: (3)..(3)
<223> OTHER INFORMATION: Thr or a saccharide-modified threonine
<220> FEATURE:
<221> NAME/KEY: MOD_RES
<222> LOCATION: (10)..(10)
<223> OTHER INFORMATION: Arg or 5-guanidino-2-(methylamino)pentanoic
      acid
<220> FEATURE:
<221> NAME/KEY: MOD_RES
<222> LOCATION: (11)..(11)
<223> OTHER INFORMATION: a non-natural amino acid

<400> SEQUENCE: 2

Xaa Xaa Xaa Glu Val Val Ala Leu Ser Xaa Xaa
1               5                   10

<210> SEQ ID NO 3
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (1)..(1)
<223> OTHER INFORMATION: 3,5-diiodotyrosine
<220> FEATURE:
<221> NAME/KEY: MOD_RES
<222> LOCATION: (3)..(3)
<223> OTHER INFORMATION: O-alpha-(N-acetyl-galactosyl) threonine
<220> FEATURE:
<221> NAME/KEY: MOD_RES
<222> LOCATION: (11)..(11)
<223> OTHER INFORMATION: Acp

<400> SEQUENCE: 3

Xaa Ser Xaa Glu Val Val Ala Leu Ser Arg Xaa
1               5                   10

<210> SEQ ID NO 4
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (1)..(1)
<223> OTHER INFORMATION: 3,5-diiodotyrosine
<220> FEATURE:
<221> NAME/KEY: MOD_RES
<222> LOCATION: (3)..(3)
<223> OTHER INFORMATION: O-alpha-(N-acetyl-galactosyl) threonine
<220> FEATURE:
<221> NAME/KEY: MOD_RES
<222> LOCATION: (11)..(11)
<223> OTHER INFORMATION: AcpNH2 (6-aminocapramide)

<400> SEQUENCE: 4

Xaa Ser Xaa Glu Val Val Ala Leu Ser Arg Xaa
1               5                   10

<210> SEQ ID NO 5
<211> LENGTH: 11
<212> TYPE: PRT

```
<213> ORGANISM: Artificial Sequence
<220> FEATURE:
<223> OTHER INFORMATION: chemically synthesized

<400> SEQUENCE: 5

Tyr Gly Arg Lys Lys Arg Arg Gln Arg Arg
1               5                   10

<210> SEQ ID NO 6
<211> LENGTH: 9
<212> TYPE: PRT
<213> ORGANISM: Artificial Sequence
<220> FEATURE:
<223> OTHER INFORMATION: chemically synthesized

<400> SEQUENCE: 6

Arg Lys Lys Arg Arg Gln Arg Arg Arg
1               5

<210> SEQ ID NO 7
<211> LENGTH: 14
<212> TYPE: PRT
<213> ORGANISM: Artificial Sequence
<220> FEATURE:
<223> OTHER INFORMATION: chemically synthesized

<400> SEQUENCE: 7

Gly Arg Lys Lys Arg Arg Gln Arg Arg Arg Gly Tyr Lys Cys
1               5                   10

<210> SEQ ID NO 8
<211> LENGTH: 12
<212> TYPE: PRT
<213> ORGANISM: Artificial Sequence
<220> FEATURE:
<223> OTHER INFORMATION: chemically synthesized

<400> SEQUENCE: 8

Tyr Gly Arg Lys Lys Arg Arg Gln Arg Arg Gly
1               5                   10

<210> SEQ ID NO 9
<211> LENGTH: 14
<212> TYPE: PRT
<213> ORGANISM: Artificial Sequence
<220> FEATURE:
<223> OTHER INFORMATION: chemically synthesized

<400> SEQUENCE: 9

Gly Arg Lys Lys Arg Arg Gln Arg Arg Arg Pro Pro Gln Cys
1               5                   10

<210> SEQ ID NO 10
<211> LENGTH: 13
<212> TYPE: PRT
<213> ORGANISM: Artificial Sequence
<220> FEATURE:
<223> OTHER INFORMATION: chemically synthesized

<400> SEQUENCE: 10

Gly Arg Lys Lys Arg Arg Gln Arg Arg Arg Pro Pro Gln
1               5                   10

<210> SEQ ID NO 11
<211> LENGTH: 11
<212> TYPE: PRT
<213> ORGANISM: Artificial Sequence
```

<220> FEATURE:
<223> OTHER INFORMATION: chemically synthesized

<400> SEQUENCE: 11

Tyr Ala Arg Lys Ala Arg Arg Gln Ala Arg Arg
1               5                   10

<210> SEQ ID NO 12
<211> LENGTH: 11
<212> TYPE: PRT
<213> ORGANISM: Artificial Sequence
<220> FEATURE:
<223> OTHER INFORMATION: chemically synthesized

<400> SEQUENCE: 12

Tyr Ala Arg Ala Ala Ala Arg Gln Ala Arg Ala
1               5                   10

<210> SEQ ID NO 13
<211> LENGTH: 11
<212> TYPE: PRT
<213> ORGANISM: Artificial Sequence
<220> FEATURE:
<223> OTHER INFORMATION: chemically synthesized

<400> SEQUENCE: 13

Tyr Ala Arg Ala Ala Arg Arg Ala Ala Arg Arg
1               5                   10

<210> SEQ ID NO 14
<211> LENGTH: 11
<212> TYPE: PRT
<213> ORGANISM: Artificial Sequence
<220> FEATURE:
<223> OTHER INFORMATION: chemically synthesized

<400> SEQUENCE: 14

Tyr Ala Arg Ala Ala Arg Arg Ala Ala Arg Ala
1               5                   10

<210> SEQ ID NO 15
<211> LENGTH: 16
<212> TYPE: PRT
<213> ORGANISM: Artificial Sequence
<220> FEATURE:
<223> OTHER INFORMATION: chemically synthesized

<400> SEQUENCE: 15

Arg Gln Ile Lys Ile Trp Phe Gln Asn Arg Arg Met Lys Trp Lys Lys
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: chemically synthesized

<400> SEQUENCE: 16

Arg Gln Ile Lys Ile Trp Phe Pro Asn Arg Arg Met Lys Trp Lys Lys
1               5                   10                  15

<210> SEQ ID NO 17
<211> LENGTH: 16
<212> TYPE: PRT
<213> ORGANISM: Artificial Sequence
<220> FEATURE:

```
<223> OTHER INFORMATION: chemically synthesized

<400> SEQUENCE: 17

Lys Lys Trp Lys Met Arg Arg Asn Gln Phe Trp Val Lys Val Gln Arg
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: chemically synthesized

<400> SEQUENCE: 18

Arg Arg Trp Arg Arg Trp Trp Arg Arg Trp Trp Arg Arg Trp Arg Arg
1               5                   10                  15

<210> SEQ ID NO 19
<211> LENGTH: 7
<212> TYPE: PRT
<213> ORGANISM: Artificial Sequence
<220> FEATURE:
<223> OTHER INFORMATION: chemically synthesized

<400> SEQUENCE: 19

Arg Arg Met Lys Trp Lys Lys
1               5

<210> SEQ ID NO 20
<211> LENGTH: 17
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (1)..(1)
<223> OTHER INFORMATION: aminopentanoic acid

<400> SEQUENCE: 20

Xaa Arg Gln Ile Lys Ile Trp Phe Gln Asn Arg Arg Met Lys Trp Lys
1               5                   10                  15

Lys

<210> SEQ ID NO 21
<211> LENGTH: 17
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (1)..(1)
<223> OTHER INFORMATION: aminopentanoic acid

<400> SEQUENCE: 21

Xaa Arg Gln Ile Lys Ile Trp Phe Pro Asn Arg Arg Met Lys Trp Lys
1               5                   10                  15

Lys

<210> SEQ ID NO 22
<211> LENGTH: 7
<212> TYPE: PRT
<213> ORGANISM: Artificial Sequence
<220> FEATURE:
<223> OTHER INFORMATION: chemically synthesized
```

```
<400> SEQUENCE: 22

Arg Arg Arg Arg Arg Arg Arg
1               5

<210> SEQ ID NO 23
<211> LENGTH: 9
<212> TYPE: PRT
<213> ORGANISM: Artificial Sequence
<220> FEATURE:
<223> OTHER INFORMATION: chemically synthesized

<400> SEQUENCE: 23

Arg Arg Arg Arg Arg Arg Arg Arg Arg
1               5

<210> SEQ ID NO 24
<211> LENGTH: 30
<212> TYPE: PRT
<213> ORGANISM: Artificial Sequence
<220> FEATURE:
<223> OTHER INFORMATION: chemically synthesized

<400> SEQUENCE: 24

Asp Ala Ala Thr Arg Ser Ala Ala Ser Arg Pro Thr Glu Arg Pro Arg
1               5                   10                  15

Ala Pro Ala Arg Ser Ala Ser Arg Pro Arg Arg Pro Val Glu
            20                  25                  30

<210> SEQ ID NO 25
<211> LENGTH: 16
<212> TYPE: PRT
<213> ORGANISM: Artificial Sequence
<220> FEATURE:
<223> OTHER INFORMATION: chemically synthesized

<400> SEQUENCE: 25

Gly Ala Leu Phe Leu Gly Trp Leu Gly Ala Ala Gly Ser Thr Met Gly
1               5                   10                  15

<210> SEQ ID NO 26
<211> LENGTH: 27
<212> TYPE: PRT
<213> ORGANISM: Artificial Sequence
<220> FEATURE:
<223> OTHER INFORMATION: chemically synthesized

<400> SEQUENCE: 26

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 27
<211> LENGTH: 27
<212> TYPE: PRT
<213> ORGANISM: Artificial Sequence
<220> FEATURE:
<223> OTHER INFORMATION: chemically synthesized

<400> SEQUENCE: 27

Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25
```

<210> SEQ ID NO 28
<211> LENGTH: 12
<212> TYPE: PRT
<213> ORGANISM: Artificial Sequence
<220> FEATURE:
<223> OTHER INFORMATION: chemically synthesized

<400> SEQUENCE: 28

Pro Leu Ser Ser Ile Phe Ser Arg Ile Gly Asp Pro
1               5                   10

<210> SEQ ID NO 29
<211> LENGTH: 12
<212> TYPE: PRT
<213> ORGANISM: Artificial Sequence
<220> FEATURE:
<223> OTHER INFORMATION: chemically synthesized

<400> SEQUENCE: 29

Phe Trp Arg Gly Asp Leu Val Phe Asp Phe Gln Val
1               5                   10

<210> SEQ ID NO 30
<211> LENGTH: 25
<212> TYPE: PRT
<213> ORGANISM: Artificial Sequence
<220> FEATURE:
<223> OTHER INFORMATION: chemically synthesized

<400> SEQUENCE: 30

Lys Phe Thr Ile Val Phe Pro His Asn Gln Lys Gly Asn Trp Lys Asn
1               5                   10                  15

Val Pro Ser Asn Tyr His Tyr Cys Pro
            20                  25

<210> SEQ ID NO 31
<211> LENGTH: 20
<212> TYPE: PRT
<213> ORGANISM: Artificial Sequence
<220> FEATURE:
<223> OTHER INFORMATION: chemically synthesized

<400> SEQUENCE: 31

Ala Lys Arg Ala Arg Leu Ser Thr Ser Phe Asn Pro Val Tyr Pro Tyr
1               5                   10                  15

Glu Asp Glu Ser
            20

<210> SEQ ID NO 32
<211> LENGTH: 27
<212> TYPE: PRT
<213> ORGANISM: Artificial Sequence
<220> FEATURE:
<223> OTHER INFORMATION: chemically synthesized

<400> SEQUENCE: 32

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 33
<211> LENGTH: 18
<212> TYPE: PRT
<213> ORGANISM: Artificial Sequence

```
<220> FEATURE:
<223> OTHER INFORMATION: chemically synthesized

<400> SEQUENCE: 33

Arg Gly Gly Arg Leu Ser Tyr Ser Arg Arg Phe Ser Thr Ser Thr
1               5                   10                  15

Gly Arg

<210> SEQ ID NO 34
<211> LENGTH: 16
<212> TYPE: PRT
<213> ORGANISM: Artificial Sequence
<220> FEATURE:
<223> OTHER INFORMATION: chemically synthesized

<400> SEQUENCE: 34

Ala Ala Val Ala Leu Leu Pro Ala Val Leu Leu Ala Leu Leu Ala Pro
1               5                   10                  15

<210> SEQ ID NO 35
<211> LENGTH: 12
<212> TYPE: PRT
<213> ORGANISM: Artificial Sequence
<220> FEATURE:
<223> OTHER INFORMATION: chemically synthesized

<400> SEQUENCE: 35

Ala Ala Val Leu Leu Pro Val Leu Leu Ala Ala Pro
1               5                   10

<210> SEQ ID NO 36
<211> LENGTH: 15
<212> TYPE: PRT
<213> ORGANISM: Artificial Sequence
<220> FEATURE:
<223> OTHER INFORMATION: chemically synthesized

<400> SEQUENCE: 36

Val Thr Val Leu Ala Leu Gly Ala Leu Ala Gly Val Gly Val Gly
1               5                   10                  15

<210> SEQ ID NO 37
<211> LENGTH: 30
<212> TYPE: PRT
<213> ORGANISM: Artificial Sequence
<220> FEATURE:
<223> OTHER INFORMATION: chemically synthesized

<400> SEQUENCE: 37

Val Ala Tyr Ile Ser Arg Gly Gly Val Ser Thr Tyr Tyr Ser Asp Thr
1               5                   10                  15

Val Lys Gly Arg Phe Thr Arg Gln Lys Tyr Asn Lys Arg Ala
            20                  25                  30

<210> SEQ ID NO 38
<211> LENGTH: 18
<212> TYPE: PRT
<213> ORGANISM: Artificial Sequence
<220> FEATURE:
<223> OTHER INFORMATION: chemically synthesized

<400> SEQUENCE: 38

Lys Leu Ala Leu Lys Leu Ala Leu Lys Ala Leu Lys Ala Ala Leu Lys
1               5                   10                  15

Leu Ala
```

```
<210> SEQ ID NO 39
<211> LENGTH: 30
<212> TYPE: PRT
<213> ORGANISM: Artificial Sequence
<220> FEATURE:
<223> OTHER INFORMATION: chemically synthesized

<400> SEQUENCE: 39

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 40
<211> LENGTH: 12
<212> TYPE: PRT
<213> ORGANISM: Artificial Sequence
<220> FEATURE:
<223> OTHER INFORMATION: chemically synthesized

<400> SEQUENCE: 40

Arg Arg Gln Arg Arg Thr Ser Lys Leu Met Lys Arg
1               5                   10

<210> SEQ ID NO 41
<211> LENGTH: 20
<212> TYPE: PRT
<213> ORGANISM: Artificial Sequence
<220> FEATURE:
<223> OTHER INFORMATION: chemically synthesized
<220> FEATURE:
<221> NAME/KEY: MOD_RES
<222> LOCATION: (11)..(11)
<223> OTHER INFORMATION: O-alpha-(N-acetyl-galactosyl)-Thr

<400> SEQUENCE: 41

Val Asp Lys Gly Ser Tyr Leu Pro Arg Pro Xaa Pro Pro Arg Pro Ile
1               5                   10                  15

Tyr Asn Arg Asn
            20

<210> SEQ ID NO 42
<211> LENGTH: 1165
<212> TYPE: PRT
<213> ORGANISM: Homo sapiens

<400> SEQUENCE: 42

Met Ile Cys Gln Lys Phe Cys Val Val Leu Leu His Trp Glu Phe Ile
1               5                   10                  15

Tyr Val Ile Thr Ala Phe Asn Leu Ser Tyr Pro Ile Thr Pro Trp Arg
            20                  25                  30

Phe Lys Leu Ser Cys Met Pro Pro Asn Ser Thr Tyr Asp Tyr Phe Leu
        35                  40                  45

Leu Pro Ala Gly Leu Ser Lys Asn Thr Ser Asn Ser Asn Gly His Tyr
    50                  55                  60

Glu Thr Ala Val Glu Pro Lys Phe Asn Ser Ser Gly Thr His Phe Ser
65                  70                  75                  80

Asn Leu Ser Lys Thr Thr Phe His Cys Cys Phe Arg Ser Glu Gln Asp
                85                  90                  95

Arg Asn Cys Ser Leu Cys Ala Asp Asn Ile Glu Gly Lys Thr Phe Val
            100                 105                 110
```

```
Ser Thr Val Asn Ser Leu Val Phe Gln Gln Ile Asp Ala Asn Trp Asn
            115                 120                 125

Ile Gln Cys Trp Leu Lys Gly Asp Leu Lys Leu Phe Ile Cys Tyr Val
130                 135                 140

Glu Ser Leu Phe Lys Asn Leu Phe Arg Asn Tyr Asn Tyr Lys Val His
145                 150                 155                 160

Leu Leu Tyr Val Leu Pro Glu Val Leu Glu Asp Ser Pro Leu Val Pro
                165                 170                 175

Gln Lys Gly Ser Phe Gln Met Val His Cys Asn Cys Ser Val His Glu
            180                 185                 190

Cys Cys Glu Cys Leu Val Pro Val Pro Thr Ala Lys Leu Asn Asp Thr
195                 200                 205

Leu Leu Met Cys Leu Lys Ile Thr Ser Gly Gly Val Ile Phe Gln Ser
210                 215                 220

Pro Leu Met Ser Val Gln Pro Ile Asn Met Val Lys Pro Asp Pro Pro
225                 230                 235                 240

Leu Gly Leu His Met Glu Ile Thr Asp Asp Gly Asn Leu Lys Ile Ser
            245                 250                 255

Trp Ser Ser Pro Pro Leu Val Pro Phe Pro Leu Gln Tyr Gln Val Lys
            260                 265                 270

Tyr Ser Glu Asn Ser Thr Thr Val Ile Arg Glu Ala Asp Lys Ile Val
            275                 280                 285

Ser Ala Thr Ser Leu Leu Val Asp Ser Ile Leu Pro Gly Ser Ser Tyr
            290                 295                 300

Glu Val Gln Val Arg Gly Lys Arg Leu Asp Gly Pro Gly Ile Trp Ser
305                 310                 315                 320

Asp Trp Ser Thr Pro Arg Val Phe Thr Thr Gln Asp Val Ile Tyr Phe
                325                 330                 335

Pro Pro Lys Ile Leu Thr Ser Val Gly Ser Asn Val Ser Phe His Cys
            340                 345                 350

Ile Tyr Lys Lys Glu Asn Lys Ile Val Pro Ser Lys Glu Ile Val Trp
            355                 360                 365

Trp Met Asn Leu Ala Glu Lys Ile Pro Gln Ser Gln Tyr Asp Val Val
370                 375                 380

Ser Asp His Val Ser Lys Val Thr Phe Phe Asn Leu Asn Glu Thr Lys
385                 390                 395                 400

Pro Arg Gly Lys Phe Thr Tyr Asp Ala Val Tyr Cys Cys Asn Glu His
                405                 410                 415

Glu Cys His His Arg Tyr Ala Glu Leu Tyr Val Ile Asp Val Asn Ile
            420                 425                 430

Asn Ile Ser Cys Glu Thr Asp Gly Tyr Leu Thr Lys Met Thr Cys Arg
            435                 440                 445

Trp Ser Thr Ser Thr Ile Gln Ser Leu Ala Glu Ser Thr Leu Gln Leu
450                 455                 460

Arg Tyr His Arg Ser Ser Leu Tyr Cys Ser Asp Ile Pro Ser Ile His
465                 470                 475                 480

Pro Ile Ser Glu Pro Lys Asp Cys Tyr Leu Gln Ser Asp Gly Phe Tyr
                485                 490                 495

Glu Cys Ile Phe Gln Pro Ile Phe Leu Leu Ser Gly Tyr Thr Met Trp
            500                 505                 510

Ile Arg Ile Asn His Ser Leu Gly Ser Leu Asp Ser Pro Pro Thr Cys
            515                 520                 525

Val Leu Pro Asp Ser Val Val Lys Pro Leu Pro Pro Ser Ser Val Lys
```

-continued

```
            530                 535                 540
Ala Glu Ile Thr Ile Asn Ile Gly Leu Leu Lys Ile Ser Trp Glu Lys
545                 550                 555                 560

Pro Val Phe Pro Glu Asn Asn Leu Gln Phe Gln Ile Arg Tyr Gly Leu
                565                 570                 575

Ser Gly Lys Glu Val Gln Trp Lys Met Tyr Glu Val Tyr Asp Ala Lys
            580                 585                 590

Ser Lys Ser Val Ser Leu Pro Val Pro Asp Leu Cys Ala Val Tyr Ala
        595                 600                 605

Val Gln Val Arg Cys Lys Arg Leu Asp Gly Leu Gly Tyr Trp Ser Asn
    610                 615                 620

Trp Ser Asn Pro Ala Tyr Thr Val Val Met Asp Ile Lys Val Pro Met
625                 630                 635                 640

Arg Gly Pro Glu Phe Trp Arg Ile Ile Asn Gly Asp Thr Met Lys Lys
                645                 650                 655

Glu Lys Asn Val Thr Leu Leu Trp Lys Pro Leu Met Lys Asn Asp Ser
            660                 665                 670

Leu Cys Ser Val Gln Arg Tyr Val Ile Asn His His Thr Ser Cys Asn
        675                 680                 685

Gly Thr Trp Ser Glu Asp Val Gly Asn His Thr Lys Phe Thr Phe Leu
    690                 695                 700

Trp Thr Glu Gln Ala His Thr Val Thr Val Leu Ala Ile Asn Ser Ile
705                 710                 715                 720

Gly Ala Ser Val Ala Asn Phe Asn Leu Thr Phe Ser Trp Pro Met Ser
                725                 730                 735

Lys Val Asn Ile Val Gln Ser Leu Ser Ala Tyr Pro Leu Asn Ser Ser
            740                 745                 750

Cys Val Ile Val Ser Trp Ile Leu Ser Pro Ser Asp Tyr Lys Leu Met
        755                 760                 765

Tyr Phe Ile Ile Glu Trp Lys Asn Leu Asn Glu Asp Gly Glu Ile Lys
    770                 775                 780

Trp Leu Arg Ile Ser Ser Ser Val Lys Lys Tyr Tyr Ile His Asp His
785                 790                 795                 800

Phe Ile Pro Ile Glu Lys Tyr Gln Phe Ser Leu Tyr Pro Ile Phe Met
                805                 810                 815

Glu Gly Val Gly Lys Pro Lys Ile Ile Asn Ser Phe Thr Gln Asp Asp
            820                 825                 830

Ile Glu Lys His Gln Ser Asp Ala Gly Leu Tyr Val Ile Val Pro Val
        835                 840                 845

Ile Ile Ser Ser Ser Ile Leu Leu Leu Gly Thr Leu Leu Ile Ser His
    850                 855                 860

Gln Arg Met Lys Lys Leu Phe Trp Glu Asp Val Pro Asn Pro Lys Asn
865                 870                 875                 880

Cys Ser Trp Ala Gln Gly Leu Asn Phe Gln Lys Pro Glu Thr Phe Glu
                885                 890                 895

His Leu Phe Ile Lys His Thr Ala Ser Val Thr Cys Gly Pro Leu Leu
            900                 905                 910

Leu Glu Pro Glu Thr Ile Ser Glu Asp Ile Ser Val Asp Thr Ser Trp
        915                 920                 925

Lys Asn Lys Asp Glu Met Met Pro Thr Thr Val Val Ser Leu Leu Ser
    930                 935                 940

Thr Thr Asp Leu Glu Lys Gly Ser Val Cys Ile Ser Asp Gln Phe Asn
945                 950                 955                 960
```

```
Ser Val Asn Phe Ser Glu Ala Glu Gly Thr Glu Val Thr Tyr Glu Asp
                965             970                 975

Glu Ser Gln Arg Gln Pro Phe Val Lys Tyr Ala Thr Leu Ile Ser Asn
            980             985                 990

Ser Lys Pro Ser Glu Thr Gly Glu  Glu Gln Gly Leu Ile  Asn Ser Ser
        995             1000                 1005

Val Thr Lys Cys Phe Ser Ser  Lys Asn Ser Pro Leu  Lys Asp Ser
    1010             1015                 1020

Phe Ser Asn Ser Ser Trp Glu  Ile Glu Ala Gln Ala  Phe Phe Ile
        1025         1030                 1035

Leu Ser Asp Gln His Pro Asn  Ile Ile Ser Pro His  Leu Thr Phe
        1040             1045                 1050

Ser Glu Gly Leu Asp Glu Leu  Leu Lys Leu Glu Gly  Asn Phe Pro
        1055             1060             1065

Glu Glu Asn Asn Asp Lys Lys  Ser Ile Tyr Tyr Leu  Gly Val Thr
        1070             1075             1080

Ser Ile Lys Lys Arg Glu Ser  Gly Val Leu Leu Thr  Asp Lys Ser
        1085             1090                 1095

Arg Val Ser Cys Pro Phe Pro  Ala Pro Cys Leu Phe  Thr Asp Ile
    1100             1105                 1110

Arg Val Leu Gln Asp Ser Cys  Ser His Phe Val Glu  Asn Asn Ile
    1115             1120                 1125

Asn Leu Gly Thr Ser Ser Lys  Lys Thr Phe Ala Ser  Tyr Met Pro
    1130             1135             1140

Gln Phe Gln Thr Cys Ser Thr  Gln Thr His Lys Ile  Met Glu Asn
    1145             1150                 1155

Lys Met Cys Asp Leu Thr Val
    1160             1165
```